United States Patent
Nakajima et al.

(10) Patent No.: US 9,524,871 B2
(45) Date of Patent: Dec. 20, 2016

(54) SILICON-CONTAINING RESIST UNDERLAYER FILM-FORMING COMPOSITION HAVING SULFONE STRUCTURE

(75) Inventors: Makoto Nakajima, Toyama (JP); Daisuke Sakuma, Funabashi (JP); Yuta Kanno, Toyama (JP); Takahiro Kishioka, Toyama (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

(21) Appl. No.: 14/236,136

(22) PCT Filed: Aug. 10, 2012

(86) PCT No.: PCT/JP2012/070549
§ 371 (c)(1),
(2), (4) Date: Jan. 30, 2014

(87) PCT Pub. No.: WO2013/022099
PCT Pub. Date: Feb. 14, 2013

(65) Prior Publication Data
US 2014/0170855 A1   Jun. 19, 2014

(30) Foreign Application Priority Data

Aug. 10, 2011 (JP) ................................. 2011-175355

(51) Int. Cl.
| H01L 21/027 | (2006.01) |
| G03F 7/11 | (2006.01) |
| C07F 7/18 | (2006.01) |
| G03F 7/075 | (2006.01) |
| G03F 7/09 | (2006.01) |
| H01L 21/311 | (2006.01) |

(52) U.S. Cl.
CPC ........... H01L 21/0274 (2013.01); C07F 7/182 (2013.01); G03F 7/0752 (2013.01); G03F 7/091 (2013.01); G03F 7/094 (2013.01); H01L 21/0276 (2013.01); H01L 21/31133 (2013.01)

(58) Field of Classification Search
CPC ..... H01L 21/0276; G03F 7/0752; C07F 7/182
See application file for complete search history.

(56) References Cited

U.S. PATENT DOCUMENTS

| 3,483,241 | A | * | 12/1969 | Berger ........................... 556/428 |
| 7,470,803 | B2 | * | 12/2008 | Saso et al. .................... 556/427 |
| 2006/0009572 | A1 | * | 1/2006 | Lovell ......................... C08J 3/24 |
| | | | | 524/700 |
| 2010/0016286 | A1 | * | 1/2010 | Grainger ............ A61K 31/4015 |
| | | | | 514/212.03 |
| 2012/0178261 | A1 | * | 7/2012 | Kanno et al. ................. 438/703 |

FOREIGN PATENT DOCUMENTS

| JP | A-2005-112732 | 4/2005 |
| JP | A-2006-188487 | 7/2006 |
| WO | WO 2011/033965 A1 | 3/2011 |

OTHER PUBLICATIONS

Structures of compounds set forth from the American Chemical Society as found in Scifinder database as registry numbers listed for U.S. Pat. No. 7,470,803 down loaded , 2 pages.*
Grant et al , eds, Grant & Hackh's Chemical Dictionary, fifth ed, "sulfonyl*" , p. 561, McGraw-Hill, Inc, New York, NY, 1987.*
Oct. 23, 2012 translation of Written Opinion issued in International Application No. PCT/JP2012/070549.

* cited by examiner

Primary Examiner — Cynthia Hamilton
(74) Attorney, Agent, or Firm — Oliff PLC

(57) ABSTRACT

A composition for forming a resist underlayer film for lithography, including: as a silane, a hydrolyzable organosilane, a hydrolysate of the hydrolyzable organosilane, or a hydrolysis-condensation product of the hydrolyzable organosilane, wherein the hydrolyzable organosilane is a compound of Formula (1):

$$[(R^1)_a Si(R^2)_{(3-a)}]_b (R^3) \qquad \text{Formula (1)}$$

[in Formula (1), $R^3$ is an organic group having a sulfonyl group and a light-absorbing group and is bonded to a Si atom through a Si—C bond; $R^1$ is an alkyl, aryl, aralkyl, halogenated alkyl, halogenated aryl, halogenated aralkyl, alkenyl, an organic group having an epoxy, acryloyl, methacryloyl, mercapto, alkoxyaryl, acyloxyaryl, isocyanurate, hydroxy, cyclic amino, or a cyano group, or a combination of any of these groups and is bonded to a Si atom through a Si—C bond; $R^2$ is an alkoxy group, an acyloxy group, or a halogen group; a is an integer of 0 to 2; and b is an integer of 1 to 3].

11 Claims, No Drawings

SILICON-CONTAINING RESIST UNDERLAYER FILM-FORMING COMPOSITION HAVING SULFONE STRUCTURE

TECHNICAL FIELD

The present invention provides a novel silane compound and relates to a composition for forming an underlayer film between a substrate and a resist (for example, a photoresist, an electron beam resist, and an EUV resist) used for the production of semiconductor devices. The present invention specifically relates to a composition for forming a resist underlayer film for lithography used in order to form an underlayer film used as the underlayer of a photoresist in a lithography process for the production of semiconductor devices. The present invention also relates to a method for forming a resist pattern by use of the composition for forming an underlayer film.

BACKGROUND ART

The production of semiconductor devices has employed lithography using a photoresist for microfabrication. The microfabrication is a processing method that includes forming a photoresist thin film on a semiconductor substrate such as a silicon wafer, irradiating the photoresist with active light such as ultraviolet light through a mask pattern with a pattern for a semiconductor device, developing the photoresist, etching the substrate using the obtained photoresist pattern as a protective film, and thus forming minute unevenness corresponding to the pattern on the substrate surface. In recent years, semiconductor devices have been further integrated, and the active light to be used has been changed from a KrF excimer laser (248 nm) to an ArF excimer laser (193 nm) and EUV rays (13.5 nm) having a shorter wavelength. Such a change raises serious issues due to the effect of reflection of active light from the semiconductor substrate.

As an underlayer film between a semiconductor substrate and a photoresist, a film known as a hard mask containing a metallic element such as silicon is used (for example, see Patent Document 1). In this case, the components of the resist are significantly different from those of the hard mask. Therefore, the speeds at which they are removed largely depend on the gas type used in the dry etching. Appropriate selection of the gas type allows the hard mask to be removed by dry etching without largely reducing the film thickness of the photoresist. Thus, in the recent production of semiconductor devices, a resist underlayer film has been arranged between the semiconductor substrate and the photoresist in order to achieve various effects including an anti-reflection effect. A composition for the resist underlayer film has been studied, but there is still a demand for a new material for the resist underlayer film due to a wide variety of characteristics required.

From another viewpoint, a method for modifying the surface of a substrate has been developed. For example, disclosed is a method of using a silane coupling agent having a sulfonyl group to change the surface into a hydrophilic surface after exposure (see Patent Document 2).

PRIOR ART DOCUMENTS

Patent Documents

Patent Document 1: WO2011/033965 pamphlet
Patent Document 2: Japanese Patent Application Publication No. 2005-112732 (JP 2005-112732 A)

SUMMARY OF THE INVENTION

Problem to be Solved by the Invention

An object of the present invention is to provide a composition for forming a resist underlayer film for lithography that enables microfabrication of a substrate using a rectangular resist pattern and that is usable for the production of semiconductor devices. Specifically, the object of the present invention is to provide a composition for forming a resist underlayer film for lithography used in order to form a resist underlayer film usable as a hard mask. Another object of the present invention is to provide a composition for forming a resist underlayer film for lithography used in order to form a resist underlayer film usable as an anti-reflective coating. Still another object of the present invention is to provide a resist underlayer film for lithography that does not cause intermixing with a resist and has a larger dry etching rate than that of the resist and to provide a composition for forming a resist underlayer film used in order to form the underlayer film.

Means for Solving the Problem

The present invention provides, as a first aspect, a composition for forming a resist underlayer film for lithography, comprising: as a silane, a hydrolyzable organosilane, a hydrolysate of the hydrolyzable organosilane, or a hydrolysis-condensation product of the hydrolyzable organosilane, in which the hydrolyzable organosilane is a compound of Formula (1):

Formula (1)

[in Formula (1), $R^3$ is an organic group having a sulfonyl group and a light-absorbing group and is bonded to a Si atom through a Si—C bond; $R^1$ is an alkyl group, an aryl group, an aralkyl group, a halogenated alkyl group, a halogenated aryl group, a halogenated aralkyl group, an alkenyl group, an organic group having an epoxy group, an acryloyl group, a methacryloyl group, a mercapto group, an alkoxyaryl group, an acyloxyaryl group, an isocyanurate group, a hydroxy group, a cyclic amino group, or a cyano group, or a combination of any of these groups and is bonded to a Si atom through a Si—C bond; $R^2$ is an alkoxy group, an acyloxy group, or a halogen group; a is an integer of 0 to 2; and b is an integer of 1 to 3];

as a second aspect, the composition for forming a resist underlayer film for lithography according to the first aspect, in which $R^3$ in Formula (1) is a group of Formula (2):

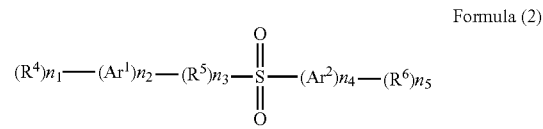

Formula (2)

[in Formula (2), one to three groups of groups of $R^4$, $Ar^1$, $R^5$, $Ar^2$, and $R^6$ are bonded to a Si atom through a Si—C bond;

R$^4$ is a monovalent to tetravalent hydrocarbon group optionally having a sulfide bond or an ether bond; R$^5$ is a divalent to tetravalent hydrocarbon group optionally having a sulfide bond or an ether bond; R$^6$ is an optionally substituted monovalent to tetravalent hydrocarbon group; each of Ar$^1$ and Ar$^2$ is an optionally substituted C$_{6-20}$ arylene group or an optionally substituted C$_{6-20}$ aryl group; n$_2$ is an integer of 1; each of n$_1$, n$_3$, n$_4$, and n$_5$ is an integer of 0 or 1; and n$_4$ and n$_5$ are not simultaneously an integer of 0];

as a third aspect, the composition for forming a resist underlayer film for lithography according to the first aspect or the second aspect, in which the hydrolyzable organosilane includes a combination of at least one organic silicon compound selected from the group consisting of Formula (3):

$$R^1{}_aSi(R^2)_{4-a} \quad \text{Formula (3)}$$

(in Formula (3), R$^1$ is an alkyl group, an aryl group, an aralkyl group, a halogenated alkyl group, a halogenated aryl group, a halogenated aralkyl group, an alkenyl group, an organic group having an epoxy group, an acryloyl group, a methacryloyl group, a mercapto group, an alkoxyaryl group, an acyloxyaryl group, an isocyanurate group, a hydroxy group, a cyclic amino group, or a cyano group, or a combination of any of these groups and is bonded to a silicon atom through a Si—C bond; R$^2$ is an alkoxy group, an acyloxy group, or a halogen group; and a is an integer of 0 to 3) and Formula (4):

$$[R^1{}_cSi(R^2)_{3-c}]_2Y_b \quad \text{Formula (4)}$$

(in Formula (4), R$^1$ is an alkyl group; R$^2$ is an alkoxy group, an acyloxy group, or a halogen group; Y is an alkylene group or an arylene group; b is an integer of 0 or 1; and c is an integer of 0 or 1) and the hydrolyzable organosilane of Formula (1), a hydrolysate of the combination, or a hydrolysis-condensation product of the combination;

as a fourth aspect, the composition for forming a resist underlayer film according to any one of the first aspect to the third aspect, in which the hydrolysis-condensation product of the compound of Formula (1) or a hydrolysis-condensation product of the compound of Formula (1) and the compound of Formula (3) is included as a polymer;

as a fifth aspect, the composition for forming a resist underlayer film according to any one of the first aspect to the fourth aspect, further comprising an acid;

as a sixth aspect, the composition for forming a resist underlayer film according to any one of the first aspect to the fifth aspect, further comprising water;

as a seventh aspect, the composition for forming a resist underlayer film according to any one of the first aspect to the sixth aspect, further comprising an ammonium compound, a cyclic ammonium compound, a cyclic amine compound, or a sulfonium compound;

as an eighth aspect, a resist underlayer film obtained by applying the composition for forming a resist underlayer film as described in any one of the first aspect to the seventh aspect onto a semiconductor substrate and baking the composition;

as a ninth aspect, a method for producing a semiconductor device, the method comprising: applying the composition for forming a resist underlayer film as described in any one of the first aspect to the seventh aspect onto a semiconductor substrate and baking the composition to form a resist underlayer film; applying a composition for a resist onto the resist underlayer film to form a resist film; exposing the resist film to light; after the light exposure, developing the resist film to form a resist pattern; etching the resist underlayer film using the resist pattern; and fabricating the semiconductor substrate using the resist film thus patterned and the resist underlayer film thus patterned;

as a tenth aspect, a method for producing a semiconductor device, the method comprising: forming an organic underlayer film on a semiconductor substrate; applying the composition for forming a resist underlayer film as described in any one of the first aspect to the seventh aspect onto the organic underlayer film and baking the composition to form a resist underlayer film; applying a composition for a resist onto the resist underlayer film to form a resist film; exposing the resist film to light; after the light exposure, developing the resist film to form a resist pattern; etching the resist underlayer film using the resist pattern; etching the organic underlayer film using the resist underlayer film thus patterned; and fabricating the semiconductor substrate using the organic underlayer film thus patterned; and as an eleventh aspect, a compound of Formula (5):

$$(R^3)_aSi(R^2)_{(4-a)} \quad \text{Formula (5)}$$

[in Formula (5), R$^2$ is an alkoxy group, an acyloxy group, or a halogen group; a is an integer of 1; and R$^3$ is a group of Formula (6):

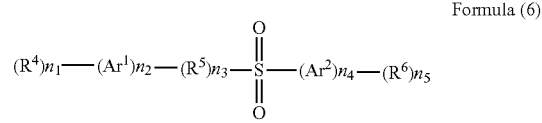
$$(R^4)n_1\text{---}(Ar^1)n_2\text{---}(R^5)n_3\text{---}\overset{\overset{O}{\|}}{\underset{\underset{O}{\|}}{S}}\text{---}(Ar^2)n_4\text{---}(R^6)n_5 \quad \text{Formula (6)}$$

(in Formula (6), one organic group of organic groups of R$^4$, Ar$^1$, R$^5$, Ar$^2$, and R$^6$ is bonded to a Si atom through a Si—C bond; R$^4$ is a monovalent to tetravalent hydrocarbon group optionally having a sulfide bond or an ether bond; R$^5$ is a divalent to tetravalent hydrocarbon group optionally having a sulfide bond or an ether bond; R$^6$ is an optionally substituted monovalent to tetravalent hydrocarbon group; each of Ar$^1$ and Ar$^2$ is an optionally substituted phenylene group or an optionally substituted phenyl group; n$_2$ is an integer of 1; each of n$_1$, n$_3$, n$_4$, and n$_5$ is an integer of 0 or 1; and n$_4$ and n$_5$ are not simultaneously an integer of 0)].

Effect of the Invention

In the present invention, a resist underlayer film is formed on a substrate by coating, or a resist underlayer film is formed on an organic underlayer film on a substrate by coating, and a resist film (for example, a photoresist, an electron beam resist, or an EUV resist) is formed on the resist underlayer film. Next, a resist pattern is formed by exposure and development, and the resist underlayer film is dry etched using the resist pattern to transfer the pattern. The substrate is then fabricated using the pattern. Alternatively, the organic underlayer film is etched to transfer the pattern and the substrate is fabricated using the organic underlayer film.

In order to prevent pattern falling in the formation of a fine pattern, a resist tends to have a smaller film thickness. In the dry etching for transferring a pattern to a film underlying such a resist having a smaller film thickness, the film is required to have a higher etching rate than that of the upper layer film in order to transfer the pattern. In the present invention, a substrate is coated with a resist underlayer film (containing an inorganic silicon compound) of the present application, via an organic underlayer film on the substrate or without an organic underlayer film, and is further coated with a resist film (an organic resist film). The dry etching rate of a film containing an organic component is largely different from that of a film containing an inorganic component depending on an etching gas to be selected. The film containing an organic component has a high dry etching rate with an oxygen-containing gas, and the film containing an inorganic component has a high dry etching rate with a halogen-containing gas.

For example, a resist pattern is formed, then the resist underlayer film of the present application underlying the resist pattern is dry etched with a halogen-containing gas to transfer the pattern to the resist underlayer film, and the substrate is fabricated with a halogen-containing gas based on the pattern transferred to the resist underlayer film. Alternatively, the organic underlayer film underlying the resist underlayer film is dry etched with an oxygen-containing gas using the pattern-transferred resist underlayer film to transfer the pattern to the organic underlayer film, and the substrate is fabricated with a halogen-containing gas using the pattern-transferred organic underlayer film.

In the present invention, the resist underlayer film works as a hard mask. In the structure of Formula (1), the hydrolyzable group such as an alkoxy group, an acyloxy group, and a halogen group is hydrolyzed or partially hydrolyzed, and then the silanol group undergoes a condensation reaction to form a polymer having a polysiloxane structure. The polyorganosiloxane structure has a function sufficient for a hard mask.

The polyorganosiloxane structure (interlayer) is effective as the hard mask for etching of an organic underlayer film underlying the resist underlayer film or for the fabrication (etching) of a substrate. In other words, the polyorganosiloxane structure has sufficient dry etching resistivity with respect to an oxygen-containing dry etching gas that is used for the fabrication of a substrate or for the etching of an organic underlayer film.

The resist underlayer film of the present invention improves the dry etching rate with respect to such an upper resist and has the dry etching resistivity during the fabrication of a substrate.

A resist underlayer film formed of the composition for forming a resist underlayer film of the present invention contains a silane compound containing an organic group having a sulfonyl group and a light-absorbing group, a hydrolysate thereof, or a hydrolysis-condensation product thereof and thus forms a rectangular resist pattern after exposure and development. This enables the fabrication of a substrate with a fine pattern.

For example, the resist underlayer film formed by use of a silane compound having a sulfonamide group disclosed in Patent Document 1 is likely to form a resist pattern having a footing shape. However, the resist underlayer film formed by use of the silane compound having a sulfone structure of the present invention can improve the footing of a resist pattern to be formed.

MODES FOR CARRYING OUT THE INVENTION

The present invention relates to a composition for forming a resist underlayer film for lithography, comprising, as a silane, a hydrolyzable organosilane, a hydrolysate thereof, or a hydrolysis-condensation product thereof, in which the silane is represented by Formula (1).

With respect to the total amount of silicon atoms in the silane, the organic group represented by $R^3$ in Formula (1), having a sulfonyl group and a light-absorbing group and bonded to a Si atom through a Si—C bond may be contained in a ratio of less than 50% by mol, for example, 0.5% by mol to 30% by mol, 0.5% by mol to 25% by mol, 0.5% by mol to 15% by mol, or 0.5% by mol to 10% by mol.

The composition for forming a resist underlayer film of the present invention includes a hydrolyzable organosilane of Formula (1), a hydrolysate thereof, or a hydrolysis-condensation product thereof, and a solvent. The composition may further comprise, as optional components, an acid, water, an alcohol, a curing catalyst, an acid generator, an additional organic polymer, a light-absorbing compound, a surfactant and the like.

The solid content in the composition for forming a resist underlayer film of the present invention is, for example, 0.1% by mass to 50% by mass, 0.1% by mass to 30% by mass, or 0.1% by mass to 25% by mass. Here, the solid content is a content of the total components of the composition for forming a resist underlayer film except the solvent component.

The ratio of the hydrolyzable organosilane, a hydrolysate thereof, and a hydrolysis-condensation product thereof in the solid content is 20% by mass or more, for example, 50% by mass to 100% by mass, 60% by mass to 100% by mass, or 70% by mass to 100% by mass.

The hydrolyzable organosilane used in the present invention has a structure of Formula (1). In Formula (1), $R^3$ is an organic group having a sulfonyl group and a light-absorbing group and is bonded to a Si atom through a Si—C bond; and $R^1$ is an alkyl group, an aryl group, an aralkyl group, a halogenated alkyl group, a halogenated aryl group, a halogenated aralkyl group, an alkenyl group, an organic group having an epoxy group, an acryloyl group, a methacryloyl group, a mercapto group, an alkoxyaryl group, an acyloxyaryl group, an isocyanurate group, a hydroxy group, a cyclic amino group, or a cyano group, or a combination of them. $R^2$ may be an alkoxy group, an acyloxy group, or a halogen group. a is an integer of 0 to 2, and b is an integer of 1 to 3. In the structure of Formula (1), a may be an integer of 0 while b may be an integer of 1.

The light-absorbing group is an organic group capable of absorbing exposed light, and examples include aromatic rings such as a benzene ring and a naphthalene ring and unsaturated bond-containing groups such as a vinyl group. A phenyl group and a phenylene group derived from a benzene ring are preferably used.

$R^3$ in Formula (1) may be an organic group having the structure of Formula (2). In Formula (2), one to three organic groups of the groups of $R^4$, $Ar^1$, $R^5$, $Ar^2$, and $R^6$ are bonded to a Si atom through a Si—C bond; $R^4$ is a monovalent to tetravalent hydrocarbon group optionally having a sulfide bond or an ether bond; $R^5$ is a divalent to tetravalent hydrocarbon group optionally having a sulfide bond or an ether bond; each of $Ar^1$ and $Ar^2$ is an optionally substituted $C_{6-20}$ arylene group; $n_2$ is an integer of 1; each of $n_1$, $n_3$, $n_4$, and $n_5$ is an integer of 0 or 1; and $n_4$ and $n_5$ are not simultaneously an integer of 0.

In Formula (2), a structure may be selected in which one organic group of the groups of $R^4$, $Ar^1$, $R^5$, $Ar^2$, and $R^6$ is bonded to a Si atom through a Si—C bond.

$R^4$, $R^5$, $R^6$, $Ar^1$ and $Ar^2$ may be substituted, and examples of the substituent include a halogen group and an alkoxy group described below. Examples of the halogen group include fluorine, chlorine, bromine, and iodine, and the alkoxy group is exemplified as below.

The alkyl group is a linear or branched alkyl group having a carbon atom number of 1 to 10, and examples thereof include a methyl group, an ethyl group, an n-propyl group, an i-propyl group, an n-butyl group, an i-butyl group, an s-butyl group, a t-butyl group, an n-pentyl group, a 1-methyl-n-butyl group, a 2-methyl-n-butyl group, a 3-methyl-n-butyl group, a 1,1-dimethyl-n-propyl group, a 1,2-dimethyl-n-propyl group, a 2,2-dimethyl-n-propyl group, a 1-ethyl-n-propyl group, an n-hexyl group, a 1-methyl-n-pentyl group, a 2-methyl-n-pentyl group, a 3-methyl-n-pentyl group, a 4-methyl-n-pentyl group, a 1,1-dimethyl-n-butyl group, a 1,2-dimethyl-n-butyl group, a 1,3-dimethyl-n-butyl group, a 2,2-dimethyl-n-butyl group, a 2,3-dimethyl-n-butyl group, a 3,3-dimethyl-n-butyl group, a 1-ethyl-n-butyl group, a 2-ethyl-n-butyl group, a 1,1,2-trimethyl-n-propyl group, a 1,2,2-trimethyl-n-propyl group, a 1-ethyl-1-methyl-n-propyl group, and a 1-ethyl-2-methyl-n-propyl group. A cyclic alkyl group may be used. Examples of the $C_{1-10}$ cyclic alkyl group include a cyclopropyl group, a cyclobutyl group, a 1-methyl-cyclopropyl group, a 2-methyl-cyclopropyl group, a cyclopentyl group, a 1-methyl-cyclobutyl group, a 2-methyl-cyclobutyl group, a 3-methyl-cyclobutyl group, a 1,2-dimethyl-cyclopropyl group, a 2,3-dimethyl-cyclopropyl group, a 1-ethyl-cyclopropyl group, a 2-ethyl-cyclopropyl group, a cyclohexyl group, a 1-methyl-cyclopentyl group, a 2-methyl-cyclopentyl group, a 3-methyl-cyclopentyl group, a 1-ethyl-cyclobutyl group, a 2-ethyl-cyclobutyl group, a 3-ethyl-cyclobutyl group, a 1,2-dimethyl-cyclobutyl group, a 1,3-dimethyl-cyclobutyl group, a 2,2-dimethyl-cyclobutyl group, a 2,3-dimethyl-cyclobutyl group, a 2,4-dimethyl-cyclobutyl group, a 3,3-dimethyl-cyclobutyl group, a 1-n-propyl-cyclopropyl group, a 2-n-propyl-cyclopropyl group, a 1-i-propyl-cyclopropyl group, a 2-i-propyl-cyclopropyl group, a 1,2,2-trimethyl-cyclopropyl group, a 1,2,3-trimethyl-cyclopropyl group, a 2,2,3-trimethyl-cyclopropyl group, a 1-ethyl-2-methyl-cyclopropyl group, a 2-ethyl-1-methyl-cyclopropyl group, a 2-ethyl-2-methyl-cyclopropyl group, and a 2-ethyl-3-methyl-cyclopropyl group.

The aryl group is exemplified by a $C_{6-20}$ aryl group, and examples thereof include a phenyl group, an o-methylphenyl group, an m-methylphenyl group, a p-methylphenyl group, an o-chlorophenyl group, an m-chlorophenyl group, a p-chlorophenyl group, an o-fluorophenyl group, a p-mercaptophenyl group, an o-methoxyphenyl group, a p-methoxyphenyl group, a p-aminophenyl group, a p-cyanophenyl group, an α-naphthyl group, a β-naphthyl group, an o-biphenylyl group, an m-biphenylyl group, a p-biphenylyl group, a 1-anthryl group, a 2-anthryl group, a 9-anthryl group, a 1-phenanthryl group, a 2-phenanthryl group, a 3-phenanthryl group, a 4-phenanthryl group, and a 9-phenanthryl group.

The alkenyl group is a $C_{2-10}$ alkenyl group, and examples thereof include an ethenyl group, a 1-propenyl group, a 2-propenyl group, a 1-methyl-1-ethenyl group, a 1-butenyl group, a 2-butenyl group, a 3-butenyl group, a 2-methyl-1-propenyl group, a 2-methyl-2-propenyl group, a 1-ethylethenyl group, a 1-methyl-1-propenyl group, a 1-methyl-2-propenyl group, a 1-pentenyl group, a 2-pentenyl group, a 3-pentenyl group, a 4-pentenyl group, a 1-n-propylethenyl group, a 1-methyl-1-butenyl group, a 1-methyl-2-butenyl group, a 1-methyl-3-butenyl group, a 2-ethyl-2-propenyl group, a 2-methyl-1-butenyl group, a 2-methyl-2-butenyl group, a 2-methyl-3-butenyl group, a 3-methyl-1-butenyl group, a 3-methyl-2-butenyl group, a 3-methyl-3-butenyl group, a 1,1-dimethyl-2-propenyl group, a 1-i-propylethenyl group, a 1,2-dimethyl-1-propenyl group, a 1,2-dimethyl-2-propenyl group, a 1-cyclopentenyl group, a 2-cyclopentenyl group, a 3-cyclopentenyl group, a 1-hexenyl group, a 2-hexenyl group, a 3-hexenyl group, a 4-hexenyl group, a 5-hexenyl group, a 1-methyl-1-pentenyl group, a 1-methyl-2-pentenyl group, a 1-methyl-3-pentenyl group, a 1-methyl-4-pentenyl group, a 1-n-butylethenyl group, a 2-methyl-1-pentenyl group, a 2-methyl-2-pentenyl group, a 2-methyl-3-pentenyl group, a 2-methyl-4-pentenyl group, a 2-n-propyl-2-propenyl group, a 3-methyl-1-pentenyl group, a 3-methyl-2-pentenyl group, a 3-methyl-3-pentenyl group, a 3-methyl-4-pentenyl group, a 3-ethyl-3-butenyl group, a 4-methyl-1-pentenyl group, a 4-methyl-2-pentenyl group, a 4-methyl-3-pentenyl group, a 4-methyl-4-pentenyl group, a 1,1-dimethyl-2-butenyl group, a 1,1-dimethyl-3-butenyl group, a 1,2-dimethyl-1-butenyl group, a 1,2-dimethyl-2-butenyl group, a 1,2-dimethyl-3-butenyl group, a 1-methyl-2-ethyl-2-propenyl group, a 1-s-butylethenyl group, a 1,3-dimethyl-1-butenyl group, a 1,3-dimethyl-2-butenyl group, a 1,3-dimethyl-3-butenyl group, a 1-i-butylethenyl group, a 2,2-dimethyl-3-butenyl group, a 2,3-dimethyl-1-butenyl group, a 2,3-dimethyl-2-butenyl group, a 2,3-dimethyl-3-butenyl group, a 2-i-propyl-2-propenyl group, a 3,3-dimethyl-1-butenyl group, a 1-ethyl-1-butenyl group, a 1-ethyl-2-butenyl group, a 1-ethyl-3-butenyl group, a 1-n-propyl-1-propenyl group, a 1-n-propyl-2-propenyl group, a 2-ethyl-1-butenyl group, a 2-ethyl-2-butenyl group, a 2-ethyl-3-butenyl group, a 1,1,2-trimethyl-2-propenyl group, a 1-t-butylethenyl group, a 1-methyl-1-ethyl-2-propenyl group, a 1-ethyl-2-methyl-1-propenyl group, a 1-ethyl-2-methyl-2-propenyl group, a 1-i-propyl-1-propenyl group, a 1-i-propyl-2-propenyl group, a 1-methyl-2-cyclopentenyl group, a 1-methyl-3-cyclopentenyl group, a 2-methyl-1-cyclopentenyl group, a 2-methyl-2-cyclopentenyl group, a 2-methyl-3-cyclopentenyl group, a 2-methyl-4-cyclopentenyl group, a 2-methyl-5-cyclopentenyl group, a 2-methylene-cyclopentyl group, a 3-methyl-1-cyclopentenyl group, a 3-methyl-2-cyclopentenyl group, a 3-methyl-3-cyclopentenyl group, a 3-methyl-4-cyclopentenyl group, a 3-methyl-5-cyclopentenyl group, a 3-methylene-cyclopentyl group, a 1-cyclohexenyl group, a 2-cyclohexenyl group, and a 3-cyclohexenyl group.

The aralkyl group is an alkyl group substituted with an aryl group, and examples thereof include a $C_{1-10}$ alkyl group substituted with a phenyl group. Specific examples include a benzyl group, an ethylphenyl group, a propylphenyl group, and a butylphenyl group.

These organic groups may be substituted with a halogen atom such as fluorine, chlorine, bromine, and iodine.

Examples of the organic group having an epoxy group include a glycidoxymethyl group, a glycidoxyethyl group, a glycidoxypropyl group, a glycidoxybutyl group, and an epoxycyclohexyl group.

Examples of the organic group having an acryloyl group include an acryloylmethyl group, an acryloylethyl group, and an acryloylpropyl group.

Examples of the organic group having a methacryloyl group include a methacryloylmethyl group, a methacryloylethyl group, and a methacryloylpropyl group.

Examples of the organic group having a mercapto group include an ethylmercapto group, a butylmercapto group, a hexylmercapto group, and an octylmercapto group.

The organic group having an alkoxyaryl group is an aryl group substituted with an alkoxy group or an organic group having such an aryl group. These alkoxy groups and aryl groups can be exemplified by the above and the below.

The organic group having an acyloxyaryl group is an aryl group substituted with an acyloxy group or an organic group having such an aryl group. These acyloxy groups and aryl groups can be exemplified by the above and the below.

Examples of the organic group having an isocyanurate group include an isocyanurate group and a cyanurate alkylene group, and the alkylene group can be exemplified by a group corresponding to the alkyl group above. The isocyanurate group may be substituted with an alkenyl group such as an allyl group, an epoxy-containing group such as a glycidyl group, an alkyl group, or the like.

Examples of the organic group having a hydroxy group include a hydroxy group, a hydroxyalkyl group, and a hydroxyalkylene group. The alkyl group can be exemplified by the above, and the alkylene group can be exemplified by a group corresponding to the alkyl group.

Examples of the organic group having a cyclic amino group include a cyclic amino group and a cyclic aminoalkylene group. Examples of the cyclic amino group include an imidazole group and a 4,5-dihydroimidazole group. The alkylene group can be exemplified by a group corresponding to the alkyl group. Examples include a propylimidazole group and a propyl-4,5-dihydroimidazole group. These groups can be used as a cyclic amine compound.

Examples of the organic group having a cyano group include a cyanoethyl group and a cyanopropyl group.

$R^4$, $R^5$, and $R^6$ are an optionally substituted monovalent to tetravalent hydrocarbon group, and examples thereof include a $C_{1-10}$ alkyl group and alkylene group. The alkyl group may be the alkyl group described above, and the alkylene group is a divalent or trivalent hydrocarbon group derived from the alkyl group. Each of $Ar^1$ and $Ar^2$ is an optionally substituted $C_{6-20}$ arylene group. Examples of the substituent include a halogen atom and an alkoxy group. The halogen atom and the alkoxy group can be exemplified by the above and the below.

Examples of the substituent for $R^4$, $R^5$, $R^6$, $Ar^1$, and $Ar^2$ include the halogen atom described above.

Examples of the hydrocarbon group optionally having a sulfide bond or an ether bond include organic groups such as —S—R—, —R—S—R—, —O—R—, and —R—O—R—. R can be bonded to a Si atom through a Si—C bond. Here, R is the alkyl group described above or an alkylene group derived from the alkyl group.

The $C_{1-20}$ alkoxy group in Formula (1) is exemplified by an alkoxy group having a linear, branched, or cyclic alkyl moiety having a carbon atom number of 1 to 20, and examples thereof include a methoxy group, an ethoxy group, an n-propoxy group, an i-propoxy group, an n-butoxy group, an i-butoxy group, an s-butoxy group, a t-butoxy group, an n-pentyloxy group, a 1-methyl-n-butoxy group, a 2-methyl-n-butoxy group, a 3-methyl-n-butoxy group, a 1,1-dimethyl-n-propoxy group, a 1,2-dimethyl-n-propoxy group, a 2,2-dimethyl-n-propoxy group, a 1-ethyl-n-propoxy group, an n-hexyloxy group, a 1-methyl-n-pentyloxy group, a 2-methyl-n-pentyloxy group, a 3-methyl-n-pentyloxy group, a 4-methyl-n-pentyloxy group, a 1,1-dimethyl-n-butoxy group, a 1,2-dimethyl-n-butoxy group, a 1,3-dimethyl-n-butoxy group, a 2,2-dimethyl-n-butoxy group, a 2,3-dimethyl-n-butoxy group, a 3,3-dimethyl-n-butoxy group, a 1-ethyl-n-butoxy group, a 2-ethyl-n-butoxy group, a 1,1,2-trimethyl-n-propoxy group, a 1,2,2-trimethyl-n-propoxy group, a 1-ethyl-1-methyl-n-propoxy group, and a 1-ethyl-2-methyl-n-propoxy group. Examples of the cyclic alkoxy group include a cyclopropoxy group, a cyclobutoxy group, a 1-methyl-cyclopropoxy group, a 2-methyl-cyclopropoxy group, a cyclopentyloxy group, a 1-methyl-cyclobutoxy group, a 2-methyl-cyclobutoxy group, a 3-methyl-cyclobutoxy group, a 1,2-dimethyl-cyclopropoxy group, a 2,3-dimethyl-cyclopropoxy group, a 1-ethyl-cyclopropoxy group, a 2-ethyl-cyclopropoxy group, a cyclohexyloxy group, a 1-methyl-cyclopentyloxy group, a 2-methyl-cyclopentyloxy group, a 3-methyl-cyclopentyloxy group, a 1-ethyl-cyclobutoxy group, a 2-ethyl-cyclobutoxy group, a 3-ethyl-cyclobutoxy group, a 1,2-dimethyl-cyclobutoxy group, a 1,3-dimethyl-cyclobutoxy group, a 2,2-dimethyl-cyclobutoxy group, a 2,3-dimethyl-cyclobutoxy group, a 2,4-dimethyl-cyclobutoxy group, a 3,3-dimethyl-cyclobutoxy group, a 1-n-propyl-cyclopropoxy group, a 2-n-propyl-cyclopropoxy group, a 1-i-propyl-cyclopropoxy group, a 2-i-propyl-cyclopropoxy group, a 1,2,2-trimethyl-cyclopropoxy group, a 1,2,3-trimethyl-cyclopropoxy group, a 2,2,3-trimethyl-cyclopropoxy group, a 1-ethyl-2-methyl-cyclopropoxy group, a 2-ethyl-1-methyl-cyclopropoxy group, a 2-ethyl-2-methyl-cyclopropoxy group, and a 2-ethyl-3-methyl-cyclopropoxy group.

Examples of the $C_{2-20}$ acyloxy group in Formula (1) include a methylcarbonyloxy group, an ethylcarbonyloxy group, an n-propylcarbonyloxy group, an i-propylcarbonyloxy group, an n-butylcarbonyloxy group, an i-butylcarbonyloxy group, an s-butylcarbonyloxy group, a t-butylcarbonyloxy group, an n-pentylcarbonyloxy group, a 1-methyl-n-butylcarbonyloxy group, a 2-methyl-n-butylcarbonyloxy group, a 3-methyl-n-butylcarbonyloxy group, a 1,1-dimethyl-n-propylcarbonyloxy group, a 1,2-dimethyl-n-propylcarbonyloxy group, a 2,2-dimethyl-n-propylcarbonyloxy group, a 1-ethyl-n-propylcarbonyloxy group, an n-hexylcarbonyloxy group, a 1-methyl-n-pentylcarbonyloxy group, a 2-methyl-n-pentylcarbonyloxy group, a 3-methyl-n-pentylcarbonyloxy group, a 4-methyl-n-pentylcarbonyloxy group, a 1,1-dimethyl-n-butylcarbonyloxy group, a 1,2-dimethyl-n-butylcarbonyloxy group, a 1,3-dimethyl-n-butylcarbonyloxy group, a 2,2-dimethyl-n-butylcarbonyloxy group, a 2,3-dimethyl-n-butylcarbonyloxy group, a 3,3-dimethyl-n-butylcarbonyloxy group, a 1-ethyl-n-butylcarbonyloxy group, a 2-ethyl-n-butylcarbonyloxy group, a 1,1,2-trimethyl-n-propylcarbonyloxy group, a 1,2,2-trimethyl-n-propylcarbonyloxy group, a 1-ethyl-1-methyl-n-propylcarbonyloxy group, a 1-ethyl-2-methyl-n-propylcarbonyloxy group, a phenylcarbonyloxy group, and a tosylcarbonyloxy group.

Examples of the halogen group in Formula (1) include fluorine, chlorine, bromine, and iodine.

The hydrolyzable organosilane (1) is exemplified by the compounds below. In the formulae, Me is a methyl group and Et is an ethyl group.

Formula (1-1)

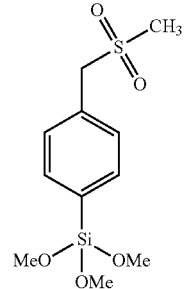

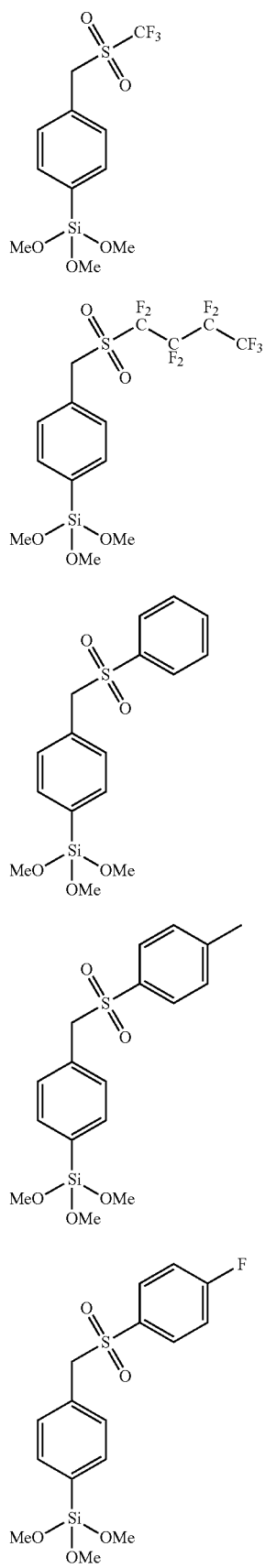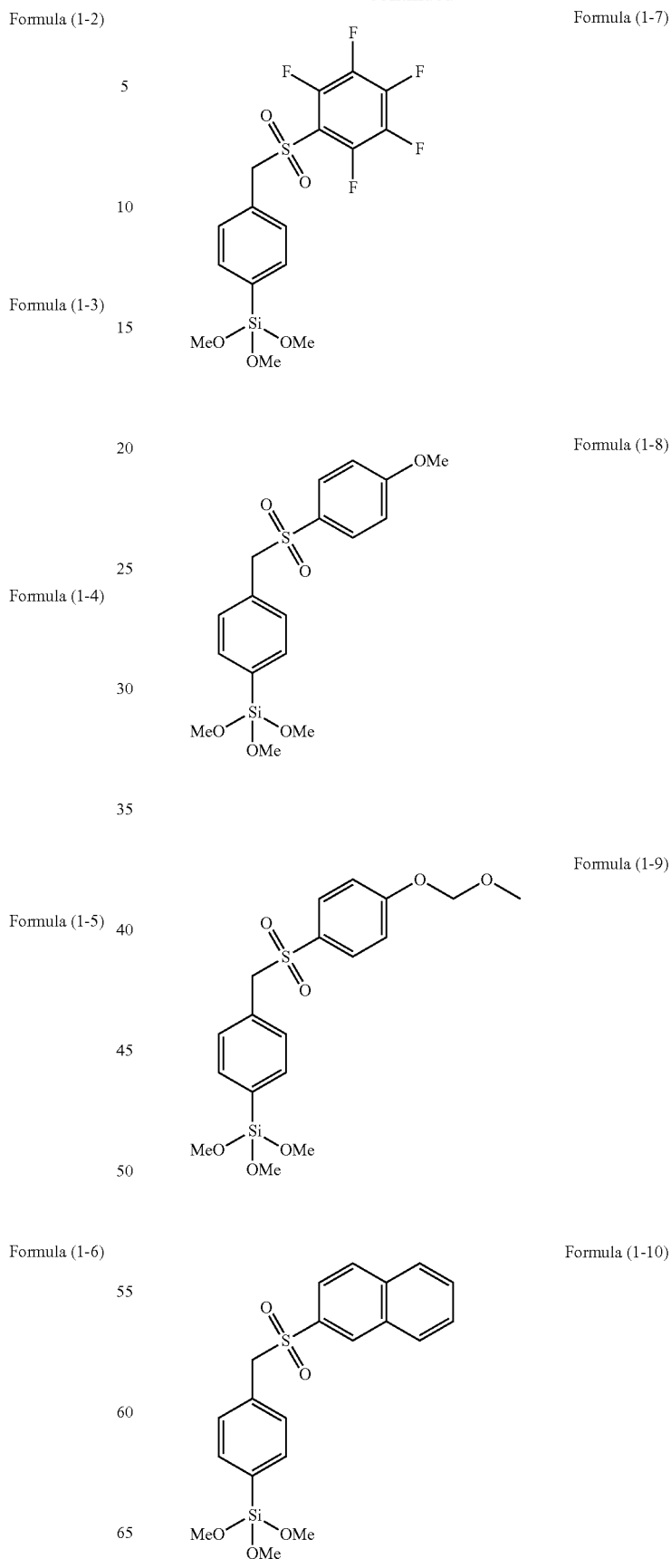

Formula (1-11)
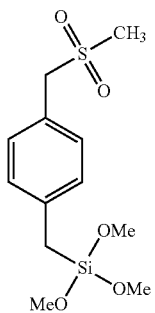
Formula (1-15)
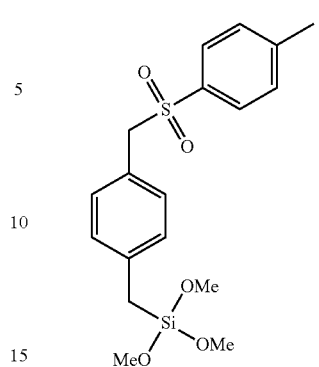
Formula (1-12)
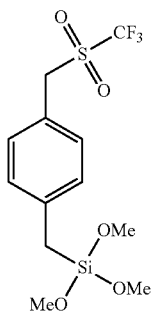
Formula (1-16)
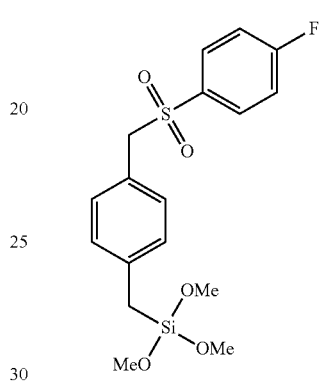
Formula (1-13)
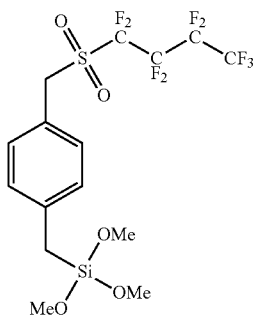
Formula (1-17)
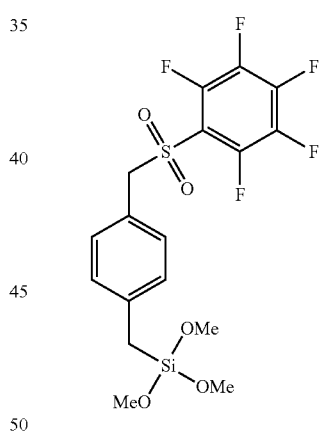
Formula (1-14)
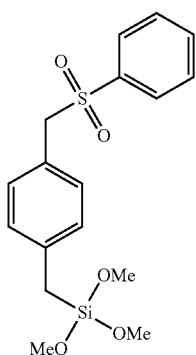
Formula (1-18)
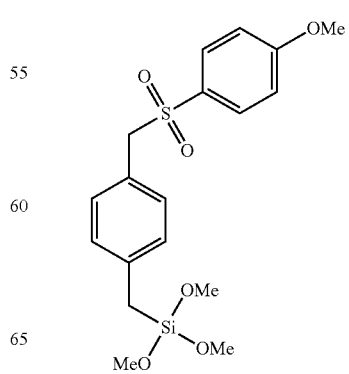

Formula (1-19)
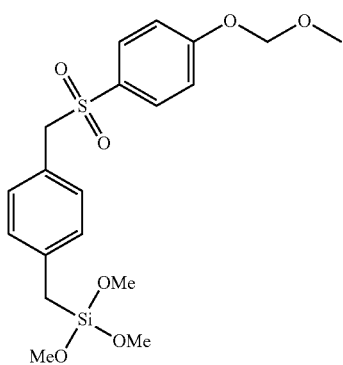
Formula (1-20)
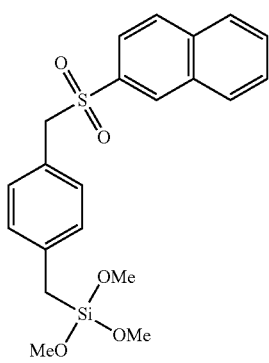
Formula (1-21)
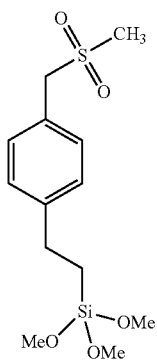
Formula (1-22)
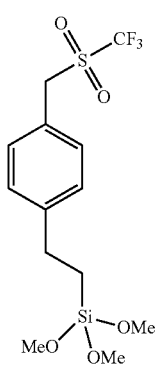
Formula (1-23)
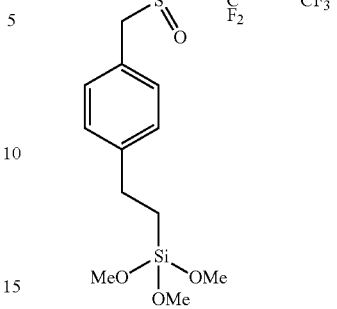
Formula (1-24)
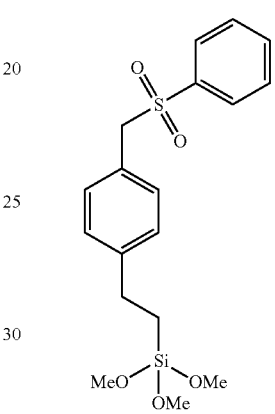
Formula (1-25)
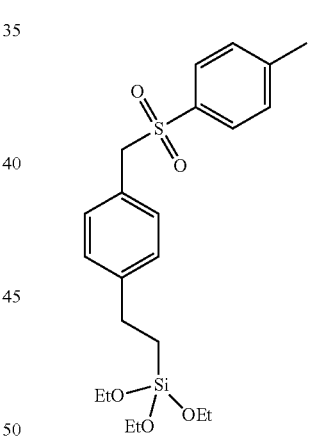
Formula (1-26)
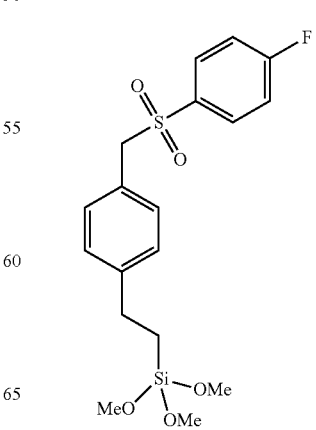

Formula (1-27)
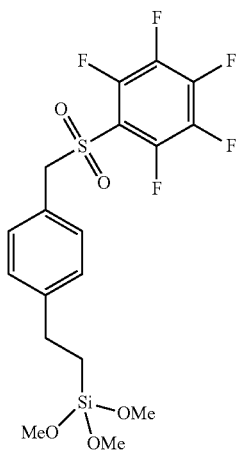
Formula (1-30)
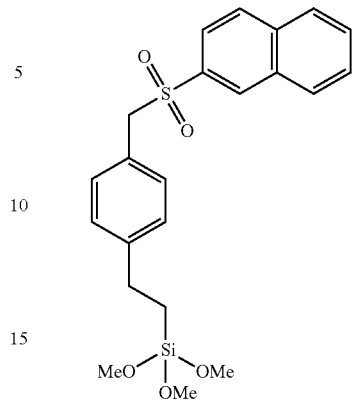
Formula (1-31)
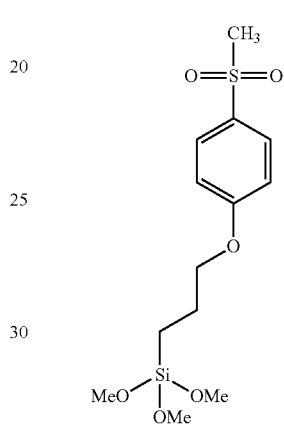
Formula (1-28)
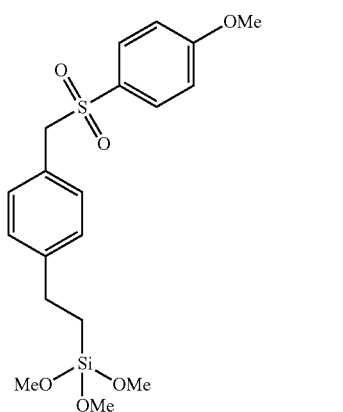
Formula (1-32)
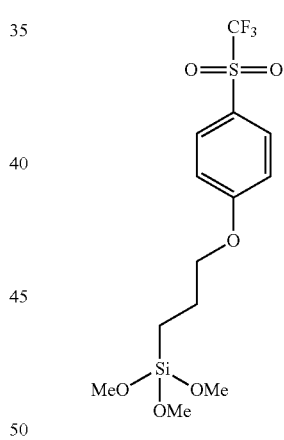
Formula (1-29)
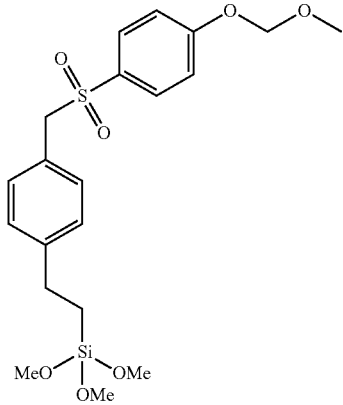
Formula (1-33)
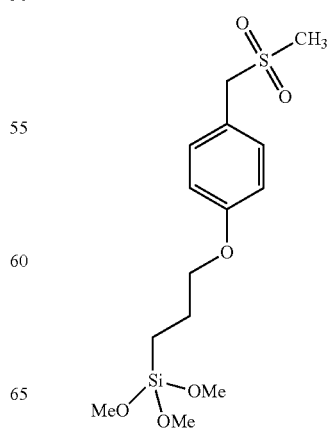

Formula (1-34)
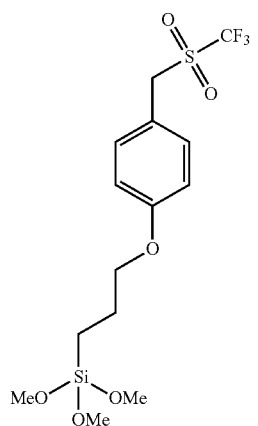
Formula (1-35)
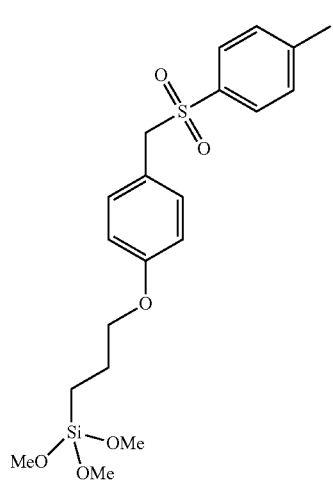
Formula (1-36)
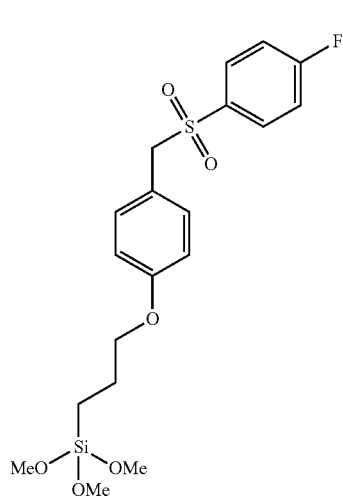
Formula (1-37)
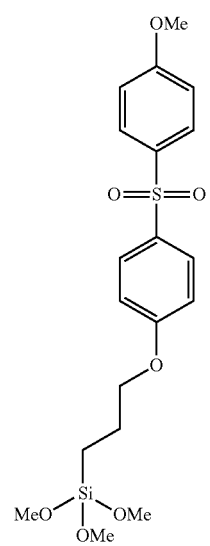
Formula (1-38)
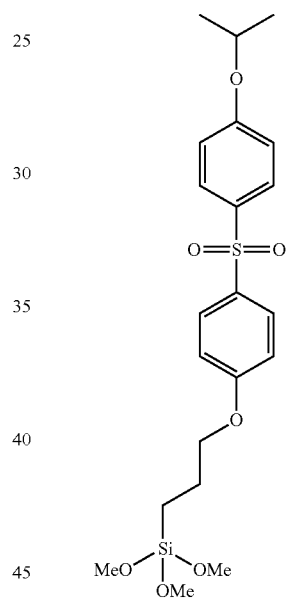
Formula (1-39)
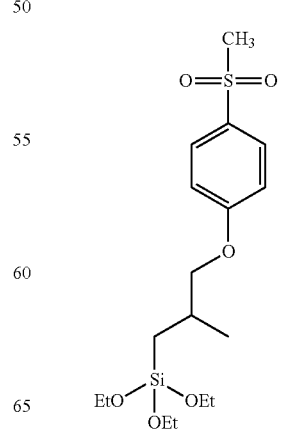

Formula (1-40)
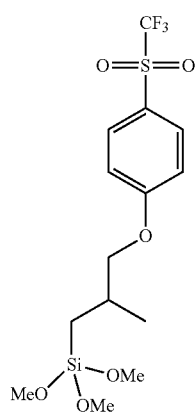
Formula (1-43)
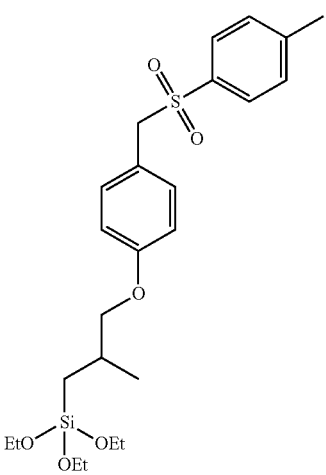
Formula (1-41)
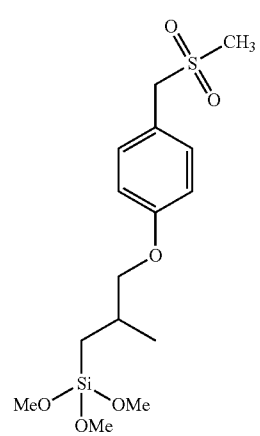
Formula (1-44)
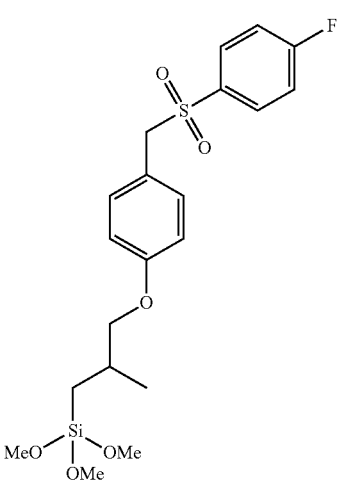
Formula (1-42)
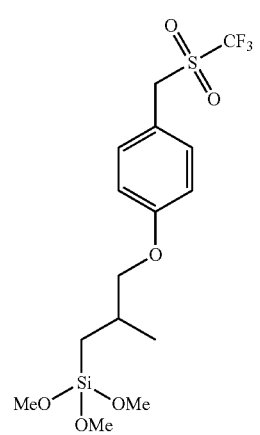
Formula (1-45)
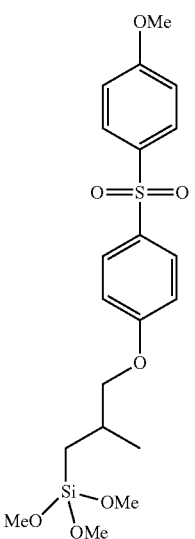

Formula (1-46)
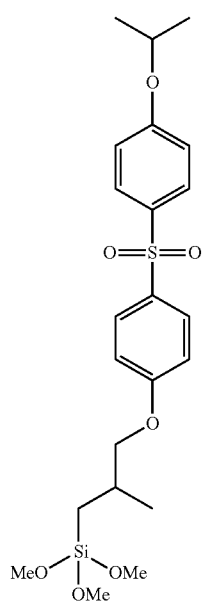
Formula (1-47)
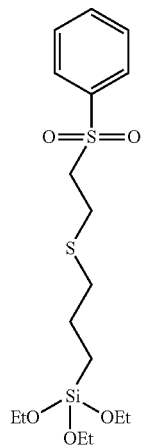
Formula (1-48)
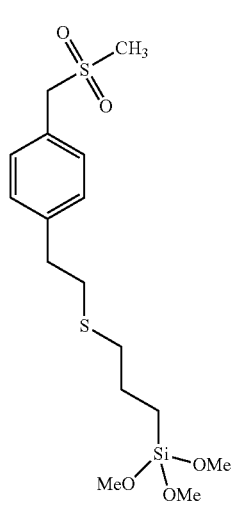
Formula (1-49)
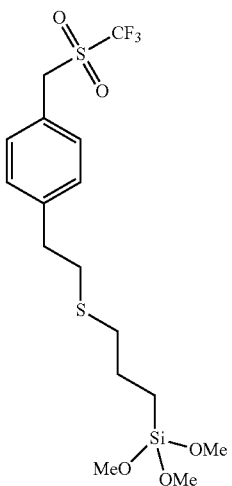
Formula (1-50)
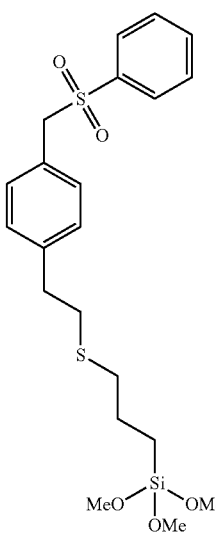
Formula (1-51)
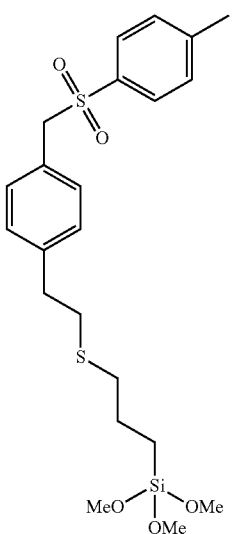

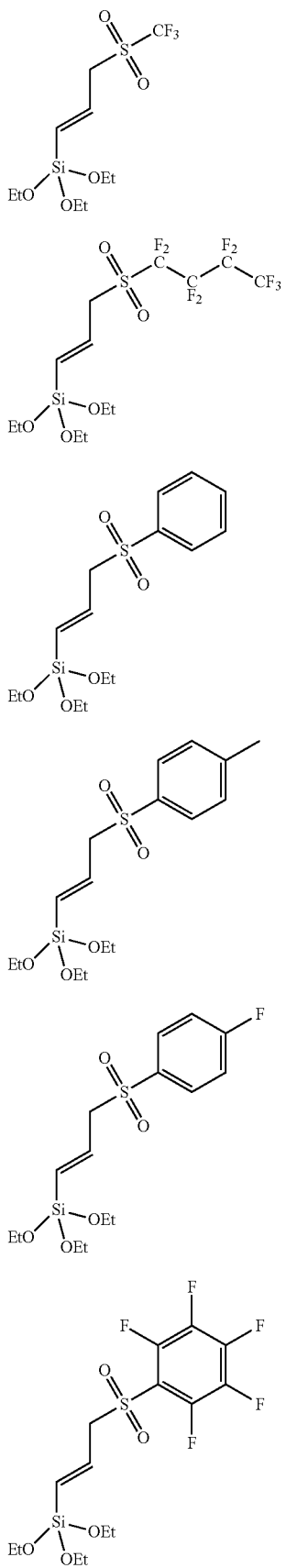
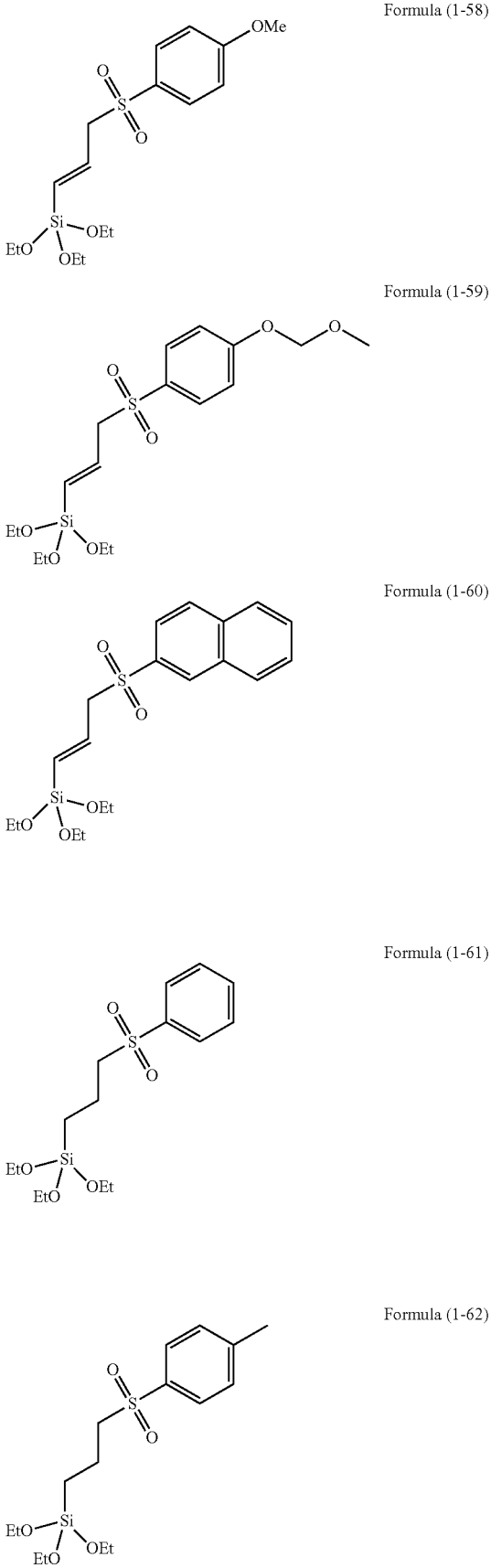

Formula (1-63)
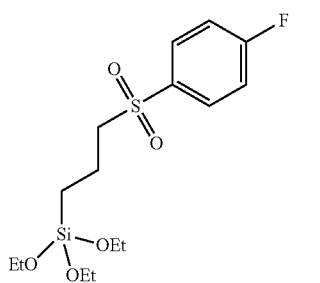

Formula (1-64)
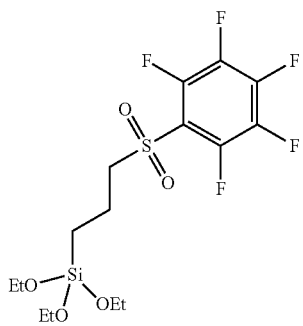

Formula (1-65)
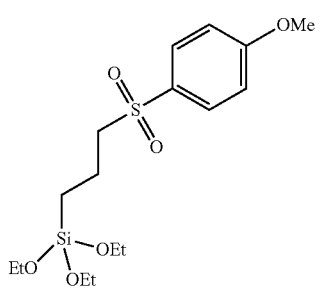

Formula (1-66)
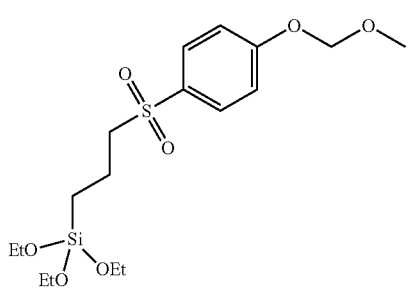

Formula (1-67)
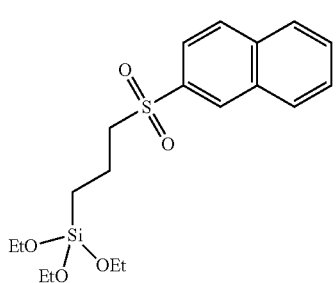

Formula (1-68)
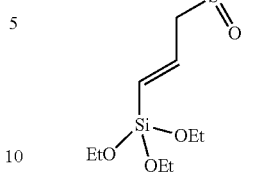

Formula (1-69)
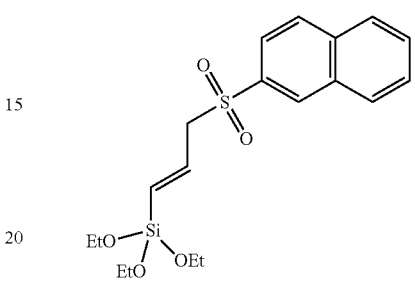

The present invention can include a combination of at least one organic silicon compound selected from the group consisting of a hydrolyzable organosilane of Formula (3) and a hydrolyzable organosilane of Formula (4) and the hydrolyzable organosilane of Formula (1), a hydrolysate thereof, or a hydrolysis-condensation product thereof.

The present invention can employ a hydrolysis-condensation product of the hydrolyzable organosilane of Formula (1) or a hydrolysis-condensation product of the hydrolyzable organosilane of Formula (1) and the hydrolyzable organosilane of Formula (3).

The present invention can employ the hydrolyzable organosilane of Formula (1) in combination with the hydrolyzable organosilane of Formula (3).

In other words, the hydrolyzable organosilane of Formula (1), a hydrolysate thereof, or a hydrolysis-condensation product thereof can be used in combination with the silicon-containing compound of Formula (3), a hydrolysate thereof, or a hydrolysis-condensation product thereof.

The hydrolyzable organosilane of Formula (1) and the silicon-containing compound of Formula (3) can be used in a molar ratio ranging from 1:0 to 1:200. In order to obtain a fine resist shape, the hydrolyzable organosilane of Formula (1) and the silicon-containing compound of Formula (3) can be used in a molar ratio ranging from 1:199 to 1:2.

These compounds are preferably used as a hydrolysis-condensation product (a polymer of polyorganosiloxane). A hydrolysis-condensation product (a polymer of polyorganosiloxane) of the hydrolyzable organosilane of Formula (1) and the hydrolyzable organosilane of Formula (3) is preferably used.

$R^1$ in the hydrolyzable organosilane of Formula (3) is an alkyl group, an aryl group, an aralkyl group, a halogenated alkyl group, a halogenated aryl group, a halogenated aralkyl group, an alkenyl group, an organic group having an epoxy group, an acryloyl group, a methacryloyl group, a mercapto group, an alkoxyaryl group, an acyloxyaryl group, an isocyanurate group, a hydroxy group, a cyclic amino group, or a cyano group, or a combination of them and is bonded to a silicon atom through a Si—C bond. $R^2$ is an alkoxy group, an acyloxy group, or a halogen group, and a is an integer of 0 to 3.

The alkyl group, the aryl group, the aralkyl group, the halogenated alkyl group, the halogenated aryl group, the halogenated aralkyl group, the alkenyl group, or the organic group having an epoxy group, an acryloyl group, a methacryloyl group, a mercapto group, an alkoxyaryl group, an acyloxyaryl group, an isocyanurate group, a hydroxy group, a cyclic amino group, or a cyano group, the alkoxy group, the acyloxy group, or the halogen group included in the hydrolyzable group, which are represented by $R^1$ or $R^2$, can be exemplified by the above for Formula (1).

Examples of the hydrolyzable organosilane of Formula (3) include tetramethoxysilane, tetrachlorosilane, tetraacetoxysilane, tetraethoxysilane, tetra-n-propoxysilane, tetraisopropoxysilane, tetra-n-butoxysilane, methyltrimethoxysilane, methyltriethoxysilane, methyltrichlorosilane, methyltriacetoxysilane, methyltripropoxysilane, methyltriacetoxysilane, methyltributoxysilane, methyltriamiloxysilane, methyltriphenoxysilane, methyltribenzyloxysilane, methyltriphenethyloxysilane, glycidoxymethyltrimethoxysilane, glycidoxymethyltriethoxysilane, α-glycidoxyethyltrimethoxysilane, α-glycidoxyethyltriethoxysilane, β-glycidoxyethyltrimethoxysilane, β-glycidoxyethyltriethoxysilane, α-glycidoxypropyltrimethoxysilane, α-glycidoxypropyltriethoxysilane, β-glycidoxypropyltrimethoxysilane, β-glycidoxypropyltriethoxysilane, γ-glycidoxypropyltrimethoxysilane, γ-glycidoxypropyltriethoxysilane, γ-glycidoxypropyltripropoxysilane, γ-glycidoxypropyltributoxysilane, γ-glycidoxypropyltriphenoxysilane, α-glycidoxybutyltrimethoxysilane, α-glycidoxybutyltriethoxysilane, β-glycidoxybutyltriethoxysilane, γ-glycidoxybutyltrimethoxysilane, γ-glycidoxybutyltriethoxysilane, δ-glycidoxybutyltrimethoxysilane, δ-glycidoxybutyltriethoxysilane, (3,4-epoxycyclohexyl)methyltrimethoxysilane, (3,4-epoxycyclohexyl)methyltriethoxysilane, β-(3,4-epoxycyclohexyl)ethyltrimethoxysilane, β-(3,4-epoxycyclohexyl)ethyltriethoxysilane, β-(3,4-epoxycyclohexyl)ethyltripropoxysilane, β-(3,4-epoxycyclohexyl)ethyltributoxysilane, β-(3,4-epoxycyclohexyl)ethyltriphenoxysilane, γ-(3,4-epoxycyclohexyl)propyltrimethoxysilane, γ-(3,4-epoxycyclohexyl)propyltriethoxysilane, δ-(3,4-epoxycyclohexyl)butyltrimethoxysilane, δ-(3,4-epoxycyclohexyl)butyltriethoxysilane, glycidoxymethylmethyldimethoxysilane, glycidoxymethylmethyldiethoxysilane, α-glycidoxyethylmethyldimethoxysilane, α-glycidoxyethylmethyldiethoxysilane, β-glycidoxyethylmethyldimethoxysilane, β-glycidoxyethylethyldimethoxysilane, α-glycidoxypropylmethyldimethoxysilane, α-glycidoxypropylmethyldiethoxysilane, β-glycidoxypropylmethyldimethoxysilane, β-glycidoxypropylethyldimethoxysilane, γ-glycidoxypropylmethyldimethoxysilane, γ-glycidoxypropylmethyldiethoxysilane, γ-glycidoxypropylmethyldipropoxysilane, γ-glycidoxypropylmethyldibutoxysilane, γ-glycidoxypropylmethyldiphenoxysilane, γ-glycidoxypropylethyldimethoxysilane, γ-glycidoxypropylethyldiethoxysilane, γ-glycidoxypropylvinyldimethoxysilane, γ-glycidoxypropylvinyldiethoxysilane, ethyltrimethoxysilane, ethyltriethoxysilane, vinyltrimethoxysilane, vinyltrichlorosilane, vinyltriacetoxysilane, vinyltriethoxysilane, phenyltrimethoxysilane, phenyltrichlorosilane, phenyltriacetoxysilane, phenyltriethoxysilane, γ-chloropropyltrimethoxysilane, γ-chloropropyltriethoxysilane, γ-chloropropyltriacetoxysilane, 3,3,3-trifluoropropyltrimethoxysilane, γ-methacryloxypropyltrimethoxysilane, γ-mercaptopropyltrimethoxysilane, γ-mercaptopropyltriethoxysilane, β-cyanoethyltriethoxysilane, chloromethyltrimethoxysilane, chloromethyltriethoxysilane, dimethyldimethoxysilane, phenylmethyldimethoxysilane, dimethyldiethoxysilane, phenylmethyldiethoxysilane, γ-chloropropylmethyldimethoxysilane, γ-chloropropylmethyldiethoxysilane, dimethyldiacetoxysilane, γ-methacryloxypropylmethyldimethoxysilane, γ-methacryloxypropylmethyldiethoxysilane, γ-mercaptopropylmethyldimethoxysilane, γ-mercaptomethyldiethoxysilane, methylvinyldimethoxysilane, methylvinyldiethoxysilane, phenylsulfonylaminopropyltriethoxysilane, methylsulfonylaminopropyltriethoxysilane, phenylsulfonylaminopropyltrimethoxysilane, and methylsulfonylaminopropyltrimethoxysilane.

In particular, a combination of a tetraalkoxysilane such as tetramethoxysilane and tetraethoxysilane and a phenyltrialkoxysilane such as phenyltrimethoxysilane and phenyltriethoxysilane is preferred. Such a combination is preferably further combined with an alkyltrialkoxysilane such as methyltrimethoxysilane and methyltriethoxysilane.

The hydrolyzable organosilane (3) can also be exemplified by the structures below. In the structures, $R^2$ is the same as $R^2$ in Formula (3).

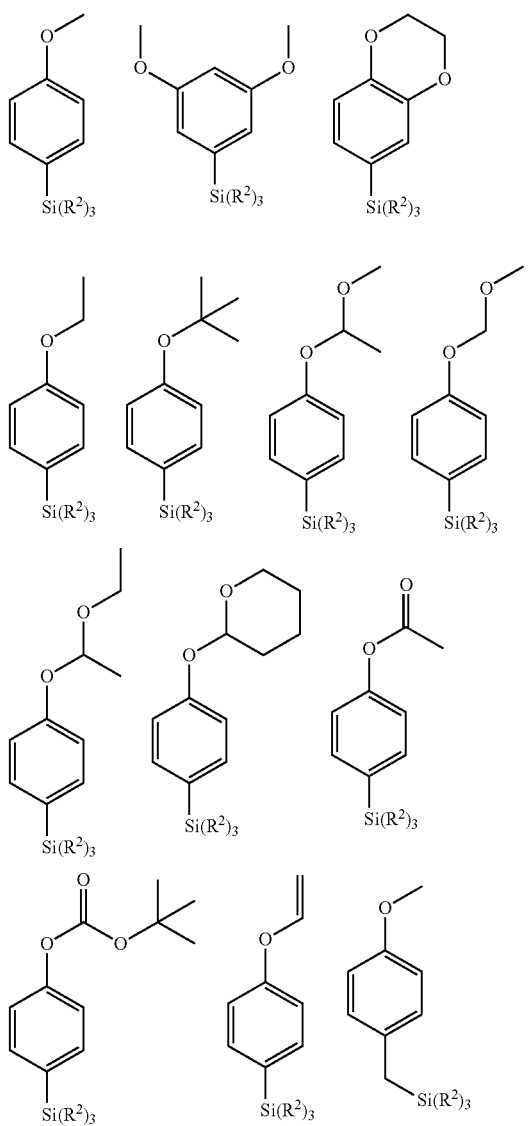

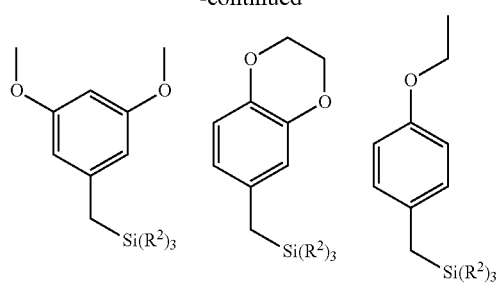
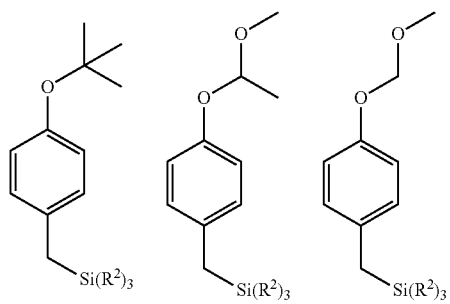
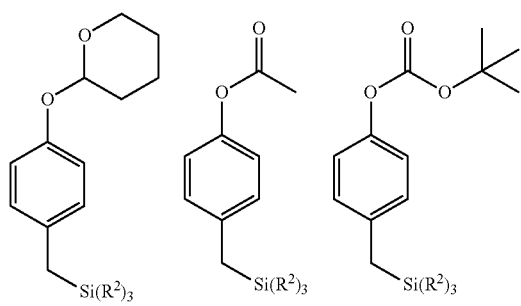
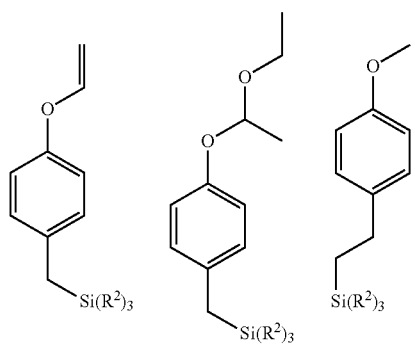
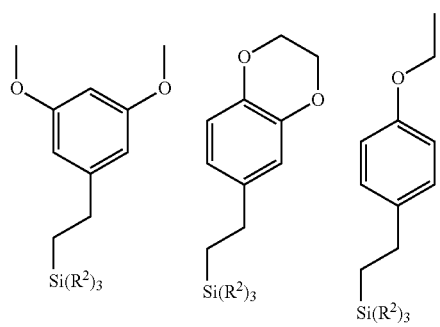
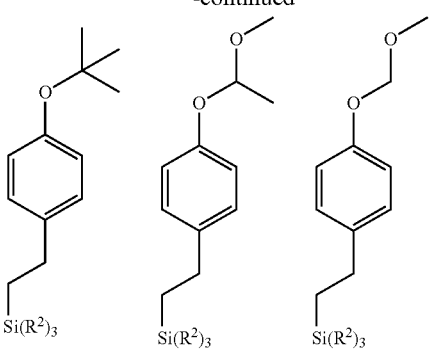
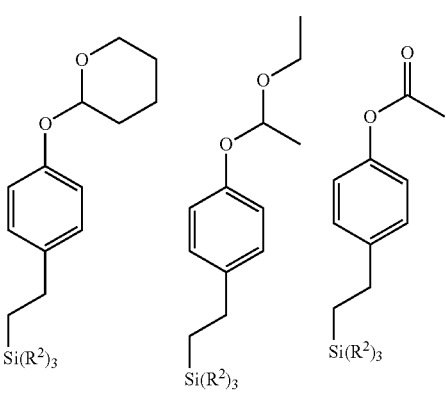
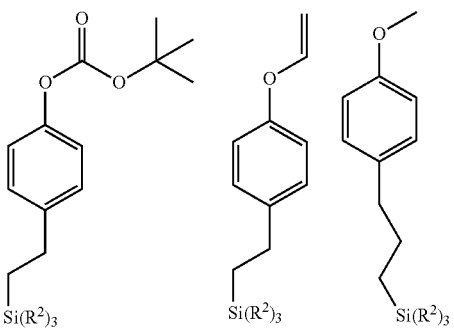
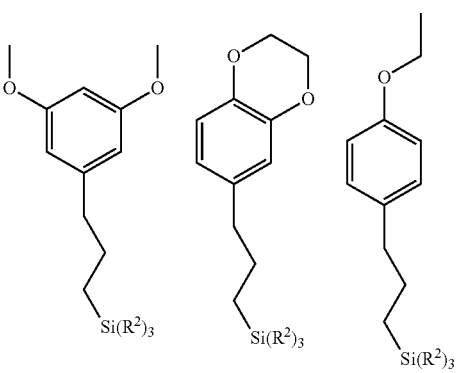

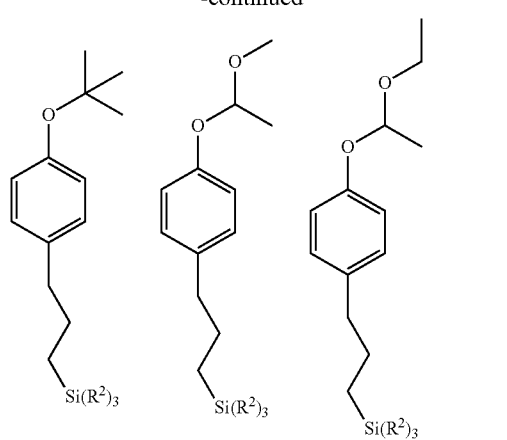
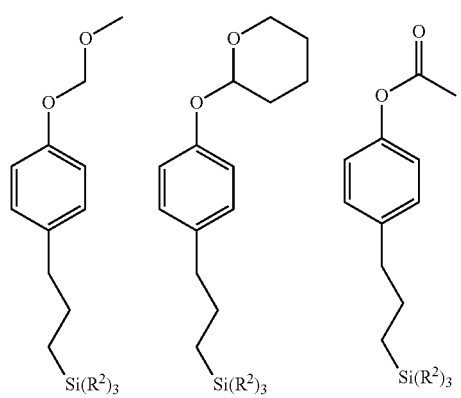
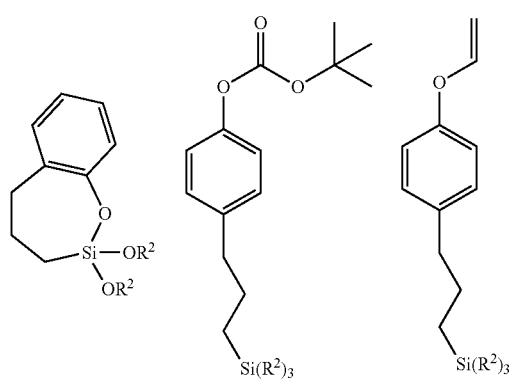
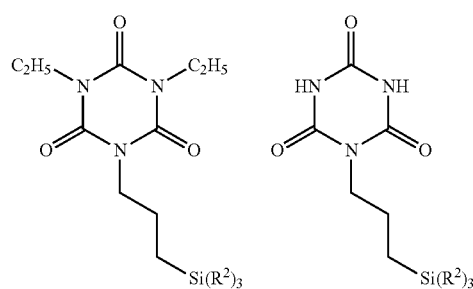
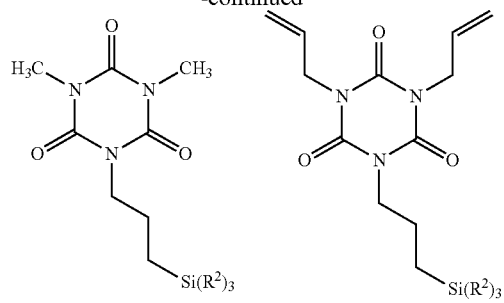
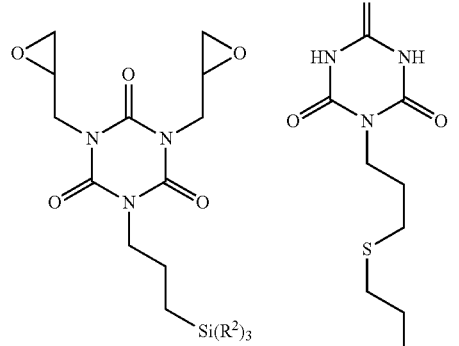
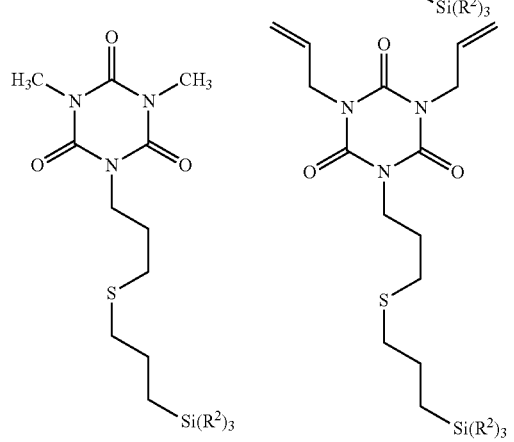
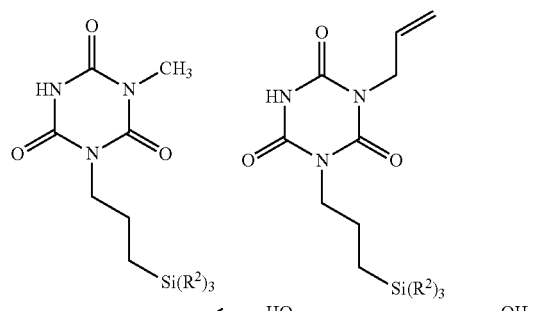
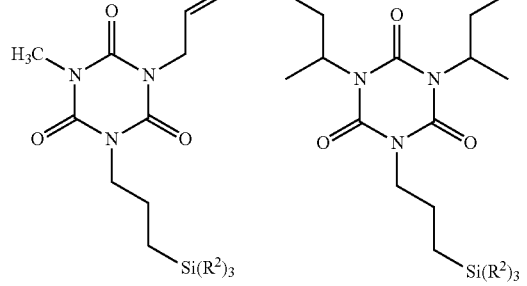

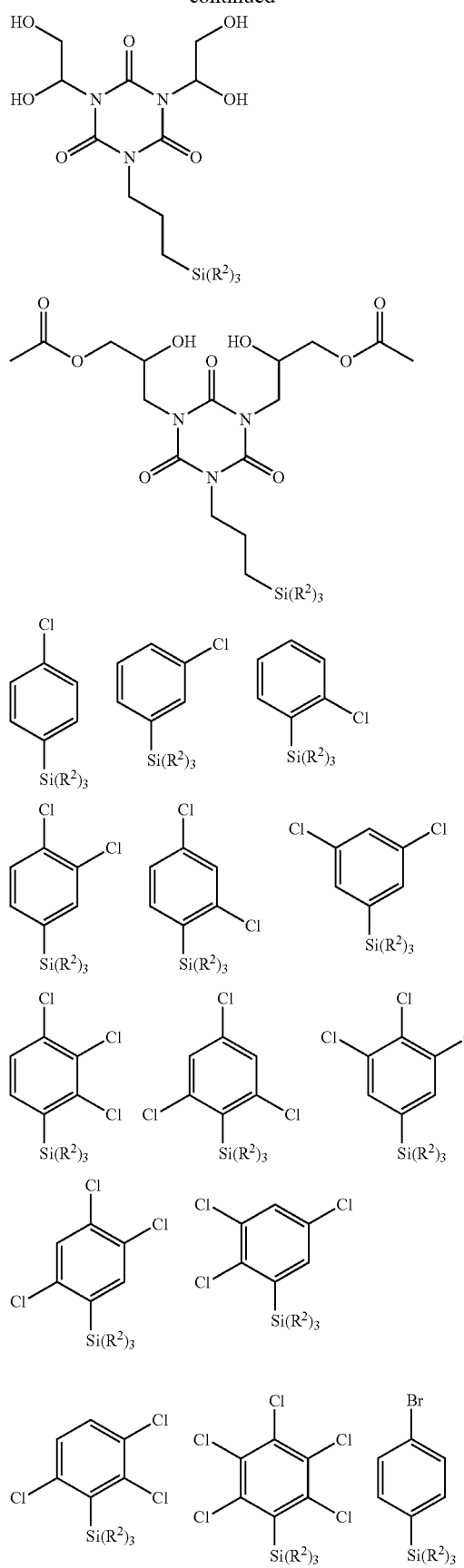
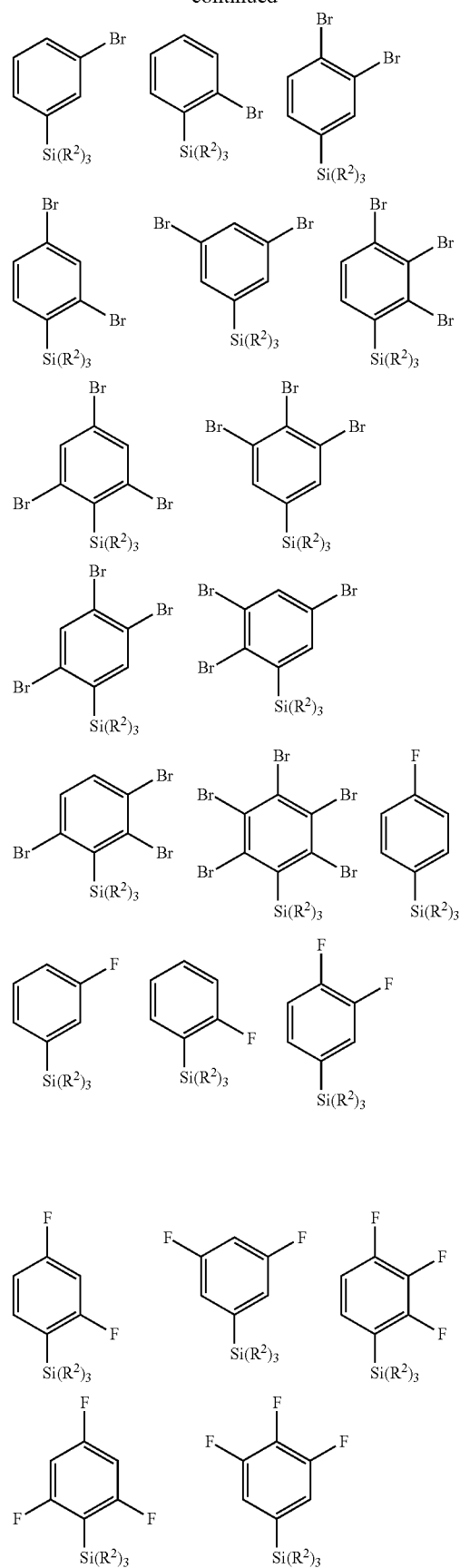

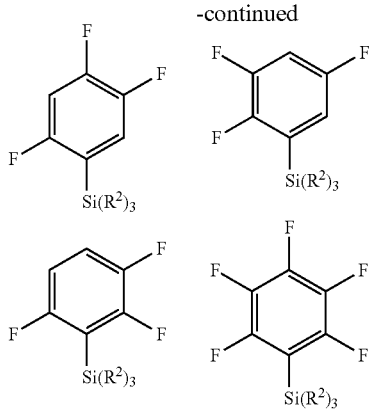

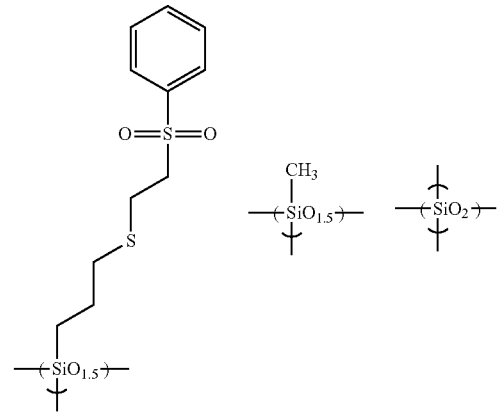

Formula (A-1)

In the hydrolyzable organosilane of Formula (4), $R^1$ is an alkyl group, $R^2$ is an alkoxy group, an acyloxy group, or a halogen group, Y is an alkylene group or an arylene group, b is an integer of 0 or 1, and c is an integer of 0 or 1.

The alkyl group, the alkoxy group, the acyloxy group, or the halogen group may be the groups exemplified in Formula (1). The alkylene group and the arylene group can be exemplified by a divalent organic group corresponding to the alkyl group and the aryl group described above.

Examples of the hydrolyzable organosilane of Formula (4) include methylenebistrimethoxysilane, methylenebistrichlorosilane, methylenebistriacetoxysilane, ethylenebistriethoxysilane, ethylenebistrichlorosilane, ethylenebistriacetoxysilane, propylenebistriethoxysilane, butylenebistrimethoxysilane, phenylenebistrimethoxysilane, phenylenebistriethoxysilane, phenylenebismethyldiethoxysilane, phenylenebismethyldimethoxysilane, naphthylenebistrimethoxysilane, bistrimethoxydisilane, bistriethoxydisilane, bisethyldiethoxydisilane, and bismethyldimethoxydisilane.

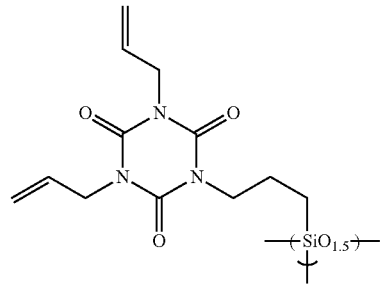

Formula (A-2)

The present invention provides a novel silane compound of Formula (5). In Formula (5), $R^2$ is an alkoxy group, an acyloxy group, or a halogen group. The alkoxy group, the acyloxy group, and the halogen group can be exemplified by the above. a is an integer of 1.

$R^3$ in Formula (5) is represented by Formula (6). In Formula (6), one organic group of the organic groups of $R^4$, $Ar^1$, $R^5$, $Ar^2$, and $R^6$ is bonded to a Si atom through a Si—C bond; $R^4$ is a monovalent to tetravalent hydrocarbon group optionally having a sulfide bond or an ether bond; $R^5$ is a divalent to tetravalent hydrocarbon group optionally having a sulfide bond or an ether bond; $R^6$ is an optionally substituted monovalent to tetravalent hydrocarbon group; each of $Ar^1$ and $Ar^2$ is an optionally substituted phenylene group or phenyl group; $n_2$ is an integer of 1; each of $n_1$, $n_3$, $n_4$, and $n_5$ is an integer of 0 or 1; and $n_4$ and $n_5$ are not simultaneously an integer of 0. The hydrocarbon group and the monovalent to trivalent hydrocarbon group optionally having a sulfide bond or an ether bond can be exemplified by the above.

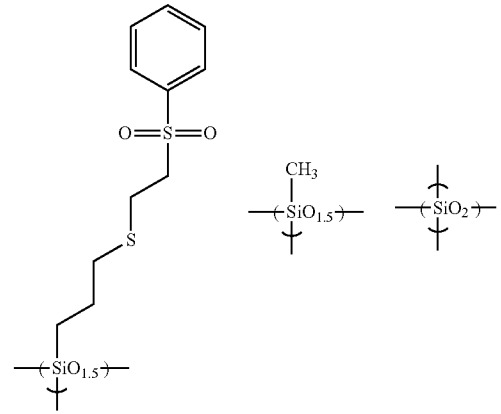

Formula (A-3)

The hydrolysis-condensation product of a hydrolyzable organosilane of Formula (1) and a hydrolyzable organosilane of Formula (3) can be specifically exemplified by the compounds below.

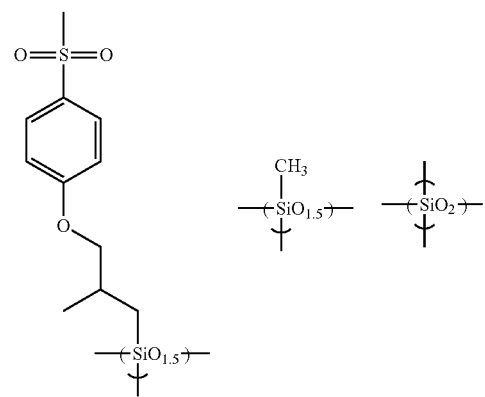

Formula (A-4)
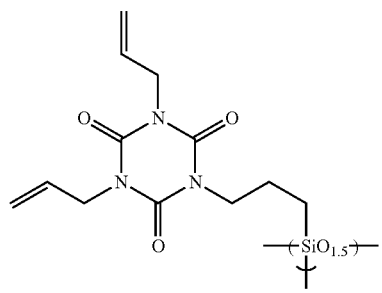
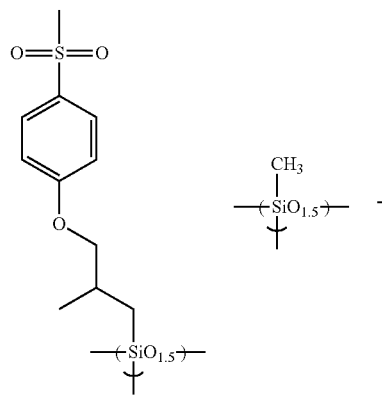
Formula (A-5)
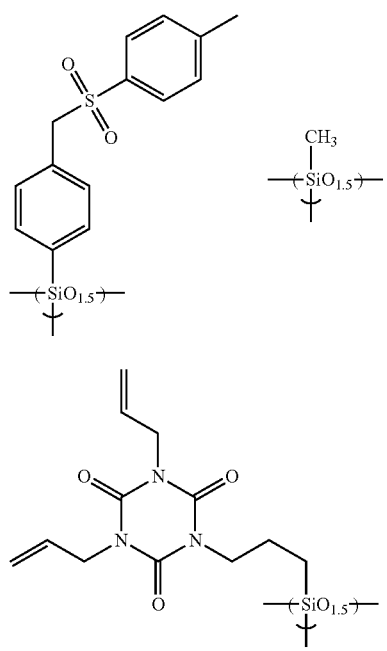
Formula (A-6)
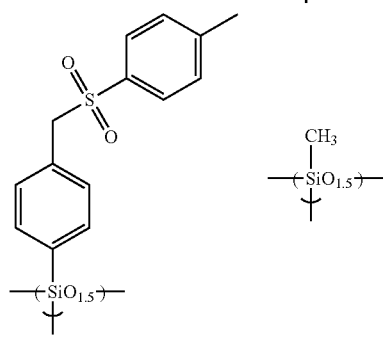
Formula (A-7)
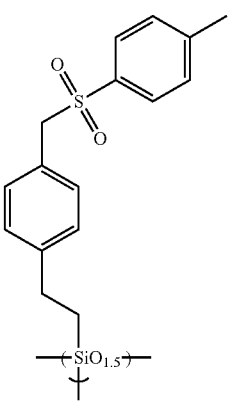
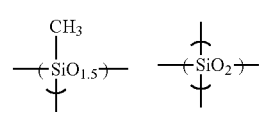
Formula (A-8)
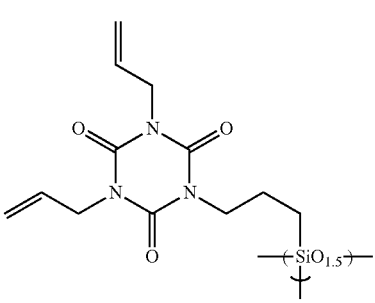
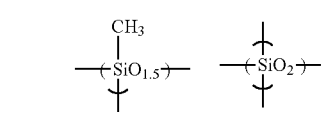
Formula (A-9)

Formula (A-10)
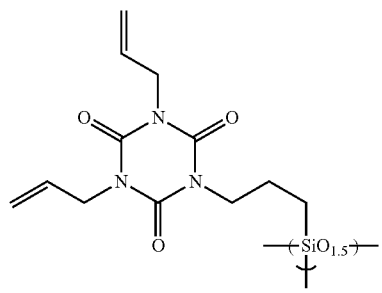
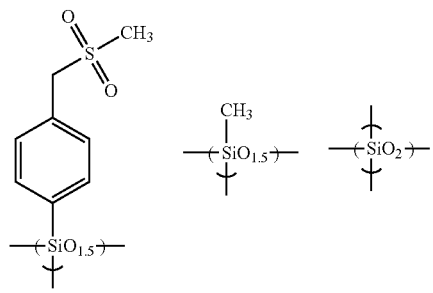
Formula (A-11)
Formula (A-12)
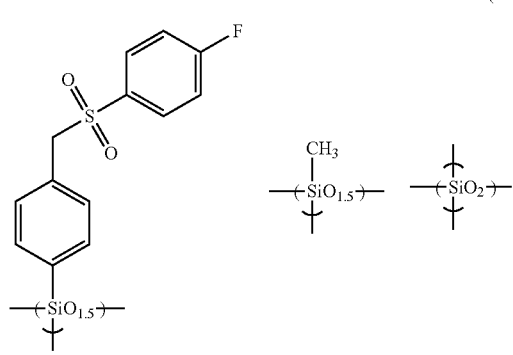
Formula (A-13)
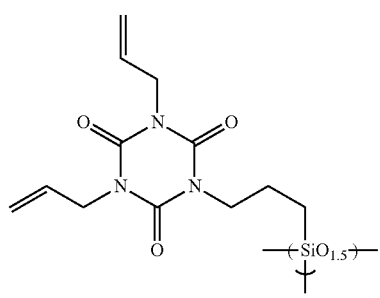
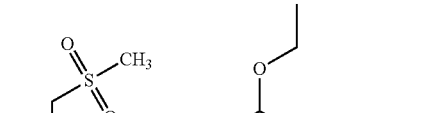
Formula (A-14)
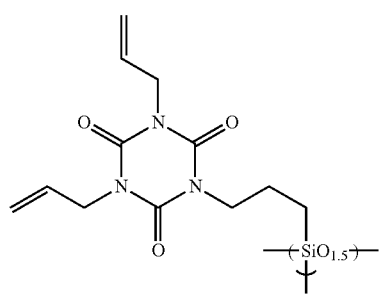
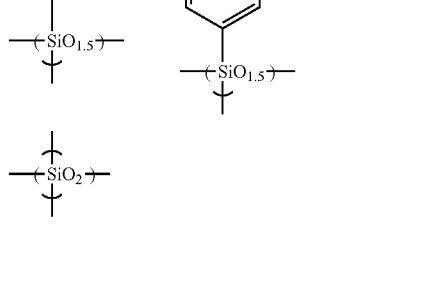
Formula (A-15)
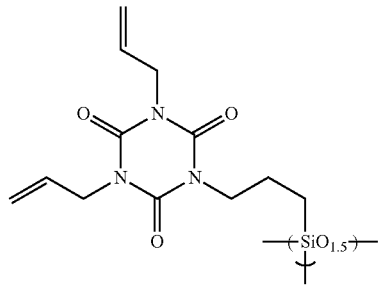

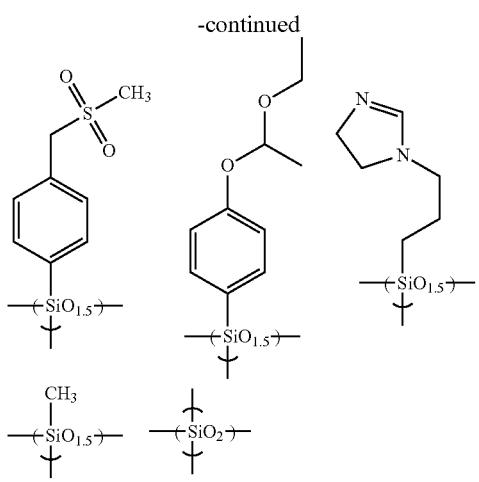

Formula (A-16)

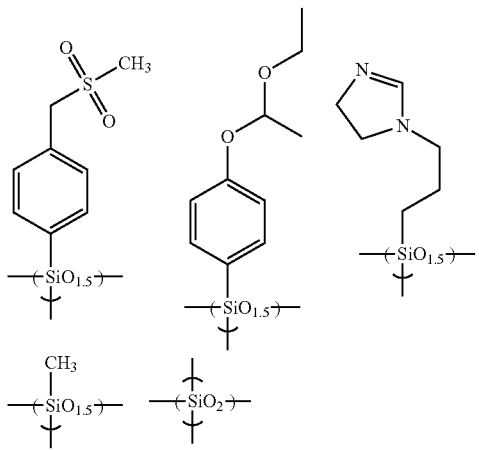

Formula (A-17)

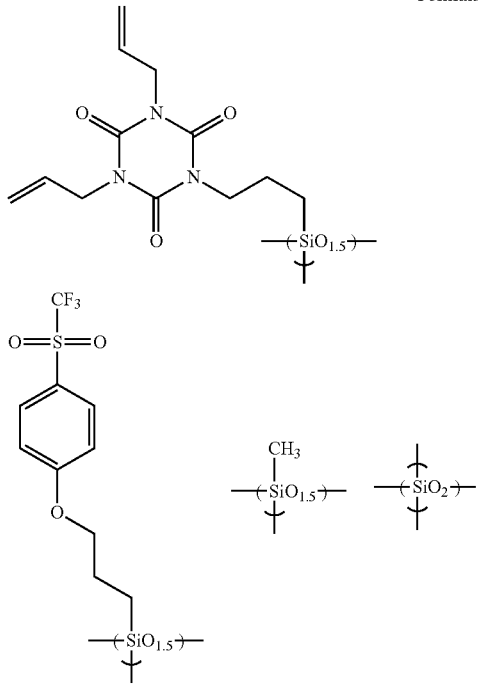

The hydrolysis-condensation product (polyorganosiloxane) of a hydrolyzable organosilane of Formula (1) or the hydrolysis-condensation product (polyorganosiloxane) of a hydrolyzable organosilane of Formula (1) and an organic silicon compound of Formula (3) and/or Formula (4) can yield a condensation product having a weight average molecular weight of 1,000 to 1,000,000 or 1,000 to 100,000. The molecular weight is determined by GPC analysis in terms of polystyrene.

The GPC analysis can be performed, for example, with a GPC apparatus (trade name: HLC-8220GPC, manufactured by Tosoh Corporation) and a GPC column (trade name. Shodex KF803L, KF802, and KF801, manufactured by Showa Denko K. K.) at a column temperature of 40° C. using tetrahydrofuran as an eluent (elution solvent) at a flow rate (flow speed) of 1.0 ml/min and using polystyrene (manufactured by Showa Denko K. K.) as a standard sample.

For the hydrolysis of an alkoxysilyl group, an acyloxysilyl group, or a halogenated silyl group, 0.5 mol to 100 mol, preferably 1 mol to 10 mol of water is used per mole of a hydrolyzable group.

0.001 mol to 10 mol, preferably 0.001 mol to 1 mol of a hydrolysis catalyst can be used per mole of a hydrolyzable group.

The reaction temperature during the hydrolysis and the condensation is typically 20° C. to 80° C.

The hydrolysis may be completely carried out or may be partially carried out. In other words, a hydrolysate and a monomer may remain in a hydrolysis-condensation product.

During the hydrolysis and the condensation, a catalyst may be used.

Examples of the hydrolysis catalyst include a metal chelate compound, an organic acid, an inorganic acid, an organic base, and an inorganic base.

Examples of the metal chelate compound as the hydrolysis catalyst include titanium chelate compounds such as triethoxy•mono(acetylacetonate)titanium, tri-n-propoxy•mono(acetylacetonate)titanium, tri-i-propoxy•mono(acetylacetonate)titanium, tri-n-butoxy•mono(acetylacetonate)titanium, tri-sec-butoxy•mono(acetylacetonate)titanium, tri-t-butoxy•mono(acetylacetonate)titanium, diethoxy•bis(acetylacetonate)titanium, di-n-propoxy•bis(acetylacetonate)titanium, di-i-propoxy•bis(acetylacetonate)titanium, di-n-butoxy•bis(acetylacetonate)titanium, di-sec-butoxy•bis(acetylacetonate)titanium, di-t-butoxy•bis(acetylacetonate)titanium, monoethoxy•tris(acetylacetonate)titanium, mono-n-propoxy•tris(acetylacetonate)titanium, mono-i-propoxy•tris(acetylacetonate)titanium, mono-n-butoxy•tris(acetylacetonate)titanium, mono-sec-butoxy•tris(acetylacetonate)titanium, mono-t-butoxy•tris(acetylacetonate)titanium, tetrakis(acetylacetonate)titanium, triethoxy•mono(ethylacetoacetate)titanium, tri-n-propoxy•mono(ethylacetoacetate)titanium, tri-i-propoxy•mono(ethylacetoacetate)titanium, tri-n-butoxy•mono(ethylacetoacetate)titanium, tri-sec-butoxy•mono(ethylacetoacetate)titanium, tri-t-butoxy•mono(ethylacetoacetate)titanium, diethoxy•bis(ethylacetoacetate)titanium, di-n-propoxy•bis(ethylacetoacetate)titanium, di-i-propoxy•bis(ethylacetoacetate)titanium, di-n-butoxy•bis(ethylacetoacetate)titanium, di-sec-butoxy•bis(ethylacetoacetate)titanium, di-t-butoxy•bis(ethylacetoacetate)titanium, monoethoxy•tris(ethylacetoacetate)titanium, mono-n-propoxy•tris(ethylacetoacetate)titanium, mono-i-propoxy•tris(ethylacetoacetate)titanium, mono-n-butoxy•tris(ethylacetoacetate)titanium, mono-sec-butoxy•tris(ethylacetoacetate)titanium, mono-t-butoxy•tris (ethylacetoacetate)titanium, tetrakis(ethylacetoacetate)titanium, mono(acetylacetonate)tris(ethylacetoacetate)titanium, bis(acetylacetonate)bis(ethylacetoacetate)titanium, and tris(acetylacetonate)mono(ethylacetoacetate)titanium; zirconium chelate compounds such as triethoxy•mono(acetylacetonate)zirconium, tri-n-propoxy•mono(acetylacetonate)zirconium, tri-i-propoxy•mono(acetylacetonate)zirconium, tri-n-butoxy•mono(acetylacetonate)zirconium, tri-sec-butoxy•mono(acetylacetonate)zirconium, tri-t-butoxy•mono(acetylacetonate)zirconium, diethoxy•bis(acetylacetonate)zirconium, di-n-propoxy•bis(acetylacetonate)zirconium, di-i-propoxy•bis(acetylacetonate)zirconium, di-n-butoxy•bis(acetylacetonate)zirconium, di-sec-butoxy•bis(acetylacetonate)zirconium, di-t-butoxy•bis(acetylacetonate)zirconium, monoethoxy•tris(acetylacetonate)zirconium, mono-n-propoxy•tris(acetylacetonate)zirconium, mono-i-propoxy•tris(acetylacetonate)zirconium, mono-n-butoxy•tris(acetylacetonate)zirconium, mono-sec-butoxy•tris(acetylacetonate)zirconium, mono-t-butoxy•tris(acetylacetonate)zirconium, tetrakis(acetylacetonate)zirconium, triethoxy•mono(ethylacetoacetate)zirconium, tri-n-propoxy•mono(ethylacetoacetate)zirconium, tri-i-propoxy•mono(ethylacetoacetate)zirconium, tri-n-butoxy•mono(ethylacetoacetate)zirconium, tri-sec-butoxy•mono(ethylacetoacetate)zirconium, tri-t-butoxy•mono(ethylacetoacetate)zirconium, diethoxy•bis(ethylacetoacetate)zirconium, di-n-propoxy•bis(ethylacetoacetate)zirconium, di-i-propoxy•bis(ethylacetoacetate)zirconium, di-n-butoxy•bis(ethylacetoacetate)zirconium, di-sec-butoxy•bis(ethylacetoacetate)zirconium, di-t-butoxy•bis(ethylacetoacetate)zirconium, monoethoxy•tris(ethylacetoacetate)zirconium, mono-n-propoxy•tris(ethylacetoacetate)zirconium, mono-i-propoxy•tris(ethylacetoacetate)zirconium, mono-n-butoxy•tris(ethylacetoacetate)zirconium, mono-sec-butoxy•tris(ethylacetoacetate)zirconium, mono-t-butoxy•tris(ethylacetoacetate)zirconium, tetrakis(ethylacetoacetate)zirconium, mono(acetylacetonate)tris(ethylacetoacetate)zirconium, bis(acetylacetonate)bis(ethylacetoacetate)zirconium, and tris(acetylacetonate)mono(ethylacetoacetate)zirconium; and aluminum chelate compounds such as tris(acetylacetonate)aluminum and tris(ethylacetoacetate)aluminum.

Examples of the organic acid as the hydrolysis catalyst include acetic acid, propionic acid, butanoic acid, pentanoic acid, hexanoic acid, heptanoic acid, octanoic acid, nonanoic acid, decanoic acid, oxalic acid, maleic acid, methylmalonic acid, adipic acid, sebacic acid, gallic acid, butyric acid, mellitic acid, arachidonic acid, shikimic acid, 2-ethylhexanoic acid, oleic acid, stearic acid, linolic acid, linolenic acid, salicylic acid, benzoic acid, p-aminobenzoic acid, p-toluenesulfonic acid, benzenesulfonic acid, monochloroacetic acid, dichloroacetic acid, trichloroacetic acid, trifluoroacetic acid, formic acid, malonic acid, sulfonic acid, phthalic acid, fumaric acid, citric acid, and tartaric acid.

Examples of the inorganic acid as the hydrolysis catalyst include hydrochloric acid, nitric acid, sulfuric acid, hydrofluoric acid, and phosphoric acid.

Examples of the organic base as the hydrolysis catalyst include pyridine, pyrrole, piperazine, pyrrolidine, piperidine, picoline, trimethylamine, triethylamine, monoethanolamine, diethanolamine, dimethylmonoethanolamine, monomethyldiethanolamine, triethanolamine, diazabicyclooctane, diazabicyclononane, diazabicycloundecene, and tetramethylammonium hydroxide. Examples of the inorganic base include ammonia, sodium hydroxide, potassium hydroxide, barium hydroxide, and calcium hydroxide. Among these catalysts, a metal chelate compound, an organic acid, and an inorganic acid are preferred, and these catalysts may be used singly or in combination of two or more of them.

Examples of the organic solvent used for the hydrolysis include aliphatic hydrocarbon solvents such as n-pentane, i-pentane, n-hexane, i-hexane, n-heptane, i-heptane, 2,2,4-trimethylpentane, n-octane, i-octane, cyclohexane, and methylcyclohexane; aromatic hydrocarbon solvents such as benzene, toluene, xylene, ethylbenzene, trimethylbenzene, methylethylbenzene, n-propylbenzene, i-propylbenzene, diethylbenzene, i-butylbenzene, triethylbenzene, di-i-propylbenzene, n-amylnaphthalene, and trimethylbenzene; monohydric alcoholic solvents such as methanol, ethanol, n-propanol, i-propanol, n-butanol, i-butanol, sec-butanol, t-butanol, n-pentanol, i-pentanol, 2-methylbutanol, sec-pentanol, t-pentanol, 3-methoxybutanol, n-hexanol, 2-methylpentanol, sec-hexanol, 2-ethylbutanol, sec-heptanol, heptanol-3, n-octanol, 2-ethylhexanol, sec-octanol, n-nonyl alcohol, 2,6-dimethylheptanol-4, n-decanol, sec-undecyl alcohol, trimethylnonyl alcohol, sec-tetradecyl alcohol, sec-heptadecyl alcohol, phenol, cyclohexanol, methylcyclohexanol, 3,3,5-trimethylcyclohexanol, benzyl alcohol, phenyl methyl carbinol, diacetone alcohol, and cresol; polyhydric alcohol solvents such as ethylene glycol, propylene glycol, 1,3-butylene glycol, pentanediol-2,4,2-methylpentanediol-2,4, hexanediol-2,5, heptanediol-2,4,2-ethylhexanediol-1,3, diethylene glycol, dipropylene glycol, triethylene glycol, tripropylene glycol, and glycerin; ketone solvents such as acetone, methyl ethyl ketone, methyl n-propyl ketone, methyl n-butyl ketone, diethyl ketone, methyl i-butyl ketone, methyl n-pentyl ketone, ethyl n-butyl ketone, methyl n-hexyl ketone, di-i-butyl ketone, trimethylnonanone, cyclohexanone, methylcyclohexanone, 2,4-pentanedione, acetonylacetone, diacetone alcohol, acetophenone, and fenchone; ether solvents such as ethyl ether, i-propyl ether, n-butyl ether, n-hexyl ether, 2-ethylhexyl ether, ethylene oxide, 1,2-propylene oxide, dioxolane, 4-methyldioxolane, dioxane, dimethyldioxane, ethylene glycol monomethyl ether, ethylene glycol monoethyl ether, ethylene glycol diethyl ether, ethylene glycol mono-n-butyl ether, ethylene glycol mono-n-hexyl ether, ethylene glycol monophenyl ether, ethylene glycol mono-2-ethylbutyl ether, ethylene glycol dibutyl ether, diethylene glycol monomethyl ether, diethylene glycol monoethyl ether, diethylene glycol diethyl ether, diethylene glycol mono-n-butyl ether, diethylene glycol di-n-butyl ether, diethylene glycol mono-n-hexyl ether, ethoxy triglycol, tetraethylene glycol di-n-butyl ether, propylene glycol monomethyl ether, propylene glycol monoethyl ether, propylene glycol monopropyl ether, propylene glycol monobutyl ether, dipropylene glycol monomethyl ether, dipropylene glycol monoethyl ether, dipropylene glycol monopropyl ether, dipropylene glycol monobutyl ether, tripropylene glycol monomethyl ether, tetrahydrofuran, and 2-methyltetrahydrofuran; ester solvents such as diethyl carbonate, methyl acetate, ethyl acetate, γ-butyrolactone, γ-valerolactone, n-propyl acetate, i-propyl acetate, n-butyl acetate, i-butyl acetate, sec-butyl acetate, n-pentyl acetate, sec-pentyl acetate, 3-methoxybutyl acetate, methylpentyl acetate, 2-ethylbutyl acetate, 2-ethylhexyl acetate, benzyl acetate, cyclohexyl acetate, methylcyclohexyl acetate, n-nonyl acetate, methyl acetoacetate, ethyl acetoacetate, ethylene glycol monomethyl ether acetate, ethylene glycol monoethyl ether acetate, diethylene glycol monomethyl ether acetate, diethylene glycol monoethyl ether acetate, diethylene glycol mono-n-butyl ether acetate, propylene glycol monomethyl ether acetate, propylene glycol monoethyl ether acetate, propylene glycol monopropyl ether acetate, propylene glycol monobutyl ether acetate, dipropylene glycol monomethyl ether acetate, dipropylene glycol monoethyl ether acetate, glycol diacetate, methoxytriglycol acetate, ethyl propionate, n-butyl propionate, i-amyl propionate, diethyl oxalate, di-n-butyl oxalate, methyl lactate, ethyl lactate, n-butyl lactate, n-amyl lactate, diethyl malonate, dimethyl phthalate, and diethyl phthalate; nitrogen-containing solvents such as N-methylformamide, N,N-dimethylformamide, N,N-diethylformamide, acetamide, N-methylacetamide, N,N-dimethylacetamide, N-methylpropionamide, and N-methylpyrrolidone; and sulfur-containing solvents such as dimethyl sulfide, diethyl sulfide, thiophene, tetrahydrothiophene, dimethyl sulfoxide, sulfolane, and 1,3-propane sultone. These solvents may be used singly or in combination of two or more of them.

In particular, ketone solvents such as acetone, methyl ethyl ketone, methyl n-propyl ketone, methyl n-butyl ketone, diethyl ketone, methyl i-butyl ketone, methyl n-pentyl ketone, ethyl n-butyl ketone, methyl n-hexyl ketone, di-i-butyl ketone, trimethylnonanone, cyclohexanone, methylcyclohexanone, 2,4-pentanedione, acetonylacetone, diacetone alcohol, acetophenone, and fenchone (1,1,3-trimethyl-2-norbornene) are preferred from the viewpoint of the storage stability of the solution.

The hydrolyzable organosilane can be hydrolyzed and condensed with a catalyst in a solvent, and the obtained hydrolysis-condensation product (polymer) can be subjected to distillation under reduced pressure or other treatments to concurrently remove an alcohol as a by-product, the hydrolysis catalyst used, and water used. An acid or a base catalyst used for the hydrolysis can be removed by neutralization or ion exchange. In the composition for forming a resist underlayer film for lithography of the present invention, the composition for forming a resist underlayer film containing the hydrolysis-condensation product may contain an acid (for example, an organic acid), water, an alcohol, or a combination of them in order to stabilize the composition.

Examples of the organic acid include oxalic acid, malonic acid, methylmalonic acid, succinic acid, maleic acid, malic acid, tartaric acid, phthalic acid, citric acid, glutaric acid, citric acid, lactic acid, and salicylic acid. Among them, for example, oxalic acid and maleic acid are preferred. An organic acid is added in an amount of 0.5 part by mass to 5.0 parts by mass per 100 parts by mass of the condensation product (polyorganosiloxane). Pure water, ultrapure water, and ion-exchanged water can be used as water to be added, and the addition amount thereof is 1 part by mass to 20 parts by mass per 100 parts by mass of the composition for forming a resist underlayer film.

Preferred alcohols to be added are those that are easily passed off with heat after coating, and examples thereof include methanol, ethanol, propanol, isopropanol, and butanol. An alcohol is added in an amount of 1 part by mass to 20 parts by mass per 100 parts by mass of the composition for forming a resist underlayer film.

Bisphenol S or a derivative of bisphenol S may be added as an additive. Bisphenol S or a derivative of bisphenol S is added in an amount of 0.01 part by mass to 20 parts by mass, 0.01 part by mass to 10 parts by mass, or 0.01 part by mass to 5 parts by mass, per 100 parts by mass of the polyorganosiloxane.

A preferred bisphenol S and a preferred derivative of bisphenol S are exemplified by the compounds below.

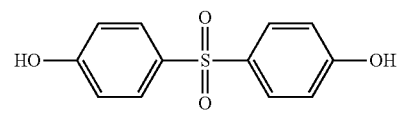

Formula (C-1)

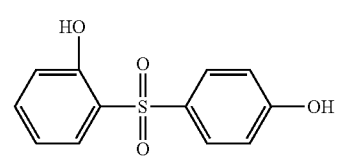

Formula (C-2)

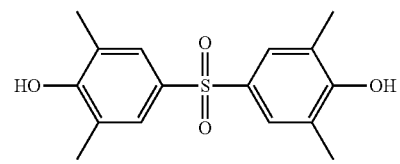

Formula (C-3)

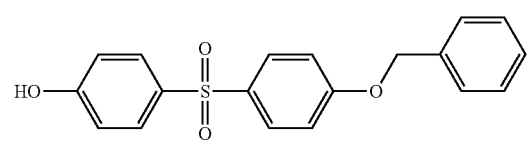

Formula (C-4)

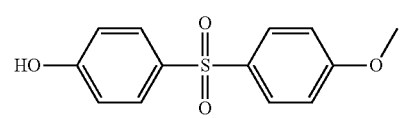

Formula (C-5)

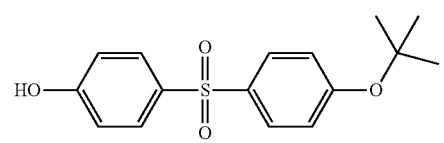

Formula (C-6)

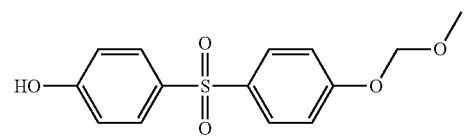

Formula (C-7)

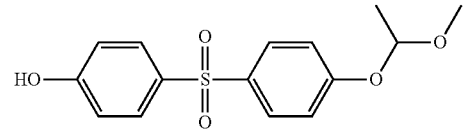

Formula (C-8)

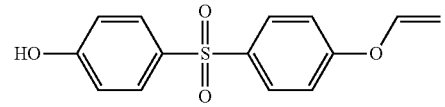

Formula (C-9)

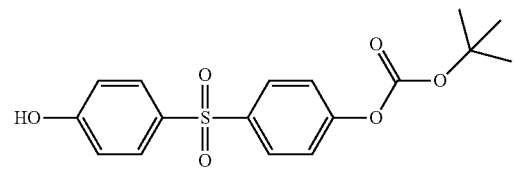

Formula (C-10)

-continued

Formula (C-11)
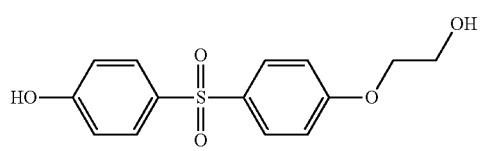

Formula (C-12)
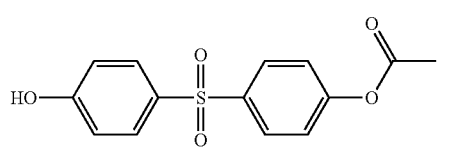

Formula (C-13)
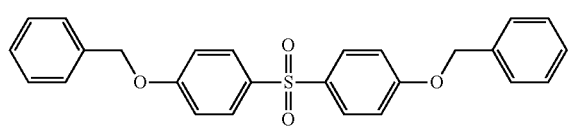

Formula (C-14)
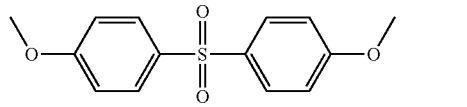

Formula (C-15)
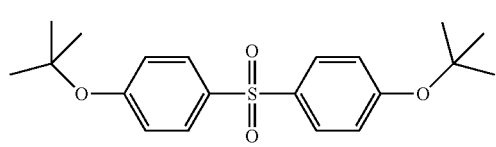

Formula (C-16)
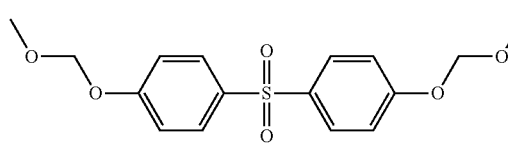

Formula (C-17)
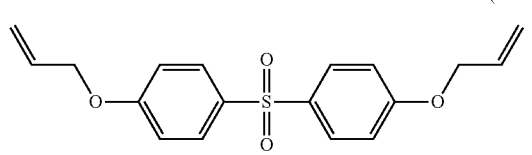

Formula (C-18)
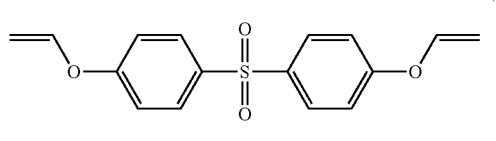

Formula (C-19)
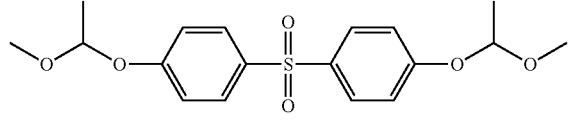

Formula (C-20)

-continued

Formula (C-21)
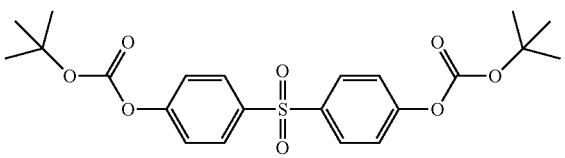

Formula (C-22)
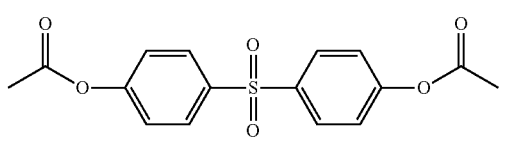

Formula (C-23)
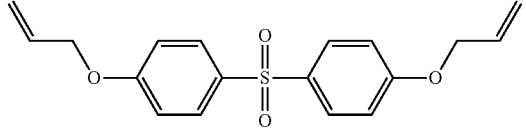

The composition for forming a resist underlayer film of the present invention can contain a curing catalyst. The curing catalyst works as a curing catalyst during heating and curing of the coating film including a polyorganosiloxane containing a hydrolysis-condensation product.

Examples of the usable curing catalyst include ammonium salts, phosphines, phosphonium salts, and sulfonium salts.

Examples of the ammonium salts include a quaternary ammonium salt having the structure of Formula (D-1):

Formula (D-1)
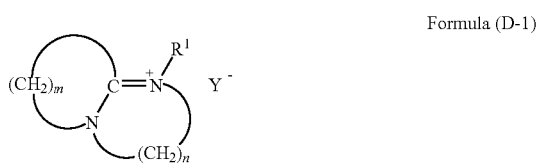

(where m is an integer of 2 to 11; n is an integer of 2 and 3; $R^1$ is an alkyl group or an aryl group; and $Y^-$ is a negative ion), a quaternary ammonium salt having the structure of Formula (D-2):

$$R^2R^3R^4R^5N^+Y^-$$  Formula (D-2)

(where $R^2$, $R^3$, $R^4$, and $R^5$ are an alkyl group or an aryl group; N is a nitrogen atom; $Y^-$ is a negative ion; and each of $R^2$, $R^3$, $R^4$, and $R^5$ is bonded to the nitrogen atom through a C—N bond), a quaternary ammonium salt having the structure of Formula (D-3):

Formula (D-3)

(where $R^6$ and $R^7$ are an alkyl group or an aryl group; and $Y^-$ is a negative ion), a quaternary ammonium salt having the structure of Formula (D-4):

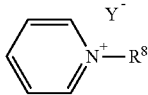

Formula (D-4)

(where $R^8$ is an alkyl group or an aryl group; and $Y^-$ is a negative ion),
a quaternary ammonium salt having the structure of Formula (D-5):

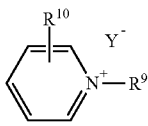

Formula (D-5)

(where $R^9$ and $R^{10}$ are each an alkyl group or an aryl group; and $Y^-$ is a negative ion), and
a tertiary ammonium salt having the structure of Formula (D-6):

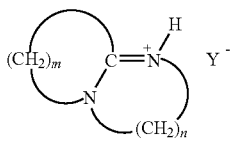

Formula (D-6)

(where m is an integer of 2 to 11; n is an integer of 2 and 3; H is a hydrogen atom; and $Y^-$ is a negative ion).

Examples of the phosphonium salt include a quaternary phosphonium salt of Formula (D-7):

Formula (D-7)

(where $R^{11}$, $R^{12}$, $R^{13}$, and $R^{14}$ are each an alkyl group or an aryl group; P is a phosphorus atom; $Y^-$ is a negative ion; and each of $R^{11}$, $R^{12}$, $R^{13}$, and $R^{14}$ is bonded to the phosphorus atom through a C—P bond).

Examples of the sulfonium salt include a tertiary sulfonium salt of Formula (D-8):

Formula (D-8)

(where $R^{15}$, $R^{16}$, and $R^{17}$ are each an alkyl group or an aryl group; S is a sulfur atom; $Y^-$ is a negative ion; and each of $R^{15}$, $R^{16}$, and $R^{17}$ is bonded to the sulfur atom through a C—S bond).

The compound of Formula (D-1) is a quaternary ammonium salt derived from an amine, m is an integer of 2 to 11, and n is an integer of 2 and 3. In the quaternary ammonium salt, $R^1$ is a $C_{1-18}$, preferably $C_{2-10}$ alkyl group or aryl group, and examples thereof include linear alkyl groups such as an ethyl group, a propyl group, and a butyl group, a benzyl group, a cyclohexyl group, a cyclohexylmethyl group, and a dicyclopentadienyl group. Examples of the negative ion ($Y^-$) include halogen ions such as a chloride ion ($Cl^-$), a bromide ion ($Br^-$), and an iodide ion ($I^-$) and acid groups such as carboxylate (—$COO^-$), sulfonate (—$SO_3^-$), and alcoholate (—$O^-$).

The compound of Formula (D-2) is a quaternary ammonium salt represented by $R^2R^3R^4R^5N^+Y^-$. In the quaternary ammonium salt, $R^2$, $R^3$, $R^4$, and $R^5$ are each a $C_{1-18}$ alkyl group or aryl group or a silane compound bonded to a silicon atom through a Si—C bond. Examples of the negative ion ($Y^-$) include halogen ions such as a chloride ion ($Cl^-$), a bromide ion ($Br^-$), and an iodide ion ($I^-$) and acid groups such as carboxylate (—$COO^-$), sulfonate (—$SO_3^-$), and alcoholate (—$O^-$). The quaternary ammonium salt is commercially available, and examples thereof include tetramethylammonium acetate, tetrabutylammonium acetate, benzyltriethylammonium chloride, benzyltriethylammonium bromide, trioctylmethylammonium chloride, benzyltributylammonium chloride, and benzyltrimethylammonium chloride. These salts can be added as an ammonium compound.

The compound of Formula (D-3) is a quaternary ammonium salt derived from a 1-substituted imidazole, $R^6$ and $R^7$ each have 1 to 18 carbon atoms, and the total number of carbon atoms of $R^6$ and $R^7$ is preferably 7 or more. For example, $R^6$ is a methyl group, an ethyl group, a propyl group, a phenyl group, a benzyl group, a silane compound bonded to a silicon atom through a Si—C bond, or a combination of them. $R^7$ can be exemplified by a benzyl group, an octyl group, and an octadecyl group. Examples of the negative ion ($Y^-$) include halogen ions such as a chloride ion ($Cl^-$), a bromide ion ($Br^-$), and an iodide ion ($I^-$) and acid groups such as carboxylate (—$COO^-$), sulfonate (—$SO_3^-$), and alcoholate (—$O^-$). The compound is commercially available and can be produced by the reaction of, for example, an imidazole compound such as 1-methylimidazole and 1-benzylimidazole with a halogenated alkyl or a halogenated aryl such as benzyl bromide and methyl bromide. The compound of Formula (D-3) may be used as a 4,5-dihydroimidazole compound in which the 4-position and the 5-position are hydrogenated, and examples thereof include N-(3-triethoxysilylpropyl)-4,5-dihydroimidazole. These compounds may be added as a cyclic ammonium compound.

The compound of Formula (D-4) is a quaternary ammonium salt derived from pyridine, $R^8$ is a $C_{1-18}$, preferably $C_{4-18}$ alkyl group or aryl group, and examples thereof include a butyl group, an octyl group, a benzyl group, and a lauryl group. Examples of the negative ion ($Y^-$) include halogen ions such as a chloride ion ($Cl^-$), a bromide ion ($Br^-$), and an iodide ion ($I^-$) and acid groups such as carboxylate (—$COO^-$), sulfonate (—$SO_3^-$), and alcoholate (—$O^-$). The compound is commercially available and can be produced by the reaction of, for example, pyridine with a halogenated alkyl or a halogenated aryl such as lauryl chloride, benzyl chloride, benzyl bromide, methyl bromide, and octyl bromide. Examples of the compound include N-laurylpyridinium chloride and N-benzylpyridinium bromide.

The compound of Formula (D-5) is a quaternary ammonium salt derived from a substituted pyridine typified by picoline. $R^9$ is a $C_{1-18}$, preferably $C_{4-18}$ alkyl group or aryl group, and examples thereof include a methyl group, an octyl group, a lauryl group, and a benzyl group. $R^{10}$ is a $C_{1-18}$ alkyl group or aryl group, and for example, in a quaternary ammonium derived from picoline, $R^{10}$ is a methyl group. Examples of the negative ion ($Y^-$) include halogen ions such as a chloride ion ($Cl^-$), a bromide ion ($Br^-$), and an iodide ion ($I^-$) and acid groups such as carboxylate (—$COO^-$), sulfonate (—$SO_3^-$), and alcoholate (—$O^-$). The compound is commercially available and can be produced by the reaction of, for example, a substituted pyridine such as picoline with a halogenated alkyl or a halogenated aryl such as methyl bromide, octyl bromide, lauryl chloride, benzyl chloride, and benzyl bromide. Examples of the compound include N-benzylpicolinium chloride, N-benzylpicolinium bromide, and N-laurylpicolinium chloride.

The compound of Formula (D-6) is a tertiary ammonium salt derived from an amine, m is an integer of 2 to 11, and n is an integer of 2 and 3. Examples of the negative ion ($Y^-$) include halogen ions such as a chloride ion ($Cl^-$), a bromide ion ($Br^-$), and an iodide ion ($I^-$) and acid groups such as carboxylate ($—COO^-$), sulfonate ($—SO_3^-$), and alcoholate ($—O^-$). The compound can be produced by the reaction of an amine with a weak acid such as a carboxylic acid and phenol. Examples of the carboxylic acid include formic acid and acetic acid. When formic acid is used, the negative ion ($Y^-$) is ($HCOO^-$), and when acetic acid is used, the negative ion ($Y^-$) is ($CH_3COO^-$). When phenol is used, the negative ion ($Y^-$) is ($C_6H_5O^-$).

The compound of Formula (D-7) is a quaternary phosphonium salt having the structure of $R^{11}R^{12}R^{13}R^{14}P^+Y^-$. $R^{11}$, $R^{12}$, $R^{13}$, and $R^{14}$ are each a $C_{1-18}$ alkyl group or aryl group or a silane compound bonded to a silicon atom through a Si—C bond. Three of four substituents of $R^{11}$ to $R^{14}$ are each preferably a phenyl group or a substituted phenyl group, and examples thereof include a phenyl group and a tolyl group. The remaining one substituent is a $C_{1-18}$ alkyl group or aryl group or a silane compound bonded to a silicon atom through a Si—C bond. Examples of the negative ion ($Y^-$) include halogen ions such as a chloride ion ($Cl^-$), a bromide ion ($Br^-$), and an iodide ion ($I^-$) and acid groups such as carboxylate ($—COO^-$), sulfonate ($—SO_3^-$), and alcoholate ($—O^-$). The compound is commercially available, and examples thereof include halogenated tetraalkylphosphoniums such as halogenated tetra-n-butylphosphonium and halogenated tetra-n-propylphosphonium; halogenated trialkylbenzylphosphoniums such as halogenated triethylbenzylphosphonium; halogenated triphenylmonoalkylphosphoniums such as halogenated triphenylmethylphosphonium and halogenated triphenylethylphosphonium; halogenated triphenylbenzylphosphonium; halogenated tetraphenylphosphonium; halogenated tritolylmonoarylphosphoniums; and halogenated tritolylmonoalkylphosphoniums (the halogen atom is a chlorine atom or a bromine atom). Particularly preferred are halogenated triphenylmonoalkylphosphoniums such as halogenated triphenylmethylphosphonium and halogenated triphenylethylphosphonium; halogenated triphenylmonoarylphosphoniums such as halogenated triphenylbenzylphosphonium; halogenated tritolylmonoarylphosphoniums such as halogenated tritolylmonophenylphosphonium; and halogenated tritolylmonoalkylphosphoniums such as halogenated tritolylmonomethylphosphonium (the halogen atom is a chlorine atom or a bromine atom).

Examples of the phosphines include primary phosphines such as methylphosphine, ethylphosphine, propylphosphine, isopropylphosphine, isobutylphosphine, and phenylphosphine; secondary phosphines such as dimethylphosphine, diethylphosphine, diisopropylphosphine, diisoamylphosphine, and diphenylphosphine; and tertiary phosphines such as trimethylphosphine, triethylphosphine, triphenyiphosphine, methyldiphenylphosphine, and dimethylphenylphosphine.

The compound of Formula (D-8) is a tertiary sulfonium salt having the structure of $R^{15}R^{16}R^{17}S^+Y^-$. $R^{15}$, $R^{16}$, and $R^{17}$ are each a $C_{1-18}$ alkyl group or aryl group or a silane compound bonded to a silicon atom through a Si—C bond. Two of three substituents of $R^{15}$ to $R^{17}$ are each preferably a phenyl group or a substituted phenyl group, and examples thereof include a phenyl group and a tolyl group. The remaining one substituent is an optionally substituted $C_{1-18}$ alkyl group or aryl group. Examples of the negative ion ($Y^-$) include halogen ions such as a chloride ion ($Cl^-$), a bromide ion ($Br^-$) and an iodide ion ($I^-$) and acid groups such as carboxylate ($—COO^-$), sulfonate ($—SO_3^-$), and alcoholate ($—O^-$). The compound is commercially available, and examples thereof include halogenated tetraalkylphosphoniums such as halogenated tri-n-butylsulfonium and halogenated tri-n-propylsulfonium; halogenated trialkylbenzylsulfoniums such as halogenated diethylbenzylsulfonium; halogenated diphenylmonoalkylsulfoniums such as halogenated diphenylmethylsulfonium and halogenated diphenylethylsulfonium; halogenated triphenylsulfonium, (the halogen atom is a chlorine atom or a bromine atom); tetraalkylphosphonium carboxylates such as tri-n-butylsulfonium carboxylate and tri-n-propylsulfonium carboxylate; trialkylbenzylsulfonium carboxylates such as diethylbenzylsulfonium carboxylate; diphenylmonoalkylsulfonium carboxylates such as diphenylmethylsulfonium carboxylate and diphenylethylsulfonium carboxylate; triphenylsulfonium carboxylates; and triphenylsulfonium trifluoromethanesulfonates. In particular, halogenated triphenylsulfoniums and triphenylsulfonium carboxylates such as mono-triphenylsulfonium maleate are preferred. These compounds may be added as a sulfonium compound.

The curing catalyst is in an amount of 0.01 part by mass to 10 parts by mass, 0.01 part by mass to 5 parts by mass, or 0.01 part by mass to 3 parts by mass, per 100 parts by mass of the polyorganosiloxane.

The composition for forming an underlayer film for lithography of the present invention may include, in addition to the components mentioned above, an organic polymer compound, a photo acid generator, a surfactant, and other components, as necessary.

The use of an organic polymer compound enables the adjustment of a dry etching rate (the reduction amount of a film thickness per unit time), an attenuation coefficient, a refractive index, and the like of a resist underlayer film formed from the composition for forming an underlayer film for lithography of the present invention.

The organic polymer compound is not particularly limited and various organic polymers can be used. A polycondensation polymer and an addition polymer can be used, for example. Examples of the usable addition polymer and polycondensation polymer include polyester, polystyrene, polyimide, an acrylic polymer, a methacrylic polymer, polyvinyl ether, phenol novolac, naphthol novolac, polyether, polyamide, and polycarbonate. An organic polymer having an aromatic ring structure serving as a light-absorbing moiety, such as a benzene ring, a naphthalene ring, an anthracene ring, a triazine ring, a quinoline ring, and a quinoxaline ring is preferably used.

Examples of such an organic polymer compound include addition polymers containing an addition polymerizable monomer as the structural unit, such as benzyl acrylate, benzyl methacrylate, phenyl acrylate, naphthyl acrylate, anthryl methacrylate, anthrylmethyl methacrylate, styrene, hydroxystyrene, benzyl vinyl ether, and N-phenylmaleimide; and polycondensation polymers such as phenol novolac and naphthol novolac.

An addition polymer used as the organic polymer compound may be a homopolymer or a copolymer. An addition polymerizable monomer is used to produce the addition polymer. Examples of such an addition polymerizable monomer include acrylic acid, methacrylic acid, an acrylic ester compound, a methacrylic ester compound, an acrylamide compound, a methacrylamide compound, a vinyl compound, a styrene compound, a maleimide compound, maleic anhydride, and acrylonitrile.

Examples of the acrylic ester compound include methyl acrylate, ethyl acrylate, n-hexyl acrylate, isopropyl acrylate, cyclohexyl acrylate, benzyl acrylate, phenyl acrylate, anthrylmethyl acrylate, 2-hydroxyethyl acrylate, 3-chloro-2-hydroxypropyl acrylate, 2-hydroxypropyl acrylate, 2,2,2-trifluoroethyl acrylate, 2,2,2-trichloroethyl acrylate, 2-bromoethyl acrylate, 4-hydroxybutyl acrylate, 2-methoxyethyl acrylate, tetrahydrofurfuryl acrylate, 5-acryloyloxy-6-hydroxynorbornene-2-carboxylic-6-lactone, 3-acryloxy propyl triethoxysilane, and glycidyl acrylate.

Examples of the methacrylic ester compound include methyl methacrylate, ethyl methacrylate, n-hexyl methacrylate, isopropyl methacrylate, cyclohexyl methacrylate, benzyl methacrylate, phenyl methacrylate, anthrylmethyl methacrylate, 2-hydroxyethyl methacrylate, 2-hydroxypropyl methacrylate, 2,2,2-trifluoroethyl methacrylate, 2,2,2-trichloroethyl methacrylate, 2-bromoethyl methacrylate, 4-hydroxybutyl methacrylate, 2-methoxyethyl methacrylate, tetrahydrofurfuryl methacrylate, 5-methacryloyloxy-6-hydroxynorbornene-2-carboxylic-6-lactone, 3-methacryloxypropyl triethoxysilane, glycidyl methacrylate, 2-phenylethyl methacrylate, hydroxyphenyl methacrylate, and bromophenyl methacrylate.

Examples of the acrylamide compound include acrylamide, N-methylacrylamide, N-ethylacrylamide, N-benzylacrylamide, N-phenylacrylamide, N,N-dimethylacrylamide, and N-anthryl acrylamide.

Examples of the methacrylamide compound include methacrylamide, N-methylmethacrylamide, N-ethylmethacrylamide, N-benzylmethacrylamide, N-phenylmethacrylamide, N,N-dimethylmethacrylamide, and N-anthrylacrylamide.

Examples of the vinyl compound include vinyl alcohol, 2-hydroxyethyl vinyl ether, methyl vinyl ether, ethyl vinyl ether, benzyl vinyl ether, vinylacetic acid, vinyltrimethoxysilane, 2-chloroethyl vinyl ether, 2-methoxyethyl vinyl ether, vinylnaphthalene, and vinylanthracene.

Examples of the styrene compound include styrene, hydroxystyrene, chlorostyrene, bromostyrene, methoxystyrene, cyanostyrene, and acetylstyrene.

Examples of the maleimide compound include maleimide, N-methylmaleimide, N-phenylmaleimide, N-cyclohexylmaleimide, N-benzylmaleimide, and N-hydroxyethylmaleimide.

Examples of the polycondensation polymer used as the polymer include a polycondensation polymer of a glycol compound and a dicarboxylic acid compound. Examples of the glycol compound include diethylene glycol, hexamethylene glycol, and butylene glycol. Examples of the dicarboxylic acid compound include succinic acid, adipic acid, terephthalic acid, and maleic anhydride. Additional examples include polyesters, polyamides, and polyimides such as polypyromellitimide, poly(p-phenylene terephthalamide), polybutylene terephthalate, and polyethylene terephthalate.

When the organic polymer compound has a hydroxy group, the hydroxy group can cause a cross-linking reaction to the polyorganosiloxane.

The organic polymer compound may be a polymer compound having a weight average molecular weight of, for example, 1,000 to 1,000,000, 3,000 to 300,000, 5,000 to 200,000, or 10,000 to 100,000.

The organic polymer compounds may be used singly or in combination of two or more of them.

The organic polymer compound is, if used, added in a ratio of 1 part by mass to 200 parts by mass, 5 parts by mass to 100 parts by mass, 10 parts by mass to 50 parts by mass, or 20 parts by mass to 30 parts by mass, per 100 parts by mass of the condensation product (polyorganosiloxane).

The composition for forming a resist underlayer film of the present invention may include an acid generator. Examples of the acid generator include a thermal acid generator and a photo acid generator.

The photo acid generator generates acid during the exposure of a resist. This enables the adjustment of the acidity of an underlayer film. This is a method for adjusting the acidity of an underlayer film to the acidity of a resist as the upper layer, and the adjustment of the acidity of the underlayer film enables the adjustment of the pattern shape of the resist to be formed as the upper layer.

Examples of the photo acid generator contained in the composition for forming a resist underlayer film of the present invention include an onium salt compound, a sulfonimide compound, and a disulfonyldiazomethane compound.

Examples of the onium salt compound include iodonium salt compounds such as diphenyliodonium hexafluorophosphate, diphenyliodonium trifluoromethanesulfonate, diphenyliodonium nonafluoro-n-butanesulfonate, diphenyliodonium perfluoro-n-octanesulfonate, diphenyliodonium camphorsulfonate, bis(4-tert-butylphenyl)iodonium camphorsulfonate, and bis(4-tert-butylphenyl)iodonium trifluoromethanesulfonate; and sulfonium salt compounds such as triphenylsulfonium hexafluoroantimonate, triphenylsulfonium nonafluoro-n-butanesulfonate, triphenylsulfonium camphorsulfonate, and triphenylsulfonium trifluoromethanesulfonate.

Examples of the sulfonimide compound include N-(trifluoromethanesulfonyloxy)succinimide, N-(nonafluoro-n-butanesulfonyloxy)succinimide, N-(camphorsulfonyloxy)succinimide, and N-(trifluoromethanesulfonyloxy)naphthalimide.

Examples of the disulfonyldiazomethane compound include bis(trifluoromethylsulfonyl)diazomethane, bis(cyclohexylsulfonyl)diazomethane, bis(phenylsulfonyl)diazomethane, bis(p-toluenesulfonyl)diazomethane, bis(2,4-dimethylbenzenesulfonyl)diazomethane, and methylsulfonyl-p-toluenesulfonyldiazomethane.

The photo acid generators may be used singly or in combination of two or more of them.

A photo acid generator is, if used, contained in a ratio of 0.01 part by mass to 5 parts by mass, 0.1 part by mass to 3 parts by mass, or 0.5 part by mass to 1 part by mass, per 100 parts by mass of the condensation product (polyorganosiloxane).

A surfactant is effective in suppression of pinholes, striations, or the like generated during the application of the composition for forming a resist underlayer film for lithography of the present invention onto a substrate.

Examples of the surfactant contained in the composition for forming a resist underlayer film of the present invention include nonionic surfactants including polyoxyethylene alkyl ethers such as polyoxyethylene lauryl ether, polyoxyethylene stearyl ether, polyoxyethylene cetyl ether, and polyoxyethylene oleyl ether; polyoxyethylene alkylaryl ethers such as polyoxyethylene octylphenol ether and polyoxyethylene nonylphenol ether; polyoxyethylene•polyoxypropylene block copolymers; sorbitan fatty acid esters such as sorbitan monolaurate, sorbitan monopalmitate, sorbitan monostearate, sorbitan monooleate, sorbitan trioleate, and sorbitan tristearate; polyoxyethylene sorbitan fatty acid esters such as polyoxyethylene sorbitan monolaurate, polyoxyethylene sorbitan monopalmitate, polyoxyethylene sorbitan monostearate, polyoxyethylene sorbitan trioleate, and polyoxyethylene sorbitan tristearate; fluorochemical surfactants including trade name EFTOP EF301, EF303, and EF352 (manufactured by Tochem Products), trade name MEGAFAC F171, F173, R-08, and R-30 (manufactured by Dainippon Ink and Chemicals, Inc.), Fluorad FC430 and FC431 (manufactured by Sumitomo 3M), and trade name Asahiguard AG 710, Surflon S-382, SC101, SC102, SC103, SC104, SC105, and SC106 (manufactured by Asahi Glass Co., Ltd.); and organosiloxane polymer KP341 (manufactured by Shin-Etsu Chemical Co., Ltd.). These surfactants may be used alone or in combination of two or more of them. A surfactant is, if used, contained in a ratio of 0.0001 part by mass to 5 parts by mass, 0.001 part by mass to 1 part by mass, or 0.01 part by mass to 0.5 parts by mass, per 100 parts by mass of the condensation product (polyorganosiloxane).

The composition for forming a resist underlayer film of the present invention may also include a rheology control agent and an adhesion assistant. The rheology control agent is effective in improving the flowability of the composition for forming an underlayer film. The adhesion assistant is effective in improving the adhesion of an underlayer film to a semiconductor substrate or a resist.

A solvent used in the composition for forming a resist underlayer film of the present invention may be any solvent that is capable of dissolving the solid contents. Examples of such a solvent include methyl cellosolve acetate, ethyl cellosolve acetate, propylene glycol, propylene glycol monomethyl ether, propylene glycol monoethyl ether, methyl isobutyl carbinol, propylene glycol monobutyl ether, propylene glycol monomethyl ether acetate, propylene glycol monoethyl ether acetate, propylene glycol monopropyl ether acetate, propylene glycol monobutyl ether acetate, toluene, xylene, methyl ethyl ketone, cyclopentanone, cyclohexanone, ethyl 2-hydroxypropionate, ethyl 2-hydroxy-2-methylpropionate, ethyl ethoxyacetate, ethyl hydroxyacetate, methyl 2-hydroxy-3-methylbutanoate, methyl 3-methoxypropionate, ethyl 3-methoxypropionate, ethyl 3-ethoxypropionate, methyl 3-ethoxypropionate, methyl pyruvate, ethyl pyruvate, ethylene glycol monomethyl ether, ethylene glycol monoethyl ether, ethylene glycol monopropyl ether, ethylene glycol monobutyl ether, ethylene glycol monomethyl ether acetate, ethylene glycol monoethyl ether acetate, ethylene glycol monopropyl ether acetate, ethylene glycol monobutyl ether acetate, diethylene glycol dimethyl ether, diethylene glycol diethyl ether, diethylene glycol dipropyl ether, diethylene glycol dibutyl ether, propylene glycol dimethyl ether, propylene glycol diethyl ether, propylene glycol dipropyl ether, propylene glycol dibutyl ether, ethyl lactate, propyl lactate, isopropyl lactate, butyl lactate, isobutyl lactate, methyl formate, ethyl formate, propyl formate, isopropyl formate, butyl formate, isobutyl formate, amyl formate, isoamyl formate, methyl acetate, ethyl acetate, amyl acetate, isoamyl acetate, hexyl acetate, methyl propionate, ethyl propionate, propyl propionate, isopropyl propionate, butyl propionate, isobutyl propionate, methyl butyrate, ethyl butyrate, propyl butyrate, isopropyl butyrate, butyl butyrate, isobutyl butyrate, methyl 3-methoxy-2-methylpropionate, methyl 2-hydroxy-3-methylbutyrate, ethyl methoxyacetate, 3-methoxybutyl acetate, 3-methoxypropyl acetate, 3-methyl-3-methoxybutyl acetate, 3-methyl-3-methoxybutyl propionate, 3-methyl-3-methoxy-butyl butyrate, methyl acetoacetate, methyl propyl ketone, methyl butyl ketone, 2-heptanone, 3-heptanone, 4-heptanone, N,N-dimethylformamide, N-methylacetamide, N,N-dimethylacetamide, N-methylpyrrolidone, 4-methyl-2-pentanol, and γ-butyrolactone. These solvents may be used singly or in combination of two or more of them.

The use of the composition for forming a resist underlayer film of the present invention will be described.

Onto a substrate (for example, a silicon wafer substrate, a silicon/silicon dioxide-coated substrate, a silicon nitride substrate, a glass substrate, an ITO substrate, a polyimide substrate, and a low dielectric constant material-(low-k material-) coated substrate) used for the production of semiconductor devices, the composition for forming a resist underlayer film of the present invention is applied by appropriate coating means such as a spinner and a coater and then is baked to afford a resist underlayer film. The baking condition is appropriately selected from a baking temperature of 80° C. to 250° C. and a baking time of 0.3 minute to 60 minutes. The baking temperature is preferably from 150° C. to 250° C., and the baking time is preferably from 0.5 minute to 2 minutes. The underlayer film formed in this process has a film thickness of, for example, 10 nm to 1,000 nm, 20 nm to 500 nm, 50 nm to 300 nm, or 100 nm to 200 nm.

Next, on the resist underlayer film, a photoresist layer is formed, for example. The photoresist layer can be formed by a well-known method, that is, by applying a solution of a photoresist composition onto the underlayer film and baking the composition. The photoresist has a film thickness of, for example, 50 nm to 10,000 nm, 100 nm to 2,000 nm, or 200 nm to 1,000 nm.

In the present invention, after the formation of an organic underlayer film on a substrate, the resist underlayer film of the present invention can be formed on the organic underlayer film and can be further covered with a photoresist. This enables the fabrication of a substrate by appropriate selection of the etching gas even when a photoresist has a small pattern width and thus has a small thickness in order to prevent the pattern from falling. For example, a fluorine-containing gas that has a sufficiently high etching rate with respect to a photoresist can be used as the etching gas to fabricate the resist underlayer film of the present invention, an oxygen-containing gas that has a sufficiently high etching rate with respect to the resist underlayer film of the present invention can be used as the etching gas to fabricate an organic underlayer film, and a fluorine-containing gas that has a sufficiently high etching rate with respect to the organic underlayer film can be used as the etching gas to fabricate the substrate.

The photoresist formed on the resist underlayer film of the present invention may be any photoresist that is sensitive to light used for exposure. The photoresist may be negative or positive. Examples of the photoresist include a positive photoresist including a novolac resin and a 1,2-naphthoquinone diazide sulfonate ester, a chemically amplified photoresist including a photo acid generator and a binder having a group that is degraded by acid to increase an alkali dissolution rate, a chemically amplified photoresist including a photo acid generator, an alkali soluble binder, and a low molecular compound that is degraded by acid to increase the alkali dissolution rate of a photoresist, and a chemically amplified photoresist including a photo acid generator, a low molecular compound that is degraded by acid to increase the alkali dissolution rate of a photoresist, and a binder having a group that is degraded by acid to increase an alkali dissolution rate. Examples include trade name APEX-E manufactured by Shipley, trade name PAR710 manufactured by Sumitomo Chemical Co., Ltd., and trade name SEPR430 manufactured by Shin-Etsu Chemical Co., Ltd. Additional examples include fluorine atom-containing polymer photoresists as described in Proc. SPIE, Vol. 3999, 330-334 (2000), Proc. SPIE, Vol. 3999, 357-364 (2000), and Proc. SPIE, Vol. 3999, 365-374 (2000).

Next, exposure is performed through a predetermined mask. The exposure may employ a KrF excimer laser (a wavelength of 248 nm), an ArF excimer laser (a wavelength of 193 nm), and a F2 excimer laser (a wavelength of 157 nm), for example. After the exposure, post exposure bake may be carried out, as necessary. The post exposure bake is carried out on conditions that are appropriately selected from a heating temperature of 70° C. to 150° C. and a heating time of 0.3 minute to 10 minutes.

In the present invention, the resist may be a resist for electron beam lithography or a resist for EUV lithography in place of the photoresist. The electron beam resist may be negative or positive. Examples of the resist include a chemically amplified resist including an acid generator and a binder having a group that is degraded by acid to change an alkali dissolution rate, a chemically amplified resist including an alkali soluble binder, an acid generator, and a low molecular compound that is degraded by acid to change the alkali dissolution rate of a resist, a chemically amplified resist including an acid generator, a binder having a group that is degraded by acid to change an alkali dissolution rate, and a low molecular compound that is degraded by acid to change the alkali dissolution rate of a resist, a non-chemically amplified resist including a binder having a group that is degraded by an electron beam to change an alkali dissolution rate, and a non-chemically amplified resist including a binder having a moiety that is cleaved by an electron beam to change an alkali dissolution rate. When such an electron beam resist is used, a resist pattern can be formed using an electron beam as the irradiation source in a similar manner to the case where the photoresist is used. The EUV resist may be a methacrylate resin resist.

Next, development is carried out with a developing solution (for example, an alkali developing solution). For example, when a positive photoresist is used, the development removes an exposed area in the photoresist to form a photoresist pattern.

Examples of the developing solution include aqueous alkaline solutions including aqueous solutions of alkali metal hydroxides such as potassium hydroxide and sodium hydroxide, aqueous solutions of quaternary ammonium hydroxides such as tetramethylammonium hydroxide, tetraethylammonium hydroxide, and choline, and aqueous solutions of amines such as ethanolamine, propylamine, and ethylenediamine. Such a developing solution may further contain a surfactant and other agents. The development conditions are appropriately selected from a temperature of 5° C. to 50° C. and a time of 10 seconds to 600 seconds.

In the present invention, the developing solution may be an organic solvent. After the exposure, the development is carried out with a developing solution (solvent). For example, when a positive photoresist is used, the development removes an unexposed area in the photoresist to form a photoresist pattern.

Examples of the developing solution include methyl acetate, butyl acetate, ethyl acetate, isopropyl acetate, amyl acetate, isoamyl acetate, ethyl methoxyacetate, ethyl ethoxyacetate, propylene glycol monomethyl ether acetate, ethylene glycol monoethyl ether acetate, ethylene glycol monopropyl ether acetate, ethylene glycol monobutyl ether acetate, ethylene glycol monophenyl ether acetate, diethylene glycol monomethyl ether acetate, diethylene glycol monopropyl ether acetate, diethylene glycol monoethyl ether acetate, diethylene glycol monophenyl ether acetate, diethylene glycol monobutyl ether acetate, 2-methoxybutyl acetate, 3-methoxybutyl acetate, 4-methoxybutyl acetate, 3-methyl-3-methoxybutyl acetate, 3-ethyl-3-methoxybutyl acetate, propylene glycol monoethyl ether acetate, propylene glycol monopropyl ether acetate, 2-ethoxybutyl acetate, 4-ethoxybutyl acetate, 4-propoxybutyl acetate, 2-methoxypentyl acetate, 3-methoxypentyl acetate, 4-methoxypentyl acetate, 2-methyl-3-methoxypentyl acetate, 3-methyl-3-methoxypentyl acetate, 3-methyl-4-methoxypentyl acetate, 4-methyl-4-methoxypentyl acetate, propylene glycol diacetate, methyl formate, ethyl formate, butyl formate, propyl formate, ethyl lactate, butyl lactate, propyl lactate, ethyl carbonate, propyl carbonate, butyl carbonate, methyl pyruvate, ethyl pyruvate, propyl pyruvate, butyl pyruvate, methyl acetoacetate, ethyl acetoacetate, methyl propionate, ethyl propionate, propyl propionate, isopropyl propionate, methyl 2-hydroxypropionate, ethyl 2-hydroxypropionate, methyl 3-methoxypropionate, ethyl 3-methoxypropionate, ethyl 3-ethoxypropionate, propyl 3-methoxypropionate, 2-heptanone, 3-heptanone, 4-heptanone, and 4-methyl-2-pentanol. These developing solutions may further contain a surfactant or other agents. The development condition is appropriately selected from a temperature of 5° C. to 50° C. and a time of 10 seconds to 600 seconds.

The resist underlayer film (intermediate layer) of the present invention is removed using the pattern of the photoresist (upper layer) thus formed as a protective film. Next, the organic underlayer film (underlayer) is removed using the patterned film including the photoresist and the resist underlayer film (intermediate layer) of the present invention as a protective film. Finally, a semiconductor substrate is fabricated using the patterned resist underlayer film (intermediate layer) of the present invention and organic underlayer film (underlayer) as a protective film.

First, an area from which the photoresist is removed in the resist underlayer film (intermediate layer) of the present invention is removed by dry etching to expose the semiconductor substrate. The dry etching of the resist underlayer film of the present invention may employ a gas such as tetrafluoromethane ($CF_4$), perfluorocyclobutane ($C_4F_8$), perfluoropropane ($C_3F_8$), trifluoromethane, carbon monoxide, argon, oxygen, nitrogen, sulfur hexafluoride, difluoromethane, nitrogen trifluoride and chlorine trifluoride, chlorine, and trichloroborane and dichloroborane. The dry etching of the resist underlayer film preferably employs a halogen-containing gas. The photoresist essentially composed of an organic substance is not easily removed by dry etching with the halogen-containing gas. In contrast, the resist underlayer film of the present invention containing a large amount of silicon atoms is immediately removed by using the halogen-containing gas. This can suppress the reduction in the film thickness of the photoresist associated with the dry etching of the resist underlayer film. As a result, the photoresist having a small film thickness can be used. The resist underlayer film is preferably dry etched with a fluorine-containing gas, and examples of the fluorine-containing gas include tetrafluoromethane ($CF_4$), perfluorocyclobutane ($C_4F_8$), perfluoropropane ($C_3F_8$), trifluoromethane, and difluoromethane ($CH_2F_2$).

The organic underlayer film is then removed using the patterned film including the photoresist and the resist underlayer film of the present invention as a protective film. The organic underlayer film (underlayer) is preferably dry etched with an oxygen-containing gas. This is because the resist underlayer film of the present invention containing a large amount of silicon atoms is not easily removed by the dry etching with an oxygen-containing gas. Specific examples of the oxygen-containing gas include $O_2$ and $O_3$.

Finally, the semiconductor substrate is fabricated. The semiconductor substrate is preferably fabricated by the dry etching with a fluorine-containing gas.

Examples of the fluorine-containing gas include tetrafluoromethane ($CF_4$), perfluorocyclobutane ($C_4F_8$), perfluoropropane ($C_3F_8$), trifluoromethane, and difluoromethane ($CH_2F_2$).

As the upper layer of the resist underlayer film of the present invention, an organic anti-reflective coating may be formed before the formation of the photoresist. The composition for the anti-reflective coating used at the position is not particularly limited and can be appropriately selected from compositions conventionally used in a lithography process. The anti-reflective coating can be formed by a conventional method, for example, by coating with a spinner or a coater and baking.

A substrate to be coated with the composition for forming a resist underlayer film of the present invention may have an organic or inorganic anti-reflective coating that is formed on the surface of the substrate by a CVD method or other methods, and the underlayer film of the present invention may be formed on the anti-reflective coating.

A resist underlayer film formed from the composition for forming a resist underlayer film of the present invention may absorb light used in a lithography process depending on the wavelength of the light. In such a case, the resist underlayer film can serve as the anti-reflective coating having an effect of preventing light from being reflected from a substrate. The underlayer film of the present invention can also be used as, for example, a layer for preventing the interaction between a substrate and a photoresist, a layer having a function to prevent the adverse effect of a material used in a photoresist or of a substance generated during the exposure to a photoresist on a substrate, a layer having a function to prevent a substance generated from a substrate during heating and baking from diffusing into the upper photoresist, and a barrier layer for reducing a poisoning effect on a photoresist layer due to a semiconductor substrate dielectric layer.

A resist underlayer film formed form the composition for forming a resist underlayer film can be applied to a substrate through which via holes are formed that is used in a dual damascene process and can be used as a filling material capable of thoroughly filling holes. The composition for forming a resist underlayer film can also be used as a planarization material for planarizing the uneven surface of a semiconductor substrate.

The composition for forming a resist underlayer film can also be used as the underlayer film of an EUV resist for the purposes below in addition to the functions as the hard mask. The composition for forming a resist underlayer film can be used as an underlayer anti-reflective coating of the EUV resist, which causes no intermixing with the EUV resist and can prevent the reflection of unfavorable exposed light, for example, the UV or DUV (ArF light, KrF light) described above, from a substrate or an interface during EUV exposure (a wavelength of 13.5 nm). The underlayer of the EUV resist can efficiently prevent the reflection. When the composition for forming a resist underlayer film is used as an EUV resist underlayer film, the process can be performed in a similar manner to that for the photoresist underlayer film.

The present invention will be described in further detail with reference to examples, but the present invention is not limited to them.

EXAMPLES (Synthesis of Compound 1)

Into a 500-ml four-necked flask with a magnetic stirrer, 24.50 g of 2-hydroxyethyl methyl sulfone, 26.20 g of allyl bromide, 29.96 g of potassium carbonate, and 192 g of acetone were charged, and the mixture was stirred under reflux for 12 hours. Acetone was distilled off under reduced pressure, then the residue was diluted with 70 g of ethyl acetate, and the mixture was washed with 50 g of pure water twice. The organic phase was concentrated and dried to afford 14.00 g of Compound 1 (yield: 43%).

$^1$H-NMR (400 MHz), measured in $CDCl_3$ as a solvent: 3.01 ppm (s, 3H), 3.23 ppm (t, J=5.3 Hz, 2H), 3.89 ppm (t, J=5.3 Hz, 2H), 4.03 ppm (dt, J=5.7 Hz, 1.6 Hz, 2H), 5.23 ppm (dq, J=10.4 Hz, 1.6 Hz, 1H), 5.29 ppm (dq, J=17.2 Hz, 1.6 Hz, 1H), 5.88 ppm (ddt, J=17.2 Hz, 10.4 Hz, 5.7 Hz, 1H).

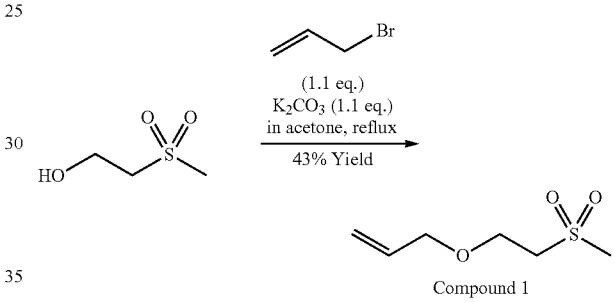

Compound 1

(Synthesis of Compound 2)

Into a 200-ml four-necked flask with a magnetic stirrer, 12.40 g of Compound 1 and 72 g of toluene were charged, and 750 µl of a Karstedt catalyst (a solution of 0.1M platinum(0)-1,3-divinyl-1,1,3,3-tetramethyldisiloxane complex in xylene) and 16.5 ml of triethoxysilane were added. The mixture was then stirred at room temperature for 24 hours. The reaction solution was concentrated and dried, and then the residue was distilled under reduced pressure (outside temperature: 180° C. to 205° C., pressure: 1 torr) to be purified, thus affording 9.90 g of Compound 2 (yield: 59%).

$^1$H-NMR (400 MHz), measured in $CDCl_3$ as a solvent: 0.60 ppm to 0.65 ppm (m, 2H), 1.23 ppm (t, J=7.1 Hz, 9H), 1.65 ppm to 1.74 ppm (m, 2H), 3.00 ppm (s, 3H), 3.21 ppm (t, J=5.3 Hz, 2H), 3.46 ppm (t, J=6.9 Hz, 2H), 3.82 ppm (q, J=7.1 Hz, 6H), 3.86 ppm (t, J=5.3 Hz, 2H).

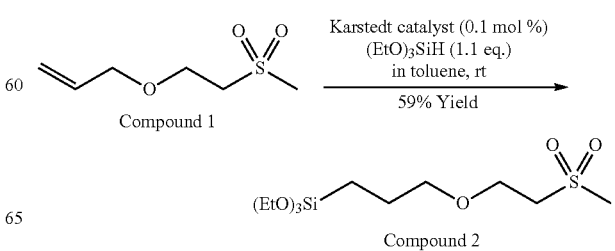

Compound 2

(Synthesis of Compound 3)

Into a 50-ml four-necked flask with a magnetic stirrer, 5.03 g of phenyl vinyl sulfone, 7.13 g of (3-mercaptopropyl)triethoxysilane, 0.30 g of triethylamine, and 30 g of 1,2-dichloroethane were charged, and the mixture was stirred at room temperature for 29 hours. The reaction solution was concentrated and dried to afford 11.84 g of Compound 3 (yield: 97%).

$^1$H-NMR (400 MHz), measured in CDCl$_3$ as a solvent: 0.66 ppm to 0.71 ppm (m, 2H), 1.22 ppm (t, J=7.0 Hz, 9H), 1.60 ppm to 1.70 ppm (m, 2H), 2.51 ppm (t, J=7.2 Hz, 2H), 2.76 ppm to 2.82 ppm (m, 2H), 3.30 ppm to 3.35 ppm (m, 2H), 3.81 ppm (q, J=7.0 Hz, 6H), 7.56 ppm to 7.62 ppm (m, 2H), 7.68 ppm (tt, J=7.4 Hz, 1.2 Hz, 1H), 7.89 ppm to 7.94 ppm (m, 2H).

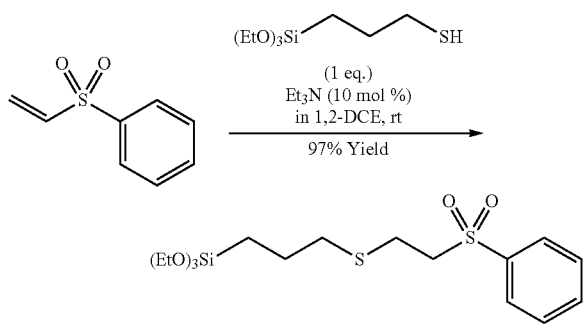

Compound 3

(Synthesis of Compound 4)

Into a 100-ml four-necked flask with a magnetic stirrer, 1.50 g of sodium hydride (purity: 55%) and 5 g of dehydrated THF (tetrahydrofuran) were charged, and a solution of 2.48 g of β-methallyl alcohol dissolved in 10 g of dehydrated THF was added dropwise under ice cooling. Next, a solution of 4-fluorophenyl methyl sulfone dissolved in 30 g of dehydrated THF was added dropwise. The mixture was then stirred at room temperature for 20 hours. The reaction solution was diluted with 100 g of ethyl acetate, and then the mixture was washed with 100 g of pure water twice and washed with 50 g of saturated salt solution once. The organic phase was concentrated and dried to afford 6.50 g of Compound 4 (yield: 100%).

$^1$H-NMR (400 MHz), measured in CDCl$_3$ as a solvent: 1.84 ppm (s, 3H), 3.03 ppm (s, 3H), 4.51 ppm (s, 2H), 5.04 ppm to 5.10 ppm (m, 2H), 7.03 ppm (d, J=9.2 Hz, 2H), 7.85 ppm (d, J=9.2 Hz, 2H).

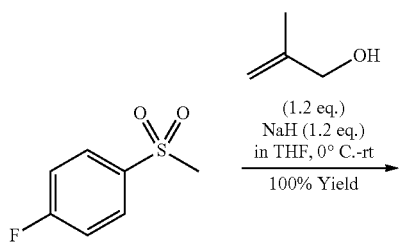

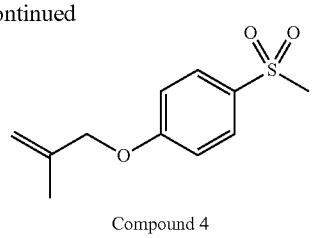

Compound 4

(Synthesis of Compound 5)

Into a 100-ml four-necked flask with a magnetic stirrer, 6.50 g of Compound 4 and 39 g of toluene were charged, and 1,450 µl of a Karstedt catalyst (a solution of 0.1M platinum(0)-1,3-divinyl-1,1,3,3-tetramethyldisiloxane complex in xylene) and 13.6 ml of triethoxysilane were added. The mixture was then stirred at 50° C. for 9 hours. The reaction solution was concentrated and dried, and then the residue was distilled under reduced pressure (outside temperature: 200° C. to 245° C., pressure: 1 torr) to be purified, thus affording 3.03 g of Compound 5 (yield: 27%).

$^1$H-NMR (400 MHz), measured in CDCl$_3$ as a solvent: 0.62 ppm (dd, J=15.3 Hz, 8.2 Hz, 1H), 0.86 ppm (dd, J=15.3 Hz, 5.9 Hz, 1H), 1.12 ppm (d, J=6.7 Hz, 3H), 1.22 ppm (t, J=7.0 Hz, 9H), 2.16 ppm to 2.28 ppm (m, 1H), 3.03 ppm (s, 3H), 3.78 ppm (dd, J=9.0 Hz, 7.0 Hz, 1H), 3.82 ppm (q, J=7.0 Hz, 6H), 3.93 ppm (dd, J=9.2 Hz, 5.7 Hz, 1H), 7.02 ppm (d, J=9.0 Hz, 2H), 7.84 ppm (d, J=9.0 Hz, 2H).

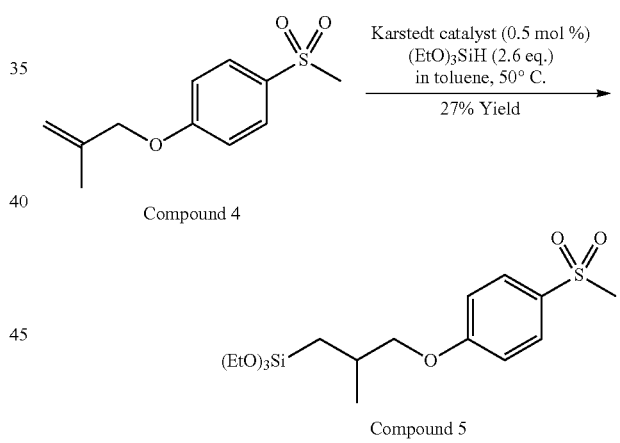

Compound 5

(Synthesis of Compound 6)

Into a 50-ml four-necked flask with a magnetic stirrer, 4.00 g of 4-(chloromethyl)trimethoxysilylbenzene, 2.89 g of sodium p-toluenesulfinate, 16 g of acetonitrile, and 16 g of DMF (dimethylformamide) were charged, and the mixture was stirred at 60° C. for 7 hours. The reaction solution was diluted with 100 g of ethyl acetate, and the mixture was washed with 35 g of pure water twice. Next, the organic phase was dried over sodium sulfate and then was concentrated and dried to afford 5.79 g of Compound 6 (yield: 97%).

$^1$H-NMR (400 MHz), measured in CDCl$_3$ as a solvent: 2.41 ppm (s, 3H), 3.61 ppm (s, 9H), 4.30 ppm (s, 2H), 7.13 ppm (d, J=8.4 Hz, 2H), 7.23 ppm (d, J=8.4 Hz, 2H), 7.50 ppm (d, J=8.4 Hz, 2H), 7.55 ppm (d, J=8.4 Hz, 2H).

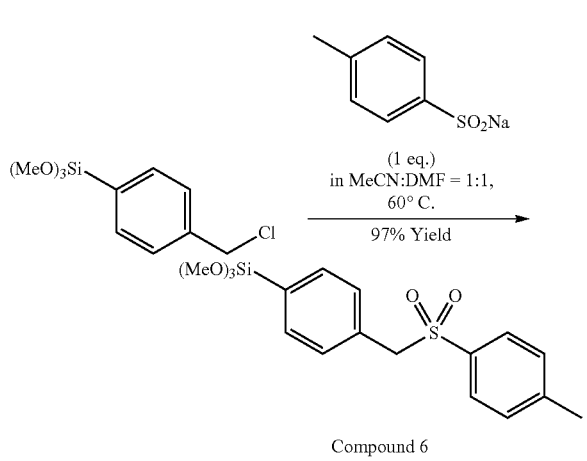

Compound 6

(Synthesis of Compound 7)

Into a 200-ml four-necked flask with a magnetic stirrer, 10.00 g of 4-(chloromethyl)styrene, 12.26 g of sodium p-toluenesulfinate, and 40 g of DMF were charged, and the mixture was stirred at 60° C. for 3 hours. The reaction solution was added to 320 g of pure water, and the precipitated crystal was filtered. The crystal was washed with 48 g of 2-propanol, then filtered, and dried to afford 15.39 g of Compound 7 (yield: 86%).

$^1$H-NMR (400 MHz), measured in CDCl$_3$ as a solvent: 2.42 ppm (s, 3H), 4.28 ppm (s, 2H), 5.28 ppm (d, J=11.0 Hz, 1H), 5.75 ppm (d, J=17.6 Hz, 1H), 6.68 ppm (dd, J=17.6 Hz, 11.0 Hz, 1H), 7.04 ppm (d, J=8.0 Hz, 2H), 7.24 ppm (d, J=8.0 Hz, 2H), 7.30 ppm (d, J=8.0 Hz, 2H), 7.52 ppm (d, J=8.0 Hz, 2H).

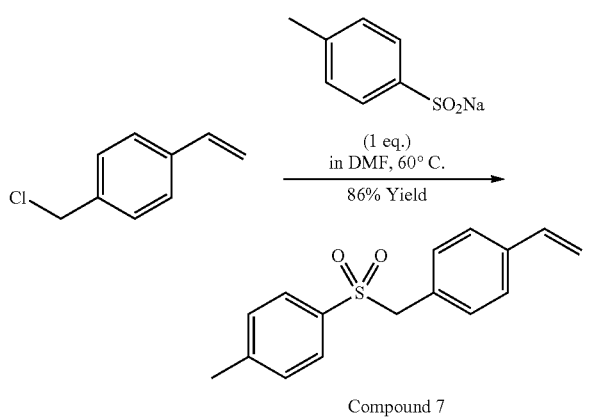

Compound 7

(Synthesis of Compound 8)

Into a 200-ml four-necked flask with a magnetic stirrer, 8.00 g of Compound 7 and 64 g of toluene were charged, and 1,780 μl of a Karstedt catalyst (a solution of 0.1M platinum (0)-1,3-divinyl-1,1,3,3-tetramethyldisiloxane complex in xylene) and 12.1 ml of triethoxysilane were added. The mixture was then stirred at 80° C. for 13 hours. The reaction solution was concentrated and dried, and then the residue was distilled under reduced pressure (outside temperature: 260° C., pressure: 0.8 torr) to be purified, thus affording 4.81 g of Compound 8 (yield: 37%).

$^1$H-NMR (400 MHz), measured in CDCl$_3$ as a solvent: 0.95 ppm (m, 2H), 1.23 ppm (t, J=7.1 Hz, 9H), 2.43 ppm (s, 3H), 2.68 ppm to 2.73 ppm (m, 2H), 3.83 ppm (q, J=7.1 Hz, 6H), 4.25 ppm (s, 2H), 7.00 ppm (d, J=8.0 Hz, 2H), 7.11 ppm (d, J=8.0 Hz, 2H), 7.24 ppm (d, J=8.0 Hz, 2H), 7.52 ppm (s, J=8.0 Hz, 2H).

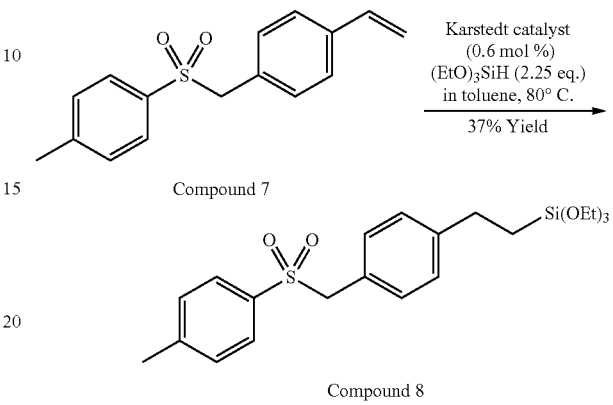

Compound 8

(Synthesis of Compound 9)

Into a 100-ml four-necked flask with a magnetic stirrer, 10.00 g of 4-(chloromethyl)trimethoxysilylbenzene, 4.55 g of sodium methanesulfinate, and 40 g of DMF were charged, and the mixture was stirred at 50° C. for 4 hours. The reaction solution was diluted with 113 g of ethyl acetate, and then the mixture was washed with 60 g of pure water five times. Next, the organic phase was dried over sodium sulfate and then was concentrated and dried to afford 9.61 g of Compound 9 (yield: 82%).

$^1$H-NMR (400 MHz), measured in CDCl$_3$ as a solvent: 2.77 ppm (s, 3H), 3.64 ppm (s, 9H), 4.27 ppm (s, 2H), 7.44 ppm (d, J=8.0 Hz, 2H), 7.69 ppm (d, J=8.0 Hz, 2H).

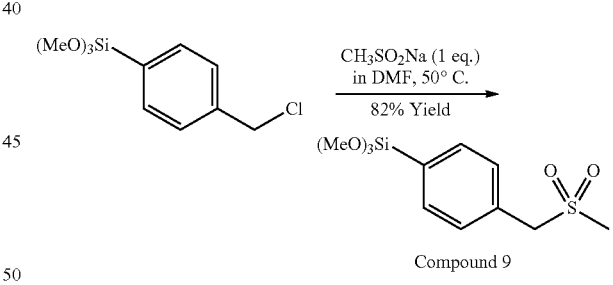

Compound 9

(Synthesis of Compound 10)

Into a 100-ml four-necked flask with a magnetic stirrer, 6.93 g of 4-(chloromethyl)trimethoxysilylbenzene, 5.13 g of sodium 4-fluorobenzenesulfinate, and 20 g of DMF were charged, and the mixture was stirred at 50° C. for 2 hours. The reaction solution was diluted with 200 ml of ethyl acetate, and then the mixture was washed with 100 ml of pure water five times. Next, the organic phase was dried over sodium sulfate and then was concentrated and dried to afford 9.78 g of Compound 10 (yield: 94%).

$^1$H-NMR (400 MHz), measured in CDCl$_3$ as a solvent: 3.62 ppm (s, 9H), 4.32 ppm (s, 2H), 7.07 ppm to 7.15 ppm (m, 4H), 7.56 ppm (d, J=8.2 Hz, 2H), 7.60 ppm to 7.65 ppm (m, 2H).

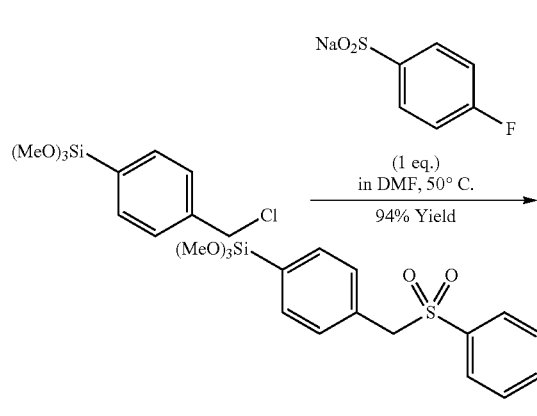

Compound 10

(Synthesis of Compound 11)

Into a 500-ml four-necked flask with a magnetic stirrer, 20.10 g of 4-(trifluoromethylthio)phenol, 72.85 g of sodium periodate, 120 g of 1,2-dichloroethane, 60 g of acetonitrile, and 60 g of pure water were charged, and 1.06 g of ruthenium(III) chloride was added under ice cooling. The mixture was then stirred at room temperature for 22 hours. The reaction solution was diluted with 500 g of ethyl acetate, then the salt was subjected to suction filtration under reduced pressure, and the filtrate was washed with 300 g of pure water twice. The organic phase was dried over 20 g of sodium sulfate and then concentrated and dried to afford 19.97 g of Compound 11 (yield: 85%).

$^1$H-NMR (400 MHz), measured in CDCl$_3$ as a solvent: 7.07 ppm (d, J=8.8 Hz, 2H), 7.92 ppm (d, J=8.8 Hz, 2H).

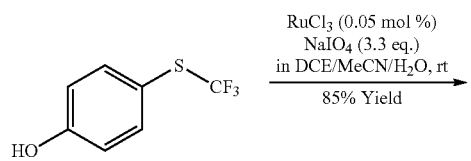

Compound 11

(Synthesis of Compound 12)

Into a 500-ml four-necked flask with a magnetic stirrer, 19.97 g of Compound 11, 16.02 g of allyl bromide, 24.48 g of potassium carbonate, and 40 g of DMF were charged, and the mixture was stirred at 50° C. for 2 hours. The reaction solution was diluted with 500 g of ethyl acetate, then the salt was subjected to suction filtration under reduced pressure, and the filtrate was washed with 200 g of pure water three times and 100 g of saturated salt solution once. The organic phase was concentrated and dried to afford 18.65 g of a crude product of Compound 12. 16.00 g of the crude product was distilled under reduced pressure (temperature: 125° C. to 165° C., pressure: 1 torr) to be purified, thus affording 6.28 g of Compound 12 (yield: 27%).

$^1$H-NMR (400 MHz), measured in CDCl$_3$ as a solvent: 4.67 ppm (dt, J=5.3 Hz, 1.6 Hz, 2H), 5.37 ppm (dq, J=10.6 Hz, 1.6 Hz, 1H), 5.45 ppm (dq, J=17.2 Hz, 1.6 Hz, 1H), 6.04 ppm (ddt, J=17.2 Hz, 10.6 Hz, 5.3 Hz, 1H), 7.12 ppm (d, J=9.0 Hz, 2H), 7.94 ppm (d, J=9.0 Hz, 2H).

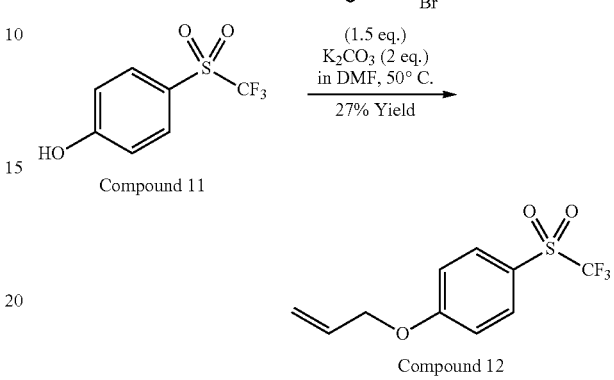

Compound 12

(Synthesis of Compound 13)

Into a 100-ml four-necked flask with a magnetic stirrer, 6.11 g of Compound 12 and 37 g of toluene were charged, and 340 µl of a Karstedt catalyst (a solution of 0.1M platinum(0)-1,3-divinyl-1,1,3,3-tetramethyldisiloxane complex in xylene) and 4.52 g of triethoxysilane were added. The mixture was then stirred at 40° C. for 5 hours. The reaction solution was concentrated and dried, and then the residue was distilled under reduced pressure (outside temperature: 175° C. to 200° C., pressure: 1 torr) to be purified, thus affording 1.06 g of Compound 13 (yield: 11%).

$^1$H-NMR (400 MHz), measured in CDCl$_3$ as a solvent: 0.75 to 0.80 ppm (m, 2H), 1.23 ppm (t, J=7.1 Hz, 9H), 1.91 to 2.00 ppm (m, 2H), 3.83 ppm (q, J=7.1 Hz, 6H), 4.08 ppm (t, J=6.7 Hz, 2H), 7.08 ppm (d, J=8.8 Hz, 2H), 7.93 ppm (d, J=8.8 Hz, 2H).

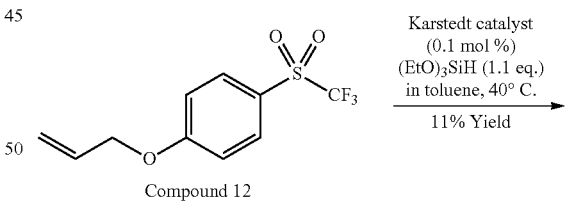

Compound 13

Synthesis Example 1

Into a 300-ml flask, 3.43 g (5% by mol) of triethoxy(3-(2-(phenylsulfonyl)ethylthio)propyl)silane (Compound 3), 24.57 g (70% by mol) of tetraethoxysilane, 7.51 g (25% by mol) of methyltriethoxysilane, and 53.26 g of acetone were charged. To the mixed solution, 11.24 g of 0.01 mol/l hydrochloric acid was added dropwise while the mixed solution was stirred with a magnetic stirrer. After the addition, the flask was transferred into an oil bath adjusted at 85° C., and the mixture was heated and refluxed for 240 minutes to be reacted. Then, the reaction solution was cooled to room temperature. To the reaction solution, 72.00 g of propylene glycol monomethyl ether acetate was added. Ethanol and water as reaction by-products, hydrochloric acid, and acetone were distilled off under reduced pressure to concentrate the reaction solution, thus affording a solution of the hydrolysis-condensation product (polymer) in propylene glycol monomethyl ether acetate. To the solution, propylene glycol monomethyl ether acetate and propylene glycol monoethyl ether were added to be a solvent ratio of propylene glycol monomethyl ether acetate/propylene glycol monoethyl ether of 20/80 and to adjust the concentration to 15 percent by weight in terms of solid residue at 140° C. The obtained polymer corresponds to Formula (A-1) and had a weight average molecular weight Mw of 1,500 in terms of polystyrene by GPC.

Synthesis Example 2

Into a 300-ml flask, 3.32 g (5% by mol) of 3-(triethoxysilylpropyl)diallyl isocyanurate, 3.26 g (5% by mol) of triethoxy(3-(2-(phenylsulfonyl)ethylthio)propyl)silane (Compound 3), 23.41 g (70% by mol) of tetraethoxysilane, 5.72 g (20% by mol) of methyltriethoxysilane, and 53.58 g of acetone were charged. To the mixed solution, 10.70 g of 0.01 mol/l hydrochloric acid was added dropwise while the mixed solution was stirred with a magnetic stirrer. After the addition, the flask was transferred into an oil bath adjusted at 85° C., and the mixture was heated and refluxed for 240 minutes to be reacted. Then, the reaction solution was cooled to room temperature. To the reaction solution, 72.00 g of propylene glycol monomethyl ether acetate was added. Ethanol and water as reaction by-products, hydrochloric acid, and acetone were distilled off under reduced pressure to concentrate the reaction solution, thus affording a solution of the hydrolysis-condensation product (polymer) in propylene glycol monomethyl ether acetate. To the solution, propylene glycol monomethyl ether acetate and propylene glycol monoethyl ether were added to be a solvent ratio of propylene glycol monomethyl ether acetate/propylene glycol monoethyl ether of 20/80 and to adjust the concentration to 15 percent by weight in terms of solid residue at 140° C. The obtained polymer corresponds to Formula (A-2) and had a weight average molecular weight Mw of 1,500 in terms of polystyrene by GPC.

Synthesis Example 3

Into a 300-ml flask, 3.30 g (5% by mol) of triethoxy(2-methyl-3-(4-(methylsulfonyl)phenoxy)propyl)silane (Compound 5), 24.65 g (70% by mol) of tetraethoxysilane, 7.54 g (25% by mol) of methyltriethoxysilane, and 53.24 g of acetone were charged. To the mixed solution, 11.27 g of 0.01 mol/l hydrochloric acid was added dropwise while the mixed solution was stirred with a magnetic stirrer. After the addition, the flask was transferred into an oil bath adjusted at 85° C., and the mixture was heated and refluxed for 240 minutes to be reacted. Then, the reaction solution was cooled to room temperature. To the reaction solution, 72.00 g of propylene glycol monomethyl ether acetate was added. Ethanol and water as reaction by-products, hydrochloric acid, and acetone were distilled off under reduced pressure to concentrate the reaction solution, thus affording a solution of the hydrolysis-condensation product (polymer) in propylene glycol monomethyl ether acetate. To the solution, propylene glycol monomethyl ether acetate and propylene glycol monoethyl ether were added to be a solvent ratio of propylene glycol monomethyl ether acetate/propylene glycol monoethyl ether of 20/80 and to adjust the concentration to 15 percent by weight in terms of solid residue at 140° C. The obtained polymer corresponds to Formula (A-3) and had a weight average molecular weight Mw of 1,500 in terms of polystyrene by GPC.

Synthesis Example 4

Into a 300-ml flask, 3.33 g (5% by mol) of 3-(triethoxysilylpropyl)diallyl isocyanurate, 3.15 g (5% by mol) of triethoxy(2-methyl-3-(4-(methylsulfonyl)phenoxy)propyl)silane (Compound 5), 23.49 g (70% by mol) of tetraethoxysilane, 5.74 g (20% by mol) of methyltriethoxysilane, and 53.56 g of acetone were charged. To the mixed solution, 10.74 g of 0.01 mol/l hydrochloric acid was added dropwise while the mixed solution was stirred with a magnetic stirrer. After the addition, the flask was transferred into an oil bath adjusted at 85° C., and the mixture was heated and refluxed for 240 minutes to be reacted. Then, the reaction solution was cooled to room temperature. To the reaction solution, 72.00 g of propylene glycol monomethyl ether acetate was added. Ethanol and water as reaction by-products, hydrochloric acid, and acetone were distilled off under reduced pressure to concentrate the reaction solution, thus affording a solution of the hydrolysis-condensation product (polymer) in propylene glycol monomethyl ether acetate. To the solution, propylene glycol monomethyl ether acetate and propylene glycol monoethyl ether were added to be a solvent ratio of propylene glycol monomethyl ether acetate/propylene glycol monoethyl ether of 20/80 and to adjust the concentration to 15 percent by weight in terms of solid residue at 140° C. The obtained polymer corresponds to Formula (A-4) and had a weight average molecular weight Mw of 2,200 in terms of polystyrene by GPC.

Synthesis Example 5

Into a 300-ml flask, 3.11 g (5% by mol) of trimethoxy(4-(tosylmethyl)phenyl)silane (Compound 6), 24.78 g (70% by mol) of tetraethoxysilane, 7.57 g (25% by mol) of methyltriethoxysilane, and 53.20 g of acetone were charged. To the mixed solution, 11.33 g of 0.01 mol/l hydrochloric acid was added dropwise while the mixed solution was stirred with a magnetic stirrer. After the addition, the flask was transferred into an oil bath adjusted at 85° C., and the mixture was heated and refluxed for 240 minutes to be reacted. Then, the reaction solution was cooled to room temperature. To the reaction solution, 72.00 g of propylene glycol monomethyl ether acetate was added. Methanol, ethanol, and water as reaction by-products, hydrochloric acid, and acetone were distilled off under reduced pressure to concentrate the reaction solution, thus affording a solution of the hydrolysis-condensation product (polymer) in propylene glycol monomethyl ether acetate. To the solution, propylene glycol monomethyl ether acetate and propylene glycol monoethyl ether were added to be a solvent ratio of propylene glycol monomethyl ether acetate/propylene glycol monoethyl ether of 20/80 and to adjust the concentration to 15 percent by weight in terms of solid residue at 140° C. The obtained polymer corresponds to Formula (A-5) and had a weight average molecular weight Mw of 1,900 in terms of polystyrene by GPC.

Synthesis Example 6

Into a 300-ml flask, 3.35 g (5% by mol) of 3-(triethoxysilylpropyl)diallyl isocyanurate, 2.97 g (5% by mol) of trimethoxy(4-(tosylmethyl)phenyl)silane (Compound 6), 23.60 g (70% by mol) of tetraethoxysilane, 5.77 g (20% by mol) of methyltriethoxysilane, and 53.53 g of acetone were charged. To the mixed solution, 10.79 g of 0.01 mol/l hydrochloric acid was added dropwise while the mixed solution was stirred with a magnetic stirrer. After the addition, the flask was transferred into an oil bath adjusted at 85° C., and the mixture was heated and refluxed for 240 minutes to be reacted. Then, the reaction solution was cooled to room temperature. To the reaction solution, 72.00 g of propylene glycol monomethyl ether acetate was added. Methanol, ethanol, and water as reaction by-products, hydrochloric acid, and acetone were distilled off under reduced pressure to concentrate the reaction solution, thus affording a solution of the hydrolysis-condensation product (polymer) in propylene glycol monomethyl ether acetate. To the solution, propylene glycol monomethyl ether acetate and propylene glycol monoethyl ether were added to be a solvent ratio of propylene glycol monomethyl ether acetate/propylene glycol monoethyl ether of 20/80 and to adjust the concentration to 15 percent by weight in terms of solid residue at 140° C. The obtained polymer corresponds to Formula (A-6) and had a weight average molecular weight Mw of 1,500 in terms of polystyrene by GPC.

Synthesis Example 7

Into a 300-ml flask, 3.66 g (5% by mol) of triethoxy(4-(tosylmethyl)phenethyl)silane (Compound 8), 24.42 g (70% by mol) of tetraethoxysilane, 7.46 g (25% by mol) of methyltriethoxysilane, and 53.30 g of acetone were charged. To the mixed solution, 11.16 g of 0.01 mol/l hydrochloric acid was added dropwise while the mixed solution was stirred with a magnetic stirrer. After the addition, the flask was transferred into an oil bath adjusted at 85° C., and the mixture was heated and refluxed for 240 minutes to be reacted. Then, the reaction solution was cooled to room temperature. To the reaction solution, 72.00 g of propylene glycol monomethyl ether acetate was added. Methanol, ethanol, and water as reaction by-products, hydrochloric acid, and acetone were distilled off under reduced pressure to concentrate the reaction solution, thus affording a solution of the hydrolysis-condensation product (polymer) in propylene glycol monomethyl ether acetate. To the solution, propylene glycol monomethyl ether acetate and propylene glycol monoethyl ether were added to be a solvent ratio of propylene glycol monomethyl ether acetate/propylene glycol monoethyl ether of 20/80 and to adjust the concentration to 15 percent by weight in terms of solid residue at 140° C. The obtained polymer corresponds to Formula (A-7) and had a weight average molecular weight Mw of 1,400 in terms of polystyrene by GPC.

Synthesis Example 8

Into a 300-ml flask, 3.30 g (5% by mol) of 3-(triethoxysilylpropyl)diallyl isocyanurate, 3.48 g (5% by mol) of triethoxy(4-(tosylmethyl)phenethyl)silane (Compound 8), 23.27 g (70% by mol) of tetraethoxysilane, 5.69 g (20% by mol) of methyltriethoxysilane, and 53.62 g of acetone were charged. To the mixed solution, 10.64 g of 0.01 mol/l hydrochloric acid was added dropwise while the mixed solution was stirred with a magnetic stirrer. After the addition, the flask was transferred into an oil bath adjusted at 85° C., and the mixture was heated and refluxed for 240 minutes to be reacted. Then, the reaction solution was cooled to room temperature. To the reaction solution, 72.00 g of propylene glycol monomethyl ether acetate was added. Methanol, ethanol, and water as reaction by-products, hydrochloric acid, and acetone were distilled off under reduced pressure to concentrate the reaction solution, thus affording a solution of the hydrolysis-condensation product (polymer) in propylene glycol monomethyl ether acetate. To the solution, propylene glycol monomethyl ether acetate and propylene glycol monoethyl ether were added to be a solvent ratio of propylene glycol monomethyl ether acetate/propylene glycol monoethyl ether of 20/80 and to adjust the concentration to 15 percent by weight in terms of solid residue at 140° C. The obtained polymer corresponds to Formula (A-8) and had a weight average molecular weight Mw of 1,500 in terms of polystyrene by GPC.

Synthesis Example 9

Into a 300-ml flask, 2.51 g (5% by mol) of 4-(methylsulfonylmethyl)phenyltrimethoxysilane (Compound 9), 25.19 g (70% by mol) of tetraethoxysilane, 7.70 g (25% by mol) of methyltriethoxysilane, and 53.09 g of acetone were charged. To the mixed solution, 11.52 g of 0.01 mol/l hydrochloric acid was added dropwise while the mixed solution was stirred with a magnetic stirrer. After the addition, the flask was transferred into an oil bath adjusted at 85° C., and the mixture was heated and refluxed for 240 minutes to be reacted. Then, the reaction solution was cooled to room temperature. To the reaction solution, 72.00 g of propylene glycol monomethyl ether acetate was added. Methanol, ethanol, and water as reaction by-products, hydrochloric acid, and acetone were distilled off under reduced pressure to concentrate the reaction solution, thus affording a solution of the hydrolysis-condensation product (polymer) in propylene glycol monomethyl ether acetate. To the solution, propylene glycol monomethyl ether acetate and propylene glycol monoethyl ether were added to be a solvent ratio of propylene glycol monomethyl ether acetate/propylene glycol monoethyl ether of 20/80 and to adjust the concentration to 15 percent by weight in terms of solid residue at 140° C. The obtained polymer corresponds to Formula (A-9) and had a weight average molecular weight Mw of 3,000 in terms of polystyrene by GPC.

Synthesis Example 10

Into a 300-ml flask, 3.40 g (5% by mol) of 3-(triethoxysilylpropyl)diallyl isocyanurate, 2.39 g (5% by mol) of 4-(methylsulfonylmethyl)phenyltrimethoxysilane (Compound 9), 23.97 g (70% by mol) of tetraethoxysilane, 5.86 g (20% by mol) of methyltriethoxysilane, and 53.42 g of acetone were charged. To the mixed solution, 10.96 g of 0.01 mol/l hydrochloric acid was added dropwise while the mixed solution was stirred with a magnetic stirrer. After the addition, the flask was transferred into an oil bath adjusted at 85° C., and the mixture was heated and refluxed for 240 minutes to be reacted. Then, the reaction solution was cooled to room temperature. To the reaction solution, 72.00 g of propylene glycol monomethyl ether acetate was added. Methanol, ethanol, and water as reaction by-products, hydrochloric acid, and acetone were distilled off under reduced pressure to concentrate the reaction solution, thus affording a solution of the hydrolysis-condensation product (polymer) in propylene glycol monomethyl ether acetate. To the solution, propylene glycol monomethyl ether acetate and propylene glycol monoethyl ether were added to be a solvent ratio of propylene glycol monomethyl ether acetate/propylene glycol monoethyl ether of 20/80 and to adjust the concentration to 15 percent by weight in terms of solid residue at 140° C. The obtained polymer corresponds to Formula (A-10) and had a weight average molecular weight Mw of 2,500 in terms of polystyrene by GPC.

Synthesis Example 11

Into a 300-ml flask, 3.14 g (5% by mol) of 4-((p-fluorophenylsulfonyl)methyl)phenyltrimethoxysilane (Compound 10), 24.76 g (70% by mol) of tetraethoxysilane, 7.57 g (25% by mol) of methyltriethoxysilane, and 53.21 g of acetone were charged. To the mixed solution, 11.32 g of 0.01 mol/l hydrochloric acid was added dropwise while the mixed solution was stirred with a magnetic stirrer. After the addition, the flask was transferred into an oil bath adjusted at 85° C., and the mixture was heated and refluxed for 240 minutes to be reacted. Then, the reaction solution was cooled to room temperature. To the reaction solution, 72.00 g of propylene glycol monomethyl ether acetate was added. Methanol, ethanol, and water as reaction by-products, hydrochloric acid, and acetone were distilled off under reduced pressure to concentrate the reaction solution, thus affording a solution of the hydrolysis-condensation product (polymer) in propylene glycol monomethyl ether acetate. To the solution, propylene glycol monomethyl ether acetate and propylene glycol monoethyl ether were added to be a solvent ratio of propylene glycol monomethyl ether acetate/propylene glycol monoethyl ether of 20/80 and to adjust the concentration to 15 percent by weight in terms of solid residue at 140° C. The obtained polymer corresponds to Formula (A-11) and had a weight average molecular weight Mw of 2,400 in terms of polystyrene by GPC.

Synthesis Example 12

Into a 300-ml flask, 3.34 g (5% by mol) of 3-(triethoxysilylpropyl)diallyl isocyanurate, 3.00 g (5% by mol) of 4-((p-fluorophenylsulfonyl)methyl)phenyltrimethoxysilane (Compound 10), 23.58 g (70% by mol) of tetraethoxysilane, 5.77 g (20% by mol) of methyltriethoxysilane, and 53.53 g of acetone were charged. To the mixed solution, 10.78 g of 0.01 mol/l hydrochloric acid was added dropwise while the mixed solution was stirred with a magnetic stirrer. After the addition, the flask was transferred into an oil bath adjusted at 85° C., and the mixture was heated and refluxed for 240 minutes to be reacted. Then, the reaction solution was cooled to room temperature. To the reaction solution, 72.00 g of propylene glycol monomethyl ether acetate was added. Methanol, ethanol, and water as reaction by-products, hydrochloric acid, and acetone were distilled off under reduced pressure to concentrate the reaction solution, thus affording a solution of the hydrolysis-condensation product (polymer) in propylene glycol monomethyl ether acetate. To the solution, propylene glycol monomethyl ether acetate and propylene glycol monoethyl ether were added to be a solvent ratio of propylene glycol monomethyl ether acetate/propylene glycol monoethyl ether of 20/80 and to adjust the concentration to 15 percent by weight in terms of solid residue at 140° C. The obtained polymer corresponds to Formula (A-12) and had a weight average molecular weight Mw of 2,000 in terms of polystyrene by GPC.

Synthesis Example 13

Into a 300-ml flask, 3.30 g (5% by mol) of 3-(triethoxysilylpropyl)diallyl isocyanurate, 2.32 g (5% by mol) of 4-(methylsulfonylmethyl)phenyltrimethoxysilane (Compound 9), 24.94 g (75% by mol) of tetraethoxysilane, 2.85 g (10% by mol) of methyltriethoxysilane, 2.29 g (5% by mol) of (4-(1-ethoxyethoxy)phenyl)trimethoxysilane, and 53.53 g of acetone were charged. To the mixed solution, 10.79 g of 0.01 mol/l hydrochloric acid was added dropwise while the mixed solution was stirred with a magnetic stirrer. After the addition, the flask was transferred into an oil bath adjusted at 85° C., and the mixture was heated and refluxed for 240 minutes to be reacted. Then, the reaction solution was cooled to room temperature. To the reaction solution, 72.00 g of propylene glycol monomethyl ether acetate was added. Methanol, ethanol, and water as reaction by-products, hydrochloric acid, and acetone were distilled off under reduced pressure to concentrate the reaction solution, thus affording a solution of the hydrolysis-condensation product (polymer) in propylene glycol monomethyl ether acetate. To the solution, propylene glycol monomethyl ether acetate and propylene glycol monoethyl ether were added to be a solvent ratio of propylene glycol monomethyl ether acetate/propylene glycol monoethyl ether of 20/80 and to adjust the concentration to 15 percent by weight in terms of solid residue at 140° C. The obtained polymer corresponds to Formula (A-13) and had a weight average molecular weight Mw of 2,500 in terms of polystyrene by GPC.

Synthesis Example 14

Into a 300-ml flask, 2.43 g (5% by mol) of 4-(methylsulfonylmethyl)phenyltrimethoxysilane (Compound 9), 26.17 g (75% by mol) of tetraethoxysilane, 4.48 g (15% by mol) of methyltriethoxysilane, 2.40 g (5% by mol) of (4-(1-ethoxyethoxy)phenyl)trimethoxysilane, and 53.21 g of acetone were charged. To the mixed solution, 11.32 g of 0.01 mol/l hydrochloric acid was added dropwise while the mixed solution was stirred with a magnetic stirrer. After the addition, the flask was transferred into an oil bath adjusted at 85° C., and the mixture was heated and refluxed for 240 minutes to be reacted. Then, the reaction solution was cooled to room temperature. To the reaction solution, 72.00 g of propylene glycol monomethyl ether acetate was added. Methanol, ethanol, and water as reaction by-products, hydrochloric acid, and acetone were distilled off under reduced pressure to concentrate the reaction solution, thus affording a solution of the hydrolysis-condensation product (polymer) in propylene glycol monomethyl ether acetate. To the solution, propylene glycol monomethyl ether acetate and propylene glycol monoethyl ether were added to be a solvent ratio of propylene glycol monomethyl ether acetate/propylene glycol monoethyl ether of 20/80 and to adjust the concentration to 15 percent by weight in terms of solid residue at 140° C. The obtained polymer corresponds to Formula (A-14) and had a weight average molecular weight Mw of 2,500 in terms of polystyrene by GPC.

Synthesis Example 15

Into a 300-ml flask, 3.30 g (5% by mol) of 3-(triethoxysilylpropyl)diallyl isocyanurate, 2.31 g (5% by mol) of 4-(methylsulfonylmethyl)phenyltrimethoxysilane (Compound 9), 24.91 g (75% by mol) of tetraethoxysilane, 2.76 g (9.7% by mol) of methyltriethoxysilane, 2.28 g (5% by mol) of (4-(1-ethoxyethoxy)phenyl)trimethoxysilane, 0.13 g (0.3% by mol) of N-(3-triethoxysilylpropyl)-4,5-dihydroimidazole, and 53.54 g of acetone were charged. To the mixed solution, 10.79 g of 0.10 mol/l hydrochloric acid was added dropwise while the mixed solution was stirred with a magnetic stirrer. After the addition, the flask was transferred into an oil bath adjusted at 85° C., and the mixture was heated and refluxed for 240 minutes to be reacted. Then, the reaction solution was cooled to room temperature. To the reaction solution, 72.00 g of propylene glycol monoethyl ether was added. Methanol, ethanol, and water as reaction by-products, hydrochloric acid, and acetone were distilled off under reduced pressure to concentrate the reaction solution, thus affording a solution of the hydrolysis-condensation product (polymer) in propylene glycol monoethyl ether. The solution was diluted to adjust the concentration to 15 percent by weight in terms of solid residue at 140° C. The obtained polymer corresponds to Formula (A-15) and had a weight average molecular weight Mw of 2,500 in terms of polystyrene by GPC.

Synthesis Example 16

Into a 300-ml flask, 2.43 g (5% by mol) of 4-(methylsulfonylmethyl)phenyltrimethoxysilane (Compound 9), 26.13 g (75% by mol) of tetraethoxysilane, 4.38 g (14.7% by mol) of methyltriethoxysilane, 2.40 g (5% by mol) of (4-(1-ethoxyethoxy)phenyl)trimethoxysilane, 0.14 g (0.3% by mol) of N-(3-triethoxysilylpropyl)-4,5-dihydroimidazole, and 53.22 g of acetone were charged. To the mixed solution, 11.32 g of 0.10 mol/l hydrochloric acid was added dropwise while the mixed solution was stirred with a magnetic stirrer. After the addition, the flask was transferred into an oil bath adjusted at 85° C., and the mixture was heated and refluxed for 240 minutes to be reacted. Then, the reaction solution was cooled to room temperature. To the reaction solution, 72.00 g of propylene glycol monoethyl ether was added. Methanol, ethanol, and water as reaction by-products, hydrochloric acid, and acetone were distilled off under reduced pressure to concentrate the reacted solution, thus affording a solution of the hydrolysis-condensation product (polymer) in propylene glycol monoethyl ether. The solution was diluted to adjust the concentration to 15 percent by weight in terms of solid residue at 140° C. The obtained polymer corresponds to Formula (A-16) and had a weight average molecular weight Mw of 2,500 in terms of polystyrene by GPC.

Synthesis Example 17

Into a 300-ml flask, 3.44 g (5% by mol) of (3-(4-((trifluoromethyl)sulfonyl)phenoxy)propyl)triethoxysilane (Compound 13), 23.30 g (70% by mol) of tetraethoxysilane, 5.70 g (20% by mol) of methyltriethoxysilane, 3.30 g (5% by mol) of 3-(triethoxysilylpropyl)diallyl isocyanurate, and 53.61 g of acetone were charged. To the mixed solution, 10.66 g of 0.01 mol/l hydrochloric acid was added dropwise while the mixed solution was stirred with a magnetic stirrer. After the addition, the flask was transferred into an oil bath adjusted at 85° C., and the mixture was heated and refluxed for 240 minutes to be reacted. Then, the reaction solution was cooled to room temperature. To the reaction solution, 72.00 g of propylene glycol monoethyl ether acetate was added. Methanol, ethanol, and water as reaction by-products, hydrochloric acid, and acetone were distilled off under reduced pressure to concentrate the reaction solution, thus affording a solution of the hydrolysis-condensation product (polymer) in propylene glycol monomethyl ether acetate. To the solution, propylene glycol monomethyl ether acetate and propylene glycol monoethyl ether were added to be a solvent ratio of propylene glycol monomethyl ether acetate/propylene glycol monoethyl ether of 20/80 and to adjust the concentration to 15 percent by weight in terms of solid residue at 140° C. The obtained polymer corresponds to Formula (A-17) and had a weight average molecular weight Mw of 1,500 in terms of polystyrene by GPC.

Comparative Synthesis Example 1

Into a 300-ml flask, 3.48 g (5% by mol) of 3-(triethoxysilylpropyl)diallyl isocyanurate, 24.53 g (70% by mol) of tetraethoxysilane, 7.50 g (25% by mol) of methyltriethoxysilane, and 53.27 g of acetone were charged. To the mixed solution, 11.22 g of 0.01 mol/l hydrochloric acid was added dropwise while the mixed solution was stirred with a magnetic stirrer. After the addition, the flask was transferred into an oil bath adjusted at 85° C., and the mixture was heated and refluxed for 240 minutes to be reacted. Then, the reaction solution was cooled to room temperature. To the reaction solution, 72.00 g of propylene glycol monomethyl ether acetate was added. Ethanol and water as reaction by-products, hydrochloric acid, and acetone were distilled off under reduced pressure to concentrate the reaction solution, thus affording a solution of the hydrolysis-condensation product (polymer) in propylene glycol monomethyl ether acetate. To the solution, propylene glycol monomethyl ether acetate and propylene glycol monoethyl ether were added to be a solvent ratio of propylene glycol monomethyl ether acetate/propylene glycol monoethyl ether of 20/80 and to adjust the concentration to 15 percent by weight in terms of solid residue at 140° C. The obtained polymer corresponds to Formula (B-1) and had a weight average molecular weight Mw of 1,800 in terms of polystyrene by GPC.

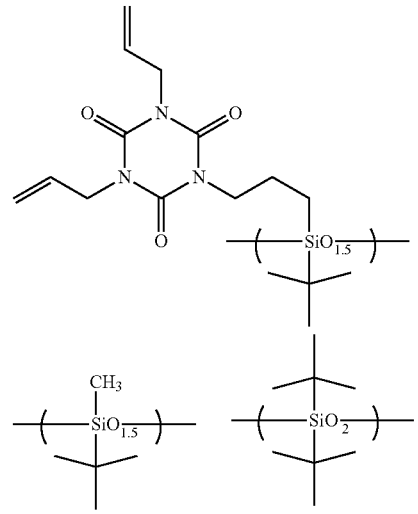

Formula (B-1)

Comparative Synthesis Example 2

Into a 300-ml flask, 2.81 g (5% by mol) of 3-triethoxysilylpropoxy methyl ethyl sulfone (Compound 2), 24.98 g (70% by mol) of tetraethoxysilane, 7.64 g (25% by mol) of methyltriethoxysilane, and 53.15 g of acetone were charged.

To the mixed solution, 11.42 g of 0.01 mol/l hydrochloric acid was added dropwise while the mixed solution was stirred with a magnetic stirrer. After the addition, the flask was transferred into an oil bath adjusted at 85° C., and the mixture was heated and refluxed for 240 minutes to be reacted. Then, the reaction solution was cooled to room temperature. To the reaction solution, 72.00 g of propylene glycol monomethyl ether acetate was added. Ethanol and water as reaction by-products, hydrochloric acid, and acetone were distilled off under reduced pressure to concentrate the reaction solution, thus affording a solution of the hydrolysis-condensation product (polymer) in propylene glycol monomethyl ether acetate. To the solution, propylene glycol monomethyl ether acetate and propylene glycol monoethyl ether were added to be a solvent ratio of propylene glycol monomethyl ether acetate/propylene glycol monoethyl ether of 20/80 and to adjust the concentration to 15 percent by weight in terms of solid residue at 140° C. The obtained polymer corresponds to Formula (B-2) and had a weight average molecular weight Mw of 1,600 in terms of polystyrene by GPC.

Formula (B-2)

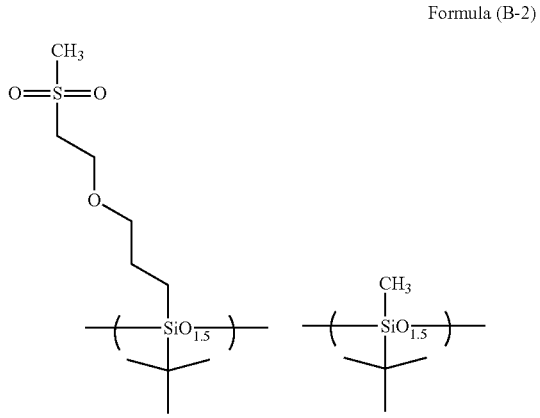

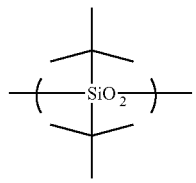

(Preparation of Composition for Forming Resist Underlayer Film)

The silicon-containing polymers obtained in Synthesis Example 1 to Synthesis Example 17, Comparative Synthesis Example 1, and Comparative Synthesis Example 2, an acid, a curing catalyst, an additive, a solvent, and water were mixed so as to give the ratios shown in Table 1, and the mixture was filtered through a 0.1-μm fluorine resin filter to prepare a solution of each composition for forming a resist underlayer film. The addition ratio of each polymer shown in Table 1 represents the mass of the polymer itself rather than the mass of a solution of the polymer.

The following abbreviations are used in Table 1. Maleic acid is MA, benzyltriethylammonium chloride is BTEAC, N-(3-triethoxysilylpropyl)-4,5-dihydroimidazole is IMIDTEOS, triphenylsulfonium trifluoromethanesulfonate is TPS105, mono-triphenylsulfonium maleate is TPSMA, triphenylsulfonium camphorsulfonate is TPSCS, propylene glycol monomethyl ether acetate is PGMEA, propylene glycol monoethyl ether is PGEE, and propylene glycol monomethyl ether is PGME. Ultrapure water was used for water. Each amount added was represented by parts by mass.

TABLE 1

Preparation of Composition for Forming Resist Underlayer Film

| | Polymer | Acid | Curing catalyst | Additive | Solvents | | | Water |
|---|---|---|---|---|---|---|---|---|
| Example 1 (parts by mass) | Synthesis Example 1 2 | MA 0.02 | IMIDTEOS 0.012 | | PGME 10 | PGEE 76 | PGMEA 7 | Water 7 |
| Example 2 (parts by mass) | Synthesis Example 2 2 | MA 0.02 | IMIDTEOS 0.012 | | PGME 10 | PGEE 76 | PGMEA 7 | Water 7 |
| Example 3 (parts by mass) | Synthesis Example 3 2 | MA 0.02 | IMIDTEOS 0.012 | | PGME 10 | PGEE 76 | PGMEA 7 | Water 7 |
| Example 4 (parts by mass) | Synthesis Example 4 2 | MA 0.02 | IMIDTEOS 0.012 | | PGME 10 | PGEE 76 | PGMEA 7 | Water 7 |
| Example 5 (parts by mass) | Synthesis Example 5 2 | MA 0.02 | IMIDTEOS 0.012 | | PGME 10 | PGEE 76 | PGMEA 7 | Water 7 |
| Example 6 (parts by mass) | Synthesis Example 6 2 | MA 0.02 | IMIDTEOS 0.012 | | PGME 10 | PGEE 76 | PGMEA 7 | Water 7 |
| Example 7 (parts by mass) | Synthesis Example 7 2 | MA 0.02 | IMIDTEOS 0.012 | | PGME 10 | PGEE 76 | PGMEA 7 | Water 7 |
| Example 8 (parts by mass) | Synthesis Example 8 2 | MA 0.02 | IMIDTEOS 0.012 | | PGME 10 | PGEE 76 | PGMEA 7 | Water 7 |
| Example 9 (parts by mass) | Synthesis Example 9 2 | MA 0.02 | IMIDTEOS 0.012 | | PGME 10 | PGEE 76 | PGMEA 7 | Water 7 |
| Example 10 (parts by mass) | Synthesis Example 10 2 | MA 0.02 | IMIDTEOS 0.012 | | PGME 10 | PGEE 76 | PGMEA 7 | Water 7 |
| Example 11 (parts by mass) | Synthesis Example 11 2 | MA 0.02 | IMIDTEOS 0.012 | | PGME 10 | PGEE 76 | PGMEA 7 | Water 7 |
| Example 12 (parts by mass) | Synthesis Example 12 2 | MA 0.02 | IMIDTEOS 0.012 | | PGME 10 | PGEE 76 | PGMEA 7 | Water 7 |

TABLE 1-continued

Preparation of Composition for Forming Resist Underlayer Film

| | Polymer | Acid | Curing catalyst | Additive | | Solvents | | | Water |
|---|---|---|---|---|---|---|---|---|---|
| Example 13 (parts by mass) | Synthesis Example 13 2 | MA 0.02 | IMIDTEOS 0.012 | | | PGME 10 | PGEE 76 | PGMEA 7 | Water 7 |
| Example 14 (parts by mass) | Synthesis Example 14 2 | MA 0.02 | IMIDTEOS 0.012 | | | PGME 10 | PGEE 76 | PGMEA 7 | Water 7 |
| Example 15 (parts by mass) | Synthesis Example 5 2 | MA 0.02 | BTEAC 0.012 | | | PGME 10 | PGEE 76 | PGMEA 7 | Water 7 |
| Example 16 (parts by mass) | Synthesis Example 6 2 | MA 0.02 | TPSMA 0.012 | TPS105 0.02 | | PGME 10 | PGEE 76 | PGMEA 7 | Water 7 |
| Example 17 (parts by mass) | Synthesis Example 4 2 | MA 0.02 | IMIDTEOS 0.012 | BPS 0.1 | | PGME 10 | PGEE 76 | PGMEA 7 | Water 7 |
| Example 18 (parts by mass) | Synthesis Example 15 2 | MA 0.02 | | | | PGME 10 | PGEE 76 | PGMEA 7 | Water 7 |
| Example 19 (parts by mass) | Synthesis Example 16 2 | MA 0.02 | | | | PGME 10 | PGEE 76 | PGMEA 7 | Water 7 |
| Example 20 (parts by mass) | Synthesis Example 15 2 | MA 0.02 | | TPS105 0.02 | | PGME 10 | PGEE 76 | PGMEA 7 | Water 7 |
| Example 21 (parts by mass) | Synthesis Example 9 2 | MA 0.02 | IMIDTEOS 0.012 | TPSCS 0.02 | | PGME 10 | PGEE 76 | PGMEA 7 | Water 7 |
| Example 22 (parts by mass) | Synthesis Example 16 2 | MA 0.02 | | TPSCS 0.02 | | PGME 10 | PGEE 76 | PGMEA 7 | Water 7 |
| Example 23 (parts by mass) | Synthesis Example 16 2 | MA 0.02 | | TPSCS 0.02 | TPS105 0.02 | PGME 10 | PGEE 76 | PGMEA 7 | Water 7 |
| Example 24 (parts by mass) | Synthesis Example 17 2 | MA 0.02 | IMIDTEOS 0.012 | | | PGME 10 | PGEE 76 | PGMEA 7 | Water 7 |
| Comparative Example 1 (parts by mass) | Comparative Synthesis Example 1 2 | MA 0.02 | IMIDTEOS 0.012 | | | PGME 10 | PGEE 76 | PGMEA 7 | Water 7 |
| Comparative Example 2 (parts by mass) | Comparative Synthesis Example 2 2 | MA 0.02 | IMIDTEOS 0.012 | | | PGME 10 | PGEE 76 | PGMEA 7 | Water 7 |

(Preparation of Organic Underlayer Film (Layer A))

Under a nitrogen stream, carbazole (6.69 g, 0.040 mol, manufactured by Tokyo Chemical Industry Co., Ltd.), 9-fluorenone (7.28 g, 0.040 mol, manufactured by Tokyo Chemical Industry Co., Ltd.), and p-toluenesulfonic acid monohydrate (0.76 g, 0.0040 mol, manufactured by Tokyo Chemical Industry Co., Ltd.) were charged into a 100-mL four-necked flask, then 1,4-dioxane (6.69 g, manufactured by Kanto Chemical Co., Inc.) was added, and the whole was stirred. The mixture was heated to 100° C. to be dissolved and polymerization started. After 24 hours, the reaction mixture was allowed to cool to 60° C. Then, chloroform (34 g, manufactured by Kanto Chemical Co., Inc.) was added to dilute the mixture, and the diluted mixture was added to methanol (168 g, manufactured by Kanto Chemical Co., Inc.) for reprecipitation. The obtained precipitate was filtered and dried in a vacuum dryer at 80° C. for 24 hours to afford 9.37 g of an intended polymer (Formula (C-1), hereinafter abbreviated as PCzFL).

Formula (C-1)

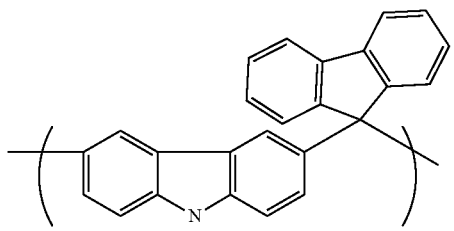

The $^1$H-NMR measurement result of PCzFL was as follows:

$^1$H-NMR (400 MHz, DMSO-$d_6$): δ7.03-7.55 (br, 12H), δ7.61-8.10 (br, 4H), δ11.18 (br, 1H).

PCzFL had a weight average molecular weight Mw of 2,800 and had a polydispersity Mw/Mn of 1.77 in terms of polystyrene by GPC.

To 20 g of the obtained resin, 3.0 g of tetramethoxymethylglycoluril (manufactured by Mitsui Cytec, Ltd., trade name: Powderlink 1174) as a cross-linking agent, 0.30 g of pyridinium p-toluenesulfonate as a catalyst, and 0.06 g of MEGAFAC R-30 (manufactured by Dainippon Ink and Chemicals, Inc., trade name) as a surfactant were mixed, and the mixture was dissolved in 88 g of propylene glycol monomethyl ether acetate to give a solution. Then, the solution was filtered through a polyethylene microfilter having a pore size of 0.10 µm and further filtered through a polyethylene microfilter having a pore size of 0.05 µm to prepare a solution of a composition for forming an organic underlayer film (layer A) to be used in a lithography process with a multilayer film.

(Measurement of Optical Constants)

Each of the compositions for forming a Si-containing resist underlayer film prepared in Example 1 to Example 24, Comparative Example 1, and Comparative Example 2 was applied onto a silicon wafer with a spinner. The coated silicon wafer was heated on a hot plate at 200° C. for one minute to form a Si-containing resist underlayer film (a film thickness of 0.05 µm). Then, the refractive index (n value) and the optical absorption coefficient (k value, also called attenuation coefficient) at a wavelength of 193 nm of each resist underlayer film were determined using a spectroscopic ellipsometer (manufactured by J.A. Woollam, VUV-VASE VU-302).

(Measurement of Dry Etching Rate)

The etcher and the etching gas used for the measurement of a dry etching rate were as follows:

ES401 (manufactured by Nippon Scientific Co., Ltd.): $CF_4$

RIE-10NR (manufactured by Samco Inc.): $O_2$

Each solution of the compositions for forming a Si-containing resist underlayer film prepared in Example 1 to Example 24, Comparative Example 1, and Comparative Example 2 was applied onto a silicon wafer with a spinner. The coated silicon wafer was heated on a hot plate at 240° C. for one minute. Thus, Si-containing resist underlayer films (a film thickness of 0.08 μm (for the measurement of an etching rate with a $CF_4$ gas) and a film thickness of 0.05 μm (for the measurement of an etching rate with an $O_2$ gas)) were each formed. In a similar manner, the composition for forming an organic underlayer film was applied onto a silicon wafer with a spinner to form a coating film (a film thickness of 0.20 μm). Each dry etching rate was determined using an $O_2$ gas as the etching gas, and the dry etching rates of the Si-containing resist underlayer films of Example 1 to Comparative Example 20, Comparative Example 1, and Comparative Example 2 were compared.

(Resist Patterning Evaluation)

The composition for forming an organic underlayer film (layer A) obtained in the above was applied onto a silicon wafer, and the coated silicon wafer was baked on a hot plate at 240° C. for 60 seconds to prepare an organic underlayer film (layer A) having a film thickness of 200 nm. Onto the organic underlayer film, each composition for forming a Si-containing resist underlayer film (layer B) obtained in Example 1 to Example 24, Comparative Example 1, and Comparative Example 2 was applied, and the coated silicon wafer was baked on a hot plate at 240° C. for 45 seconds to prepare a Si-containing resist underlayer film (layer B). The Si-containing resist underlayer film (layer B) had a film thickness of 45 nm.

Onto each Si-containing resist underlayer film, a commercially available photoresist solution (manufactured by JSR Corporation, trade name: AR2772) was applied with a spinner, and the coated silicon wafer was baked on a hot plate at 110° C. for 60 seconds to form a photoresist film (layer C) having a film thickness of 120 nm. The resist patterning was carried out using an ArF exposure apparatus S-307E manufactured by NIKON (a wavelength of 193 nm, NA, σ: 0.85, 0.93/0.85 (Dipole), immersion liquid: water). The photoresist was exposed through a mask designed so as to give a line width and a line spacing of 0.065 μm, namely, so as to form a line and space (dense line) of 0.065 μm, as a target after the development.

Subsequently, the substrate was baked on a hot plate at 110° C. for 60 seconds. The substrate was cooled, and then was developed with 2.38% by mass of aqueous tetramethylammonium hydroxide solution (developing solution) for 60 seconds by a single paddle procedure. After the lithography, a resist pattern having a rectangular foot is expressed as straight and that having a thick line bottom is expressed as footing.

Table 2 shows refractive indices n at a wavelength of 193 nm, optical absorption coefficients k at a wavelength of 193 nm, etching rates (etching speeds: nm/min) with a fluorine-containing gas ($CF_4$ gas), and resistances against an oxygen-containing gas ($O_2$ gas) that are represented by the ratio of etching rates [the resist underlayer film (layer B) of the present application]/[the organic underlayer film (layer A)]. The foot shape of each resist after the lithography evaluation was observed and the results are shown.

TABLE 2

Optical Characteristics and Etching Characteristics of Resist Underlayer Film and Resist Patterning Evaluation

| | Refractive index | Optical absorption coefficient | Etching rate with fluorine-containing gas | Resistance against oxygen-containing gas | Resist shape after lithography evaluation |
|---|---|---|---|---|---|
| Example 1 | 1.62 | 0.12 | 19.6 | 0.02 | Straight |
| Example 2 | 1.70 | 0.16 | 21.9 | 0.03 | Straight |
| Example 3 | 1.53 | 0.08 | 18.6 | 0.02 | Straight |
| Example 4 | 1.63 | 0.13 | 21.0 | 0.03 | Straight |
| Example 5 | 1.55 | 0.22 | 19.1 | 0.02 | Straight |
| Example 6 | 1.63 | 0.25 | 20.9 | 0.03 | Straight |
| Example 7 | 1.54 | 0.21 | 19.4 | 0.02 | Straight |
| Example 8 | 1.62 | 0.24 | 21.0 | 0.03 | Straight |
| Example 9 | 1.54 | 0.16 | 19.0 | 0.02 | Straight |
| Example 10 | 1.63 | 0.20 | 21.0 | 0.03 | Straight |
| Example 11 | 1.63 | 0.22 | 19.0 | 0.02 | Straight |
| Example 12 | 1.70 | 0.25 | 21.1 | 0.03 | Straight |
| Example 13 | 1.63 | 0.30 | 21.2 | 0.03 | Straight |
| Example 14 | 1.56 | 0.28 | 21.1 | 0.03 | Straight |
| Example 15 | 1.54 | 0.23 | 19.0 | 0.02 | Straight |
| Example 16 | 1.62 | 0.26 | 20.7 | 0.03 | Straight |
| Example 17 | 1.62 | 0.17 | 20.9 | 0.03 | Straight |
| Example 18 | 1.63 | 0.30 | 21.2 | 0.03 | Straight |
| Example 19 | 1.56 | 0.28 | 21.2 | 0.03 | Straight |
| Example 20 | 1.62 | 0.31 | 21.0 | 0.03 | Straight |
| Example 21 | 1.55 | 0.17 | 19.0 | 0.02 | Straight |
| Example 22 | 1.56 | 0.29 | 21.2 | 0.03 | Straight |
| Example 23 | 1.56 | 0.30 | 21.2 | 0.03 | Straight |
| Example 24 | 1.63 | 0.13 | 22.0 | 0.03 | Straight |
| Comparative Example 1 | 1.64 | 0.08 | 19.4 | 0.03 | Footing |
| Comparative Example 2 | 1.56 | 0.00 | 18.5 | 0.02 | Footing |

(Resist Patterning Evaluation by Solvent Development Process)

The composition for forming an organic underlayer film (layer A) obtained in the above was applied onto a silicon wafer, and the coated silicon wafer was baked on a hot plate at 240° C. for 60 seconds to afford an organic underlayer film (layer A) having a film thickness of 200 nm. Onto the organic underlayer film, the composition for forming a resist underlayer film of the present application was applied, and the coated silicon wafer was heated on a hot plate at 240° C. for one minute to form a resist underlayer film (layer B) having a film thickness of 35 nm. Onto each resist underlayer film, a commercially available photoresist solution (manufactured by Fujifilm Corporation, trade name: FAiRS-9521NT05) was applied with a spinner, and the coated silicon wafer was heated on a hot plate at 100° C. for one minute to form a photoresist film (layer C) having a film thickness of 85 nm.

Subsequently, each coated silicon wafer was exposed using NSR-S307E scanner manufactured by NIKON CORPORATION (a wavelength of 193 nm, NA, σ: 0.85, 0.93/0.85) through a mask designed so that the photoresist had a line width and a line spacing of 0.065 μm, namely, a dense line with 0.065-μm line and space (L/S)=1/1 was formed after the development. Then, the wafer was baked on a hot plate at 100° C. for 60 seconds. The wafer was cooled, and then was developed with butyl acetate (solvent as a developing solution) for 60 seconds to form a negative pattern on the resist underlayer film (layer B).

A photoresist pattern obtained without large pattern exfoliation or undercut was evaluated as good, which is shown in Table 3.

TABLE 3

Resist Patterning Evaluation by Solvent Development Process

| | Pattern formation | Pattern shape |
|---|---|---|
| Example 1 | Formed | Good |
| Example 3 | Formed | Good |
| Example 5 | Formed | Good |
| Example 7 | Formed | Good |
| Example 9 | Formed | Good |
| Example 11 | Formed | Good |
| Example 14 | Formed | Good |
| Example 16 | Formed | Good |
| Example 20 | Formed | Good |
| Example 21 | Formed | Good |
| Example 22 | Formed | Good |
| Example 23 | Formed | Good |
| Comparative Example 1 | Fallen | Undercut |
| Comparative Example 2 | Fallen | Undercut |

INDUSTRIAL APPLICABILITY

The composition can be used as a composition for forming a resist underlayer film for lithography in order to form a resist underlayer film usable as a hard mask. The composition causes no intermixing with an overcoated resist. The composition has a higher dry etching rate than that of a resist when a fluorine-containing etching gas is used, and thus it is possible to transfer a resist pattern to the resist underlayer film of the present application. In addition, the composition exhibits etching resistance against an oxygen-containing etching gas, and thus it is possible to transfer a resist pattern to an organic underlayer film. The composition for forming a resist underlayer film is provided in order to form a resist underlayer film that enables substrate fabrication with a rectangular pattern as described above.

The invention claimed is:

1. A composition for forming a resist underlayer film for lithography, comprising a co-hydrolysis condensation product of a hydrolyzable organosilane of the following Formula (1) and at least one organic silicon compound selected from the group consisting of the following Formula (3) and the following Formula (4):

$$[(R^1)_a Si(R^2)_{(3-a)}]_b (R^3) \qquad \text{Formula (1)}$$

[in Formula (1), $R^1$ is an alkyl group, an aryl group, an aralkyl group, a halogenated alkyl group, a halogenated aryl group, a halogenated aralkyl group, an alkenyl group, an organic group having an epoxy group, an acryloyl group, a methacryloyl group, a mercapto group, an alkoxyaryl group, an acyloxyaryl group, an isocyanurate group, a hydroxy group, a cyclic amino group, or a cyano group, or a combination of any of these groups and is bonded to a Si atom through a Si—C bond; $R^2$ is an alkoxy group, an acyloxy group, or a halogen group; a is an integer of 0 to 2; and b is an integer of 1 to 3],

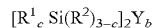
$$R^1{}_a Si(R^2)_{4-a} \qquad \text{Formula (3)}$$

[in Formula (3), $R^1$ is an alkyl group, an aryl group, an aralkyl group, a halogenated alkyl group, a halogenated aryl group, a halogenated aralkyl group, an alkenyl group, an organic group having an epoxy group, an acryloyl group, a methacryloyl group, a mercapto group, an alkoxyaryl group, an acyloxyaryl group, an isocyanurate group, a hydroxy group, a cyclic amino group, or a cyano group, or a combination of any of these groups and is bonded to a silicon atom through a Si—C bond; $R^2$ is an alkoxy group, an acyloxy group, or a halogen group; and a is an integer of 0 to 3],

$$[R^1{}_c Si(R^2)_{3-c}]_2 Y_b \qquad \text{Formula (4)}$$

[in Formula (4), $R^1$ is an alkyl group; $R^2$ is an alkoxy group, an acyloxy group, or a halogen group; Y is an alkylene group or an arylene group; b is an integer of 0 or 1; and c is an integer of 0 or 1], wherein $R^3$ in Formula (1) is a group of Formula (2):

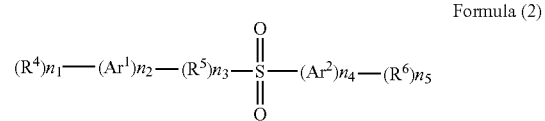

$$(R^4)_{n_1} - (Ar^1)_{n_2} - (R^5)_{n_3} - \overset{O}{\underset{O}{\overset{\|}{S}}} - (Ar^2)_{n_4} - (R^6)_{n_5} \qquad \text{Formula (2)}$$

[in Formula (2), one to three groups of groups of $R^4$, $Ar^1$, $R^5$, $Ar^2$, and $R^6$ are bonded to a Si atom through a Si—C bond; $R^4$ is a monovalent to tetravalent hydrocarbon group optionally having a sulfide bond or an ether bond; $R^5$ is a divalent to tetravalent hydrocarbon group optionally having a sulfide bond or an ether bond; $R^6$ is an optionally substituted monovalent to tetravalent hydrocarbon group; each of $Ar^1$ and $Ar^2$ is an optionally substituted $C_{6-20}$ arylene group or an optional substituted $C_{6-20}$ aryl group; $n_2$ is an integer of 1; each of $n_1$, $n_3$, $n_4$, and $n_5$ is an integer of 0 or 1; and $n_4$ and $n_5$ are not simultaneously an integer of 0].

2. The composition for forming a resist underlayer film according to claim 1, wherein the co-hydrolysis-condensation product is of the compound of Formula (1) and the compound of Formula (3) and is included as a polymer.

3. The composition for forming a resist underlayer film according to claim 1, further comprising an acid.

4. The composition for forming a resist underlayer film according to claim 1, further comprising water.

5. The composition for forming a resist underlayer film according to claim 1, further comprising an ammonium compound, a cyclic ammonium compound, a cyclic amine compound, or a sulfonium compound.

6. A resist underlayer film obtained by applying the composition for forming a resist underlayer film as claimed in claim 1 onto a semiconductor substrate and baking the composition.

7. A method for producing a semiconductor device, the method comprising:
applying the composition for forming a resist underlayer film as claimed in claim 1 onto a semiconductor substrate and baking the composition to faun a resist underlayer film;
applying a composition for a resist onto the resist underlayer film to form a resist film;
exposing the resist film to light;
after the light exposure, developing the resist film to form a resist pattern;
etching the resist underlayer film using the resist pattern; and
fabricating the semiconductor substrate using the resist film thus patterned and the resist underlayer film thus patterned.

8. A method for producing a semiconductor device, the method comprising:

forming an organic underlayer film on a semiconductor substrate;
applying the composition for forming a resist underlayer film as claimed in claim 1 onto the organic underlayer film and baking the composition to form a resist underlayer film;
applying a composition for a resist onto the resist underlayer film to form a resist film;
exposing the resist film to light;
after the light exposure, developing the resist film to form a resist pattern;
etching the resist underlayer film using the resist pattern;
etching the organic underlayer film using the resist underlayer film thus patterned; and
fabricating the semiconductor substrate using the organic underlayer film thus patterned.

9. The composition for forming a resist underlayer film for lithography according to claim 1, wherein b in Formula (1).

10. The composition for forming a resist underlayer film according to claim 1, further comprising:
a hydrolyzable organosilane consisting of a hydrolyzable organosilane of Formula (1) and at least one hydrolyzable organosilane selected from the group consisting of Formula (3) and Formula (4); or
a co-hydrolyzable product of the hydrolyzable organosilane.

11. A compound selected from the following group of compounds:

Compound 3

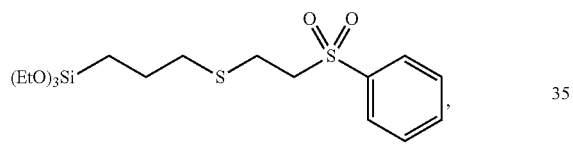

Compound 5

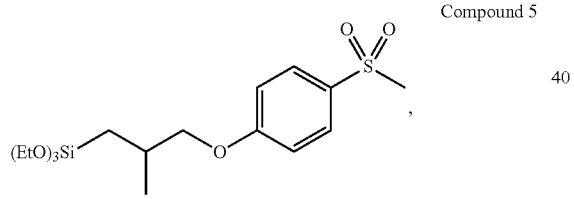

Compound 6

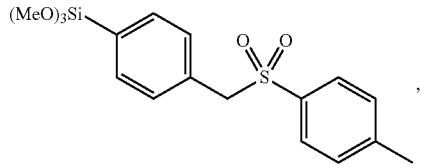

Compound 8

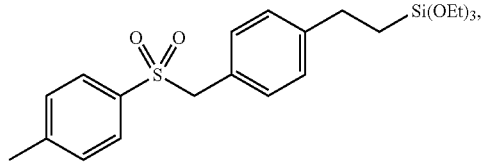

Compound 9

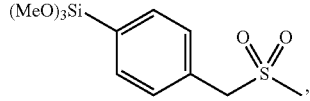

Compound 10

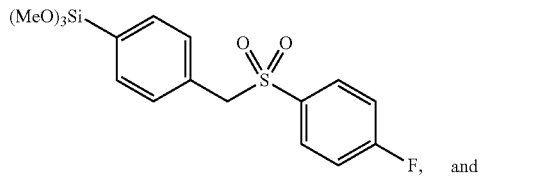, and

Compound 13

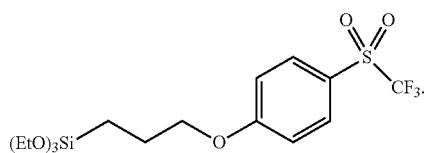

* * * * *